US010016382B2

(12) United States Patent
Lopez et al.

(10) Patent No.: US 10,016,382 B2
(45) Date of Patent: Jul. 10, 2018

(54) METHOD FOR DECREASING SKELETAL MUSCLE DAMAGE AND/OR OXIDATIVE STRESS IN MAMMALS

(71) Applicant: LONZA INC., Allendale, NJ (US)

(72) Inventors: Johnny Lopez, North Richland Hills, TX (US); Kevin Owen, Canyon, TX (US); Jason Woodworth, Enterprise, KS (US); Craig Coon, Fayetteville, AR (US); George Collings, O Fallon, MO (US)

(73) Assignee: Lonza Inc., Allendale, NJ (US)

( * ) Notice: Subject to any disclaimer, the term of this patent is extended or adjusted under 35 U.S.C. 154(b) by 0 days.

(21) Appl. No.: 14/736,775

(22) Filed: Jun. 11, 2015

(65) Prior Publication Data

US 2015/0359769 A1    Dec. 17, 2015

Related U.S. Application Data

(60) Provisional application No. 62/011,345, filed on Jun. 12, 2014, provisional application No. 62/147,065, filed on Apr. 14, 2015.

(51) Int. Cl.
| | |
|---|---|
| *A61K 31/205* | (2006.01) |
| *A61K 31/197* | (2006.01) |
| *A23K 20/174* | (2016.01) |
| *A23K 20/142* | (2016.01) |
| *A23K 50/40* | (2016.01) |
| *A23L 33/15* | (2016.01) |
| *A23L 33/175* | (2016.01) |

(52) U.S. Cl.
CPC .......... *A61K 31/197* (2013.01); *A23K 20/142* (2016.05); *A23K 20/174* (2016.05); *A23K 50/40* (2016.05); *A23L 33/15* (2016.08); *A23L 33/175* (2016.08); *A61K 31/205* (2013.01); *A23V 2002/00* (2013.01)

(58) Field of Classification Search
CPC .................................. A61K 31/205
See application file for complete search history.

(56) References Cited

U.S. PATENT DOCUMENTS

| | | | |
|---|---|---|---|
| 4,687,782 A | 8/1987 | Brantman | |
| 4,883,672 A | 11/1989 | Shug et al. | |
| 6,159,942 A | 12/2000 | St. Cyr et al. | |
| 6,245,378 B1 | 6/2001 | Cavazza | |
| 6,602,512 B1 | 8/2003 | Cavazza | |
| 8,029,819 B2 | 10/2011 | Bierer et al. | |
| 8,535,708 B2 | 9/2013 | Wedekind et al. | |
| 2001/0043983 A1 | 11/2001 | Hamilton | |
| 2014/0193370 A1 | 7/2014 | Tissot-Favre et al. | |

FOREIGN PATENT DOCUMENTS

FR            2938733 A1    5/2010

OTHER PUBLICATIONS

English Machine Translation of FR2938733A1. Originally Published May 28, 2010, Machine Translated Apr. 13, 2016.*
Iben, CH. J. Anim. Physiol. a. Anim. Nutr., 1999, vol. 82, pp. 66-79 (Year: 1999).*
Jeff S. Volek, et al., L-Carnitine L-tartrate supplementation favorably affects markers of recovery from exercise stress, American Journal of Physiology: Endocrinology and Metabolism, American Physiological Society, Bethesda, MD., vol. 282, Jan. 1, 2002, pp. E474-E482.
Khadijeh Parandak, et al., The Effect of Two-Week L-Carnitine Supplementation on Exercise-Induced Oxidative Stress and Muscle Damage, Asian J Sports Medicine Asian Journal of Sports Medicine, vol. 5 (No. 2), Tehran, Iran, Mar. 1, 2014, p. 123-128
William J. Kraemer, et al., L-Carnitine Supplementation: Influence upon Physiological Function, Human performance Laboooratory, Department of Kinesiology, Department of Physiology and Neurobilogy, Current Sports Medicine Report, 2008, vol. 7, No. 4, pp. 218-223.
Amy Huang et al., Role of Supplementary L-Carnitine in Exercise and Exercise Recovery, Lamprecht M (ed) Acute Topics in sport Nutrition, Medical Sports Science Basel, Karger, 2013, vol. 59. pp. 135-142.
William J. Kraemer, et al., The Effects of L-Carnitine L-Tartrate Supplementation on Hormonal Responses to Resistance Exercise and Recovery, Journal of Strength and Conditioning Research, 2003, vol. 17, No. 3, pp. 455-462.
William J. Kraemer, et al. ,L -Carnitine Supplementation: A New Paradigm for its Role in Exercise, Monatshefte fur Chemie Chemical Monthly, Published online Jun. 10, 2005, pp. 1383-1390.
Jen-Yu Ho, et al., L-Carnitine L-tartrate supplementation favorably affects biochemical markers of recovery from physical exertion in middle aged men and women, Science Direct, Metabolism Clinical and Experimental 59 (2010) pp. 1190-1199.
William J. Kraemer,et al., Androgenic Responses to Resistance Exercise: Effects of Feeding and L-Carnitine, Medicine & Science in Sports & Exercise, 2006, vol. 38, No. 7, pp. 1288-1296.
Martyn R. Rubin, et al. Safety Measures of L-Carnitine L-Tartrate Supplementation in Healthy Men, Journal of Strength and Conditioning Research, 2001, vol. 15, No. 4 pp. 486-490.
Barry A. Spiering, et al., Effects of L-Carnitine L-Tartrate Supplementation on Muscle Oxygenation Responses to Resistance Exercise, Journal of Strength and Conditioning Research vol. 22, No. 4, Jul. 2008, pp. 1130-1135.
Barry A. Spiering, et al. Responses of Criterion Variables to Different Supplemental Doses of L-Carnitine L-Tartrate, Journal of Strength and Conditioning Research, 2007, vol. 21, No. 1, pp. 259-264.

(Continued)

*Primary Examiner* — James D. Anderson
(74) *Attorney, Agent, or Firm* — Dority & Manning, P.A.

(57) ABSTRACT

A method for reducing muscle damage and/or oxidative stress in active mammals as disclosed. In one embodiment, the mammals are administered a carnitine supplement. The L-carnitine supplement may be administered without any other pharmaceutical or drug products. After physical activity the L-carnitine supplement can lower myoglobin, TBARS, and creatine kinase in the bloodstream.

17 Claims, 53 Drawing Sheets

(56) References Cited

OTHER PUBLICATIONS

Jeff S. Volek, et al., Effects of Carnitine Supplementation on Flow-Mediated Dilation and Vascular Inflammatory Responses to a High Fat Meal in Healthy Young Adults, The American Journal of Cardiology 2008, Vol. 102, pp. 1413-1417.

International Search Report and Written Opinion dated Jul. 31, 2015, for International Patent Application No. PCT/US2015/035286, filed Jun. 11, 2015, 13 pages.

* cited by examiner

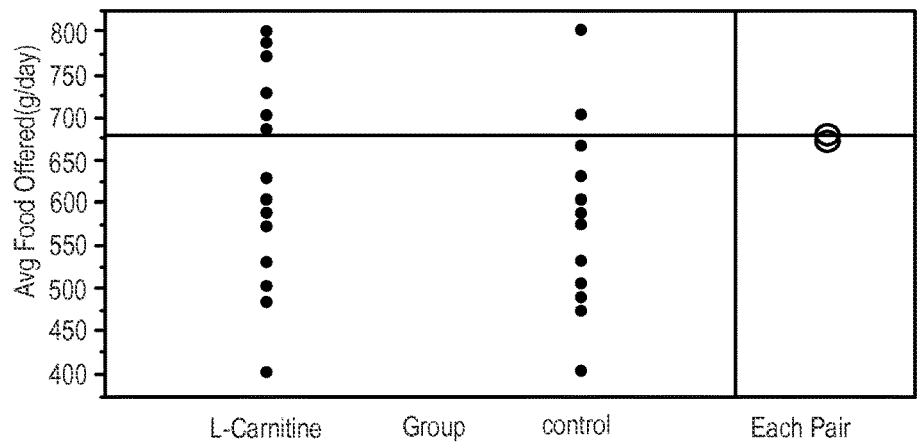

t Test
Control- L-Carnitine
Assuming unequal variances

| | | |
|---|---|---|
| Difference | 6.513 | t Ratio 0.766378 |
| Std Err Dif | 8.498 | DF 781.9743 |
| Upper CL Dif | 23.195 | Prob > \|t\| 0.4437 |
| Lower CL Dif | -10.169 | Prob > t 0.2218 |
| Confidence | 0.95 | Prob < t 0.7782 |

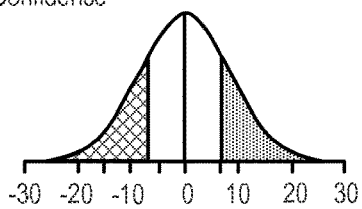

Means Comparisons
Comparisons for each pair using Student's t
Confidence Quantile
    t        Alpha
1.96300     0.05
LSD Threshold Matrix
Abs(Dif)-LSD

| | Control | L-Carnitine |
|---|---|---|
| Control | -16.682 | -10.169 |
| L-Carnitine | -10.169 | -16.682 |

Positive values show pairs of means that are significantly different.
Connecting Letters Report

| Level | | Mean |
|---|---|---|
| Control | A | 683.12500 |
| L-Carnitine | A | 676.61224 |

Levels not connected by same letter are significantly different

FIG. 7

Oneway Analysis of Overall Mean Daily Food Intake over 14 wk Duration/kg Lean Mass (g/d/kg LM) By Treatment Time=Change.

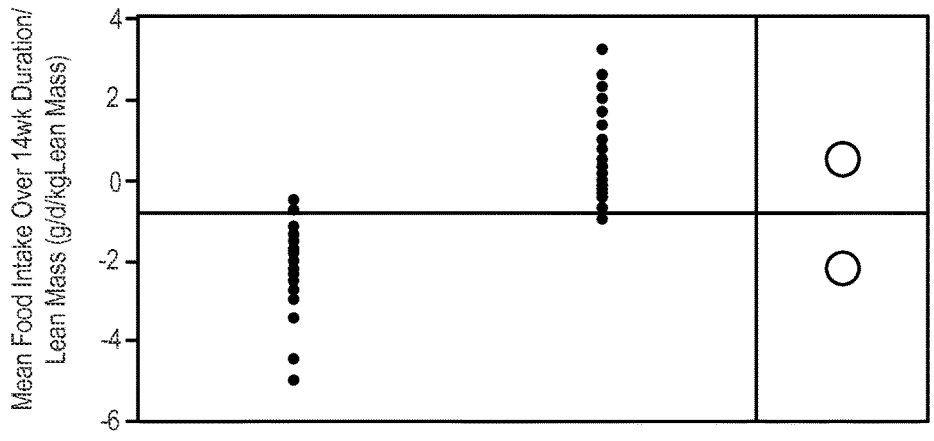

t Test
Control- L-Carnitine
Assuming unequal variances

| | | | |
|---|---|---|---|
| Difference | 2.74607 | t Ratio | 9.705841 |
| Std Err Dif | 0.28293 | DF | 53.37176 |
| Upper CL Dif | 3.31346 | Prob > \|t\| | <.0001* |
| Lower CL Dif | 2.17868 | Prob > t | <.0001* |
| Confidence | 0.95 | Prob < t | 1.0000 |

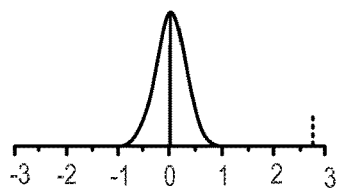

Means Comparisons
Comparisons for each pair using Student's t
Confidence Quantile

| t | Alpha |
|---|---|
| 2.00488 | 0.05 |

LSD Threshold Matrix
Abs(Dif)-LSD

| | Control | L-Carnitine |
|---|---|---|
| Control | -0.5672 | 2.1788 |
| L-Carnitine | 2.1788 | -0.5672 |

Positive values show pairs of means that are significantly different.

Connecting Letters Report

| Level | | Mean |
|---|---|---|
| Control | A | 0.524643 |
| L-Carnitine | B | -2.221429 |

Levels not connected by same letter are significantly different.

FIG. 10A

Oneway Analysis of Overall FEMALE Mean Daily Food Intake over 14 wk Duration/ kg Lean Mass (g/d/kg LM) By Gender and Treatment
Time=Change.
Sex=Female

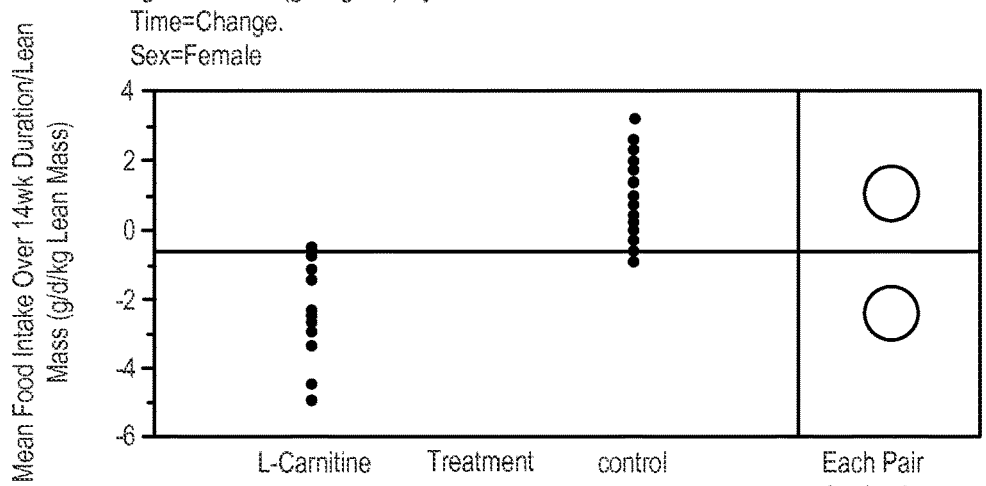

t Test
Control-L-Carnitine
Assuming unequal variances

| | | | |
|---|---|---|---|
| Difference | 3.50657 | t Ratio | 7.507462 |
| Std Err Dif | 0.46708 | DF | 26.79302 |
| Upper CL Dif | 4.46528 | Prob > \|t\| | <.0001* |
| Lower CL Dif | 2.54786 | Prob > t | <.0001* |
| Confidence | 0.95 | Prob < t | 1.0000 |

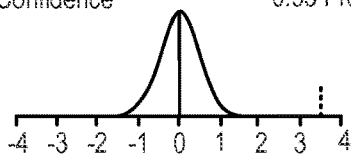

Means Comparisons
Comparisons for each pair using Student's t
Confidence Quantile

| t | Alpha |
|---|---|
| 2.05183 | 0.05 |

LSD Threshold Matrix
Abs(Dif)-LSD

| | Control | L-Carnitine |
|---|---|---|
| Control | -0.9411 | 2.5488 |
| L-Carnitine | 2.5488 | -0.9742 |

Positive values show pairs of means that are significantly different.

Connecting Letters Report

| Level | | Mean |
|---|---|---|
| Control | A | 1.048000 |
| L-Carnitine | B | -2.458571 |

Levels not connected by same letter are significantly different.

FIG. 10B

Oneway Analysis of Overall MALE Mean Daily Food Intake over 14 wk Duration/kg Lean Mass (g/d/kg LM) By Gender and Treatment
Time=Change.
Sex=Male

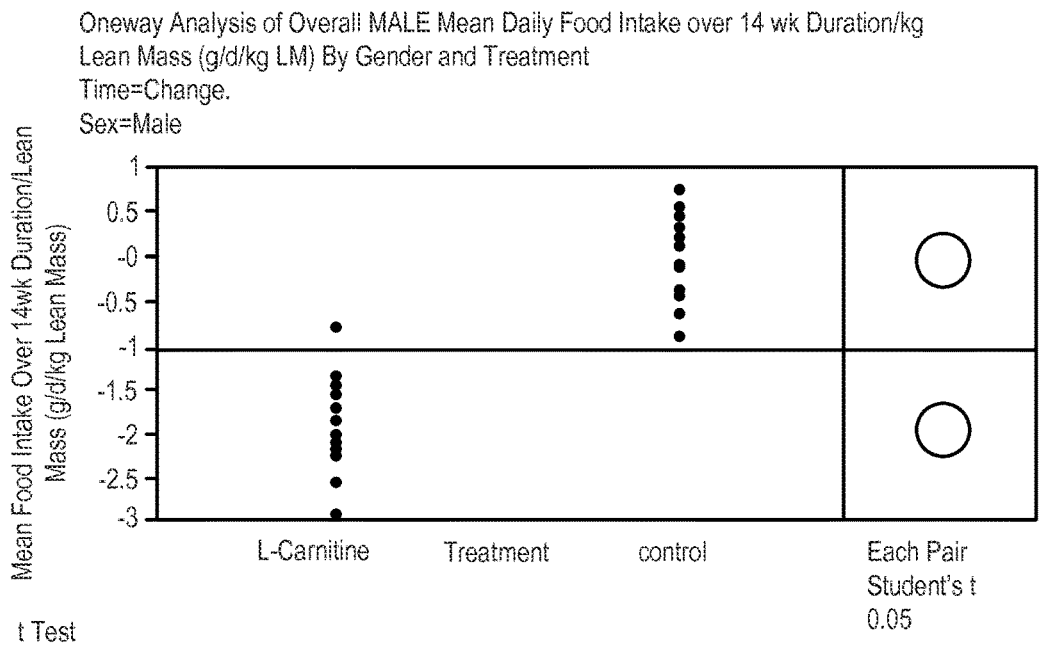

t Test
Control-L-Carnitine
Assuming unequal variances

| | | | |
|---|---|---|---|
| Difference | 1.90505 | t Ratio | 9.097732 |
| Std Err Dif | 0.20940 | DF | 24.76284 |
| Upper CL Dif | 2.33653 | Prob > \|t\| | <.0001* |
| Lower CL Dif | 1.47358 | Prob > t | <.0001* |
| Confidence | 0.95 | Prob < t | 1.0000 |

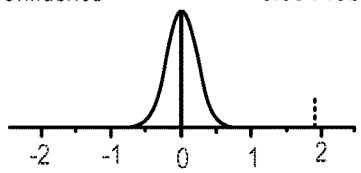

Means Comparisons
Comparisons for each pair using Student's t
Confidence Quantile
    t      Alpha
2.05954    0.05
LSD Threshold Matrix
Abs(Dif)-LSD

| | Control | L-Carnitine |
|---|---|---|
| Control | -0.4421 | 1.4709 |
| L-Carnitine | 1.4709 | -0.4260 |

Positive values show pairs of means that are significantly different.

Connecting Letters Report

| Level | | Mean |
|---|---|---|
| Control | A | -0.079231 |
| L-Carnitine | B | -1.984286 |

Levels not connected by same letter are significantly different.

FIG. 10C

APM/kg (Activity/Mile/kg BW) for All Exercise for Test Dogs Using a Oneway Analysis

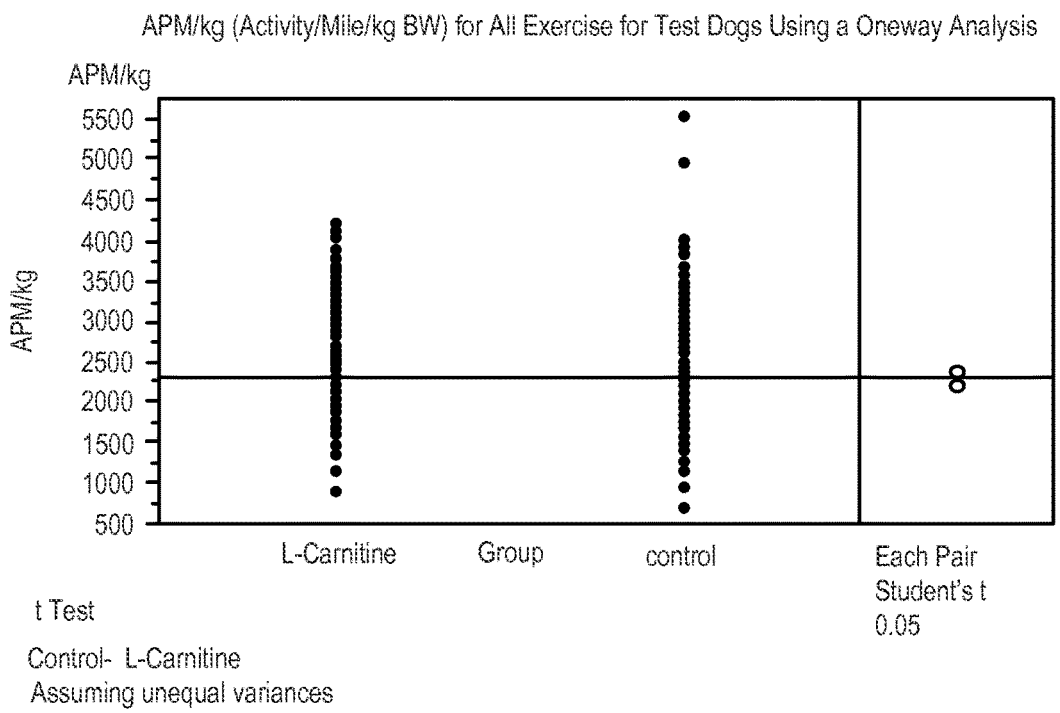

t Test
Control- L-Carnitine
Assuming unequal variances

| | | | |
|---|---|---|---|
| Difference | 134.635 | t Ratio | 3.340122 |
| Std Err Dif | 40.308 | DF | 778.8968 |
| Upper CL Dif | 213.761 | Prob > \|t\| | 0.0009* |
| Lower CL Dif | 55.509 | Prob > t | 0.0004* |
| Confidence | 0.95 | Prob < t | 0.9996 |

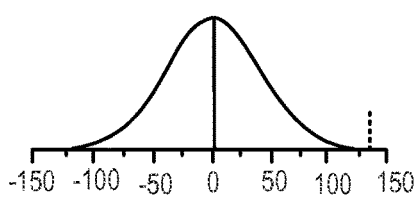

Means Comparisons
Comparisons for each pair using Student's t
Confidence Quantile

| t | Alpha |
|---|---|
| 1.96300 | 0.05 |

Connecting Letters Report

| Level | | Mean |
|---|---|---|
| Control | A | 2365.9617 |
| L-Carnitine | B | 2231.3265 |

Levels not connected by same letter are significantly different.

FIG. 12A

APM/kg for Females (Activity/Mile/kg BW) for All exercise for Test Dogs Using a Oneway Analysis.

Oneway Analysis of APM/kg By Group Gender=Female
 t Test
 Control- L-Carnitine
 Assuming unequal variances

| | | |
|---|---|---|
| Difference | -30.02 t Ratio | -0.5378 |
| Std Err Dif | 55.81 DF | 375.2932 |
| Upper CL Dif | 79.73 Prob > \|t\| | 0.5910 |
| Lower CL Dif | -139.76 Prob > t | 0.7045 |
| Confidence | 0.95 Prob < t | 0.2955 |

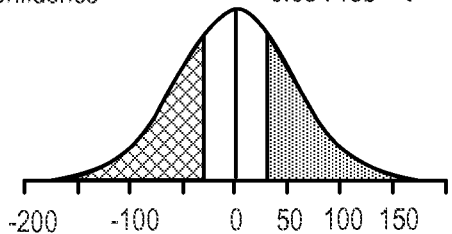

-200  -100   0   50  100  150

Means Comparisons
Comparisons for each pair using Student's t
Confidence Quantile
          t        Alpha
       1.96593    0.05
LSD Threshold Matrix
Abs(Dif-)LSD

| | L-Carnitine | Control |
|---|---|---|
| L-Carnitine | -111.45 | -78.89 |
| Control | -78.89 | -106.29 |

Positive values show pairs of means that are significantly different.
Connecting Letters Report

| Level | | Mean |
|---|---|---|
| L-Carnitine | A | 2433.2199 |
| Control | A | 2403.2048 |

Levels not connected by same letter are significantly different.

FIG. 12B

APM/kg for Males (Activity/Mile/kg BW) for All exercise for Test Dogs Using a Oneway Analysis.

Oneway Analusis of APM/kg By Group Gender=Male
t Test
Control L-Carnitine
Assuming unequal variances

| | | | |
|---|---|---|---|
| Difference | 257.136 | t Ratio | 4.5683 |
| Std Err Dif | 56.287 | DF | 356.0758 |
| Upper CL Dif | 367.833 | Prob > \|t\| | <.0001* |
| Lower CL Dif | 146.439 | Prob > t | <.0001* |
| Confidence | 0.95 | Prob < t | 1.0000 |

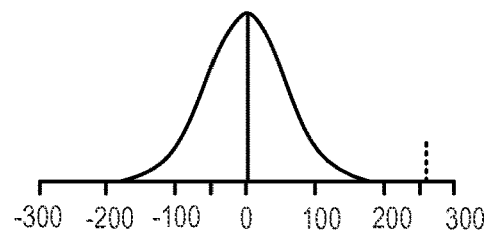

Means Comparisons
Comparisons for each pair using Student's t
Confidence Quantile

| t | Alpha |
|---|---|
| 1.96629 | 0.05 |

LSD Threshold Matrix
Abs(Dif)-LSD

| | Control | L-Carnitine |
|---|---|---|
| Control | -112.03 | 147.13 |
| L-Carnitine | 147.13 | -107.95 |

Positive values show pairs of means that are significantly different.
Connecting Letters Report

| Level | | Mean |
|---|---|---|
| Control | A | 2312.1209 |
| L-Carnitine | B | 2054.9847 |

Levels not connected by same letter are significantly different.

FIG. 12C

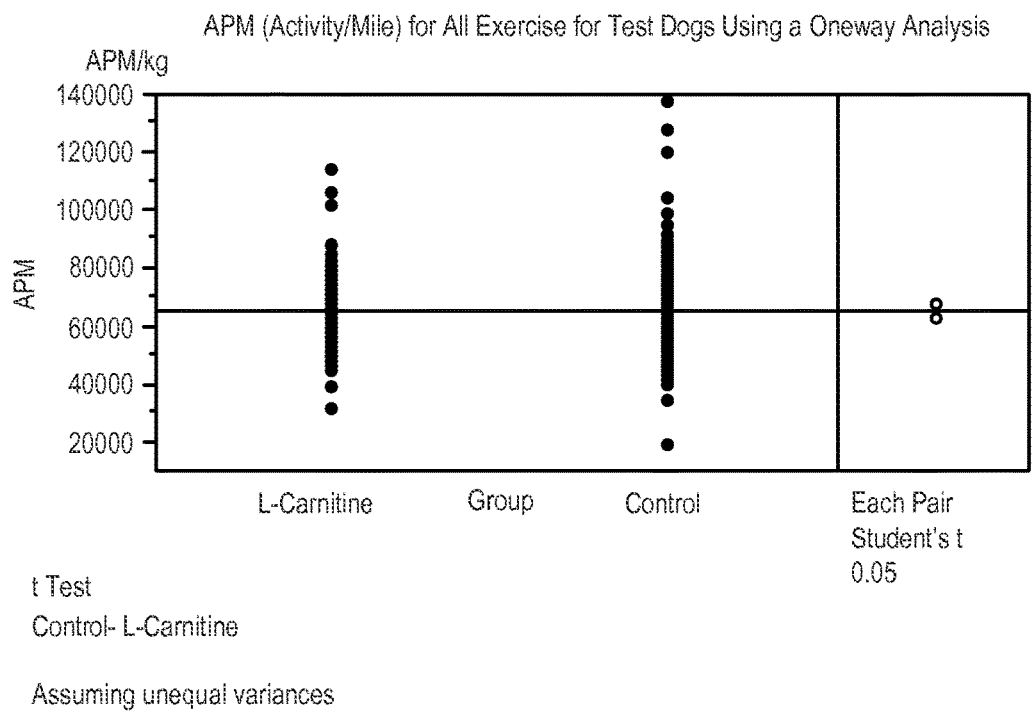

APM (Activity/Mile) for All Exercise for Test Dogs Using a Oneway Analysis t Test
Control- L-Carnitine Assuming unequal variances

| Difference | 2374.80 | t Ratio | 2.9418 |
|---|---|---|---|
| Std Err Dif | 807.26 | DF | 707.9401 |
| Upper CL Dif | 3959.71 | Prob > |t| | 0.0034* |
| Lower CL Dif | 789.89 | Prob > t | 0.0017* |
| Confidence | 0.95 | Prob < t | 0.9983 |

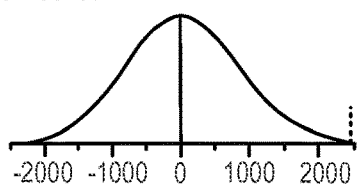

Means Comparisons

Comparisons for each pair using Student's t

Confidence Quantile

| t | Alpha |
|---|---|
| 1.96300 | 0.05 |

Connecting Letters Report

| Level | | Mean |
|---|---|---|
| Control | A | 66083.758 |
| L-Carnitine | B | 63708.959 |

Levels not connected by same letter are significantly different.

FIG. 13A

APM for Females (Activity/Mile) for All Exercise for Test Dogs Using a Oneway Analysis Fit Group Gender=Female
Oneway Analysis of APM By Group Gender=Female t Test
Control- L-Carnitine
Assuming unequal variances

| | | |
|---|---|---|
| Difference | -172.4 t Ratio | -0.15 |
| Std Err Dif | 1149.1 DF | 398.2536 |
| Upper CL Dif | 2086.7 Prob > \|t\| | 0.8808 |
| Lower CL Dif | -2431.4 Prob > t | 0.5596 |
| Confidence | 0.95 Prob < t | 0.4404 |

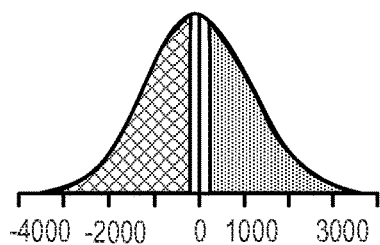

-4000 -2000  0 1000  3000

Means Comparisons
Comparisons for each pair using Student's t

Confidence Quantile
  t      Alpha
1.96593   0.05

LSD Threshold Matrix
Abs(Dif)-LSD

| | L-Carnitine | Control |
|---|---|---|
| L-Carnitine | -2317.6 | -2092.2 |
| Control | -2092.2 | -2210.3 |

Positive values show pairs of means that are significantly different.

Connecting Letters Report

| Level | | Mean |
|---|---|---|
| L-Carnitine | A | 65413.455 |
| Control | A | 65241.086 |

Levels not connected by same letter are significantly different.

FIG. 13B

APM for Males (Activity/Mile) for All Exercise for Test Dogs Using a Oneway Analysis Fit Group Gender=Male
Oneway Analysis of APM By Group Gender=Male t Test
Assuming unequal variances

| | | | |
|---|---|---|---|
| Difference | 4716.70 | t Ratio | 4.131281 |
| Std Err Dif | 1141.70 | DF | 334.6411 |
| Upper CL Dif | 6962.52 | Prob > \|t\| | <.0001* |
| Lower CL Dif | 2470.88 | Prob > t | <.0001* |
| Confidence | 0.95 | Prob < t | 1.0000 |

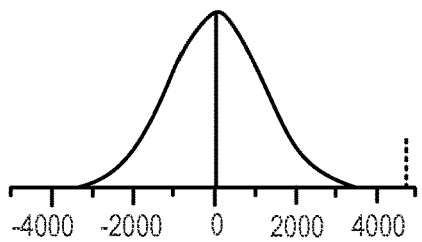

Means Comparisons

Comparisons for each pair using Student's t

Confidence Quantile

| t | Alpha |
|---|---|
| 1.96629 | 0.05 |

LSD Threshold Matrix
Abs(Dif)-LSD

| | Control | L-Carnitine |
|---|---|---|
| Control | -2262.4 | 2495.0 |
| L-Carnitine | 2495.0 | -2180.1 |

Positive values show pairs of means that are significantly different.
Connecting Letters Report

| Level | | Mean |
|---|---|---|
| Control | A | 66995.852 |
| L-Carnitine | B | 62279.153 |

Levels not connected by same letter are significantly different.

FIG. 13C

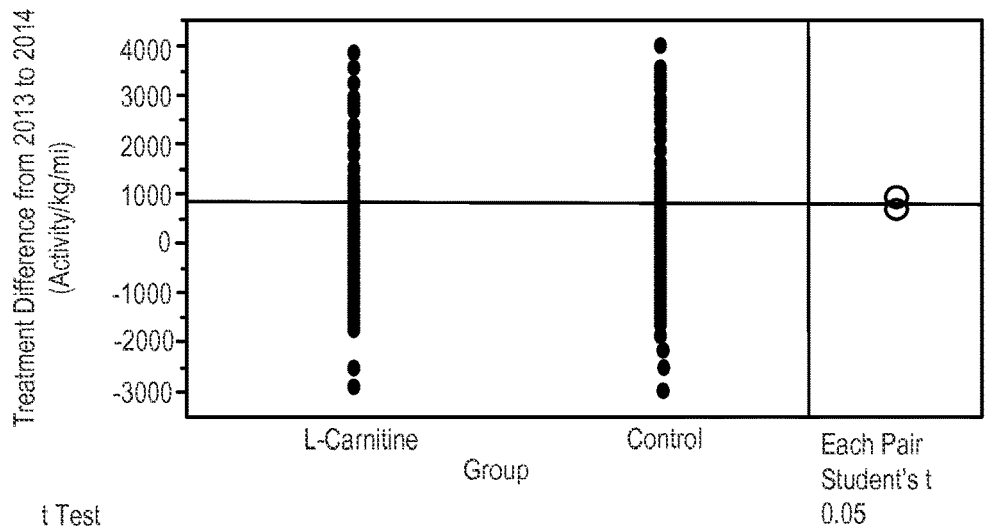

Crossover Comparison – Treatment Difference from Example 1 to Example 2 of APM/kg of Body Weight (Activity/Mile/kg BW)Using a Oneway Analysis Model t Test
Control-L-Carnitine
Assuming unequal variances

| | | | |
|---|---|---|---|
| Difference | -286.23 | t Ratio | -1.97536 |
| Std Err Dif | 144.90 | DF | 469.594 |
| Upper CL Dif | -1.50 | Prob > |t| | 0.0488* |
| Lower CL Dif | -570.96 | Prob > t | 0.9756 |
| Confidence | 0.95 | Prob < t | 0.0244* |

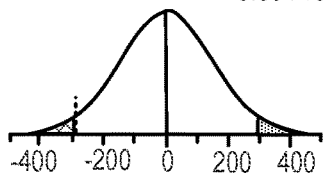

Means Comparisons
Comparisons for each pair using Student's t
Confidence Quantile

| t | Alpha |
|---|---|
| 1.96470 | 0.05 |

LSD Threshold Matrix

| Abs(Dif)-LSD | L-Carnitine | Control |
|---|---|---|
| L-Carnitine | -274.32 | 3.95 |
| Control | 3.95 | -290.01 |

Positive values show pairs of means that are significantly different.
Connecting Letters Report

| Level | | Mean |
|---|---|---|
| L-Carnitine | A | 975.43233 |
| Control | B | 689.20588 |

Levels not connected by same letter are significantly different.

FIG. 15A

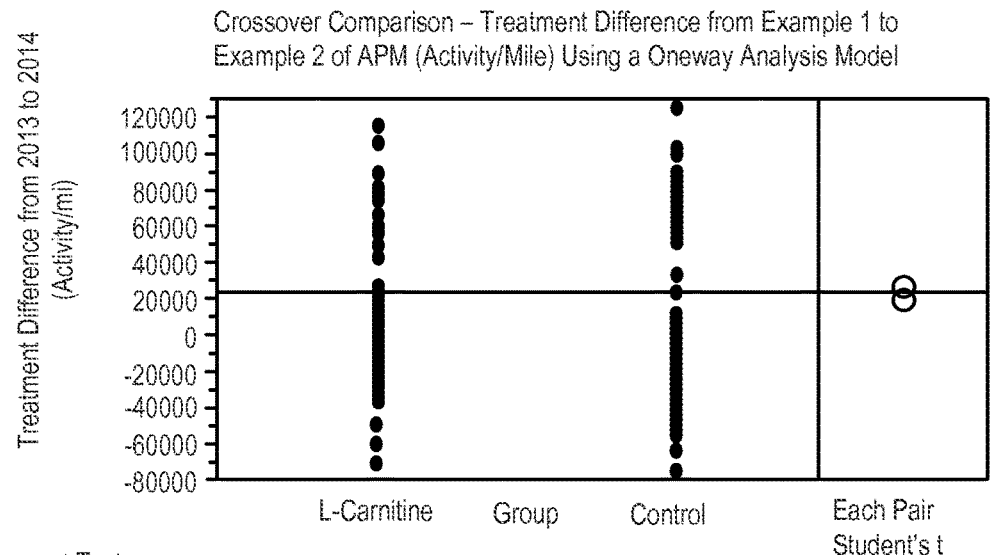

t Test
Control-L-Carnitine
Assuming unequal variances

| | | | |
|---|---|---|---|
| Difference | -8830 | t Ratio | -2.28431 |
| Std Err Dif | 3866 | DF | 470.2283 |
| Upper CL Dif | -1234 | Prob > \|t\| | 0.0228* |
| Lower CL Dif | -16427 | Prob > t | 0.9886 |
| Confidence | 0.95 | Prob < t | 0.0114* |

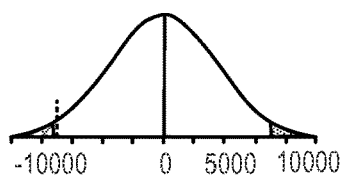

Means Comparisons
Comparisons for each pair using Student's t
Confidence Quantile

| t | Alpha |
|---|---|
| 1.96470 | 0.05 |

LSD Threshold Matrix

| Abs(Dif)-LSD | L-Carnitine | Control |
|---|---|---|
| L-Carnitine | -7319.7 | 1298.6 |
| Control | 1298.6 | -7738.3 |

Positive values show pairs of means that are significantly different.
Connecting Letters Report

| Level | | Mean |
|---|---|---|
| L-Carnitine | A | 27697.496 |
| Control | B | 18867.004 |

Levels not connected by same letter are significantly different.

Total Body Tissue Mass Change for Test Dogs Using a Oneway Analysis of Total Tissue (kg) By Treatment

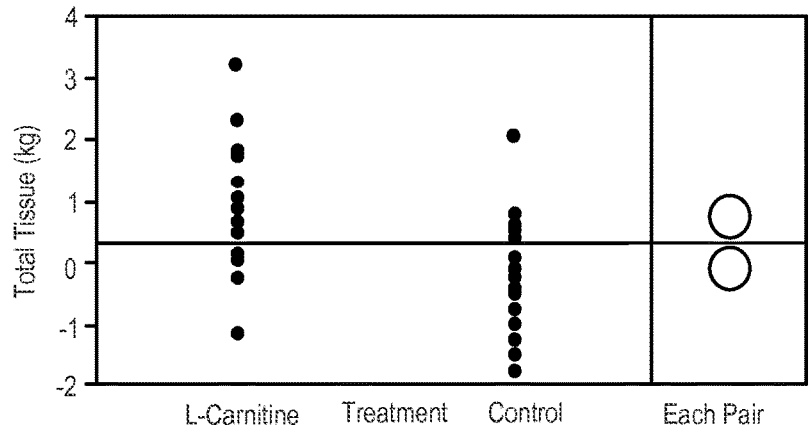

t Test
Control-L-Carnitine
Assuming unequal variances

| | | | |
|---|---|---|---|
| Difference | -0.8579 | t Ratio | -3.64645 |
| Std Err Dif | 0.2353 | DF | 53.92179 |
| Upper CL Dif | -0.3862 | Prob > |t| | 0.0006* |
| Lower CL Dif | -1.3295 | Prob > t | 0.9997 |
| Confidence | 0.95 | Prob < t | 0.0003* |

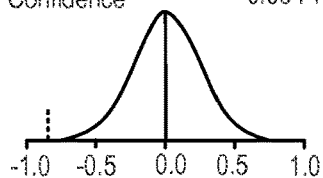

Means Comparisons
Comparisons for each pair using Student's t
Confidence Quantile
    t     Alpha
2.00488  0.05
LSD Threshold Matrix
Abs(Dif)-LSD

| | L-Carnitine | Control |
|---|---|---|
| L-Carnitine | -0.47166 | 0.38619 |
| Control | 0.38619 | -0.47166 |

Positive values show pairs of means that are significantly different.
Connecting Letters Report

| Level | | Mean |
|---|---|---|
| L-Carnitine | A | 0.7414286 |
| Control | B | -0.1164286 |

Levels not connected by same letter are significantly different.

FIG. 24A

Total Body Tissue Mass Change for Female Test Dogs Using a Oneway Analysis of Total Tissue (kg) By Treatment

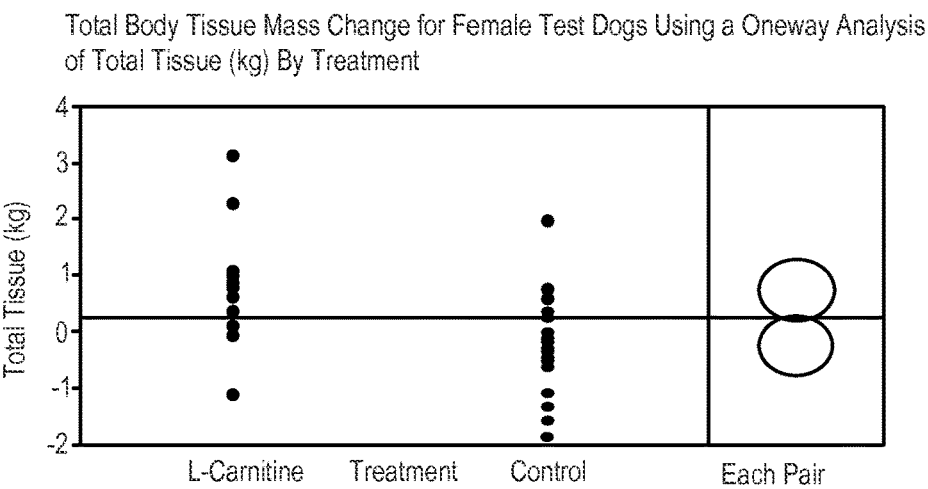

t Test
Control-L-Carnitine
Assuming unequal variances

| | | | |
|---|---|---|---|
| Difference | -1.0033 | t Ratio | -2.71052 |
| Std Err Dif | 0.3701 | DF | 26.73823 |
| Upper CL Dif | -0.2435 | Prob > \|t\| | 0.0116* |
| Lower CL Dif | -1.7631 | Prob > t | 0.9942 |
| Confidence | 0.95 | Prob < t | 0.0058* |

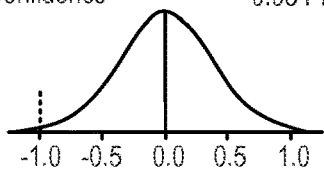

Means Comparisons
Comparisons for each pair using Student's t
Confidence Quantile

| t | Alpha |
|---|---|
| 2.05183 | 0.05 |

LSD Threshold Matrix

| Abs(Dif)-LSD | L-Carnitine | Control |
|---|---|---|
| L-Carnitine | -0.77170 | -0.24455 |
| Control | -0.24455 | -0.74553 |

Positive values show pairs of means that are significantly different.
Connecting Letters Report

| Level | | Mean |
|---|---|---|
| L-Carnitine | A | 0.7792857 |
| Control | B | -0.2240000 |

Levels not connected by same letter are significantly different.

FIG. 24B

Total Body Tissue Mass Change for Male Test Dogs Using a Oneway Analysis of Total Tissue (kg) By Treatment

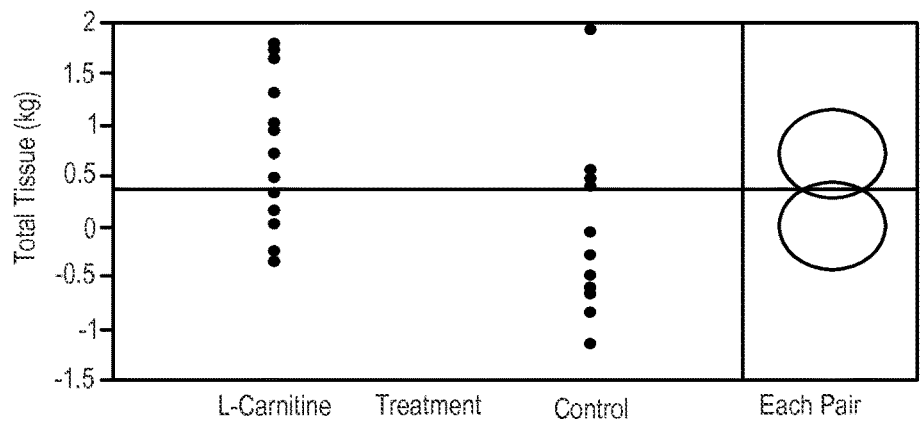

t Test
Control-L-Carnitine
Assuming unequal variances

| Difference | -0.6959 | t Ratio | -2.34692 |
| Std Err Dif | 0.2965 | DF | 24.17675 |
| Upper CL Dif | -0.0842 | Prob > |t| | 0.0274* |
| Lower CL Dif | -1.3076 | Prob > t | 0.9863 |
| Confidence | 0.95 | Prob < t | 0.0137* |

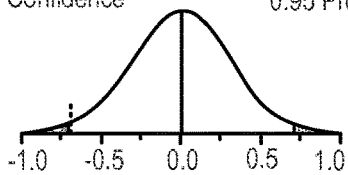

Means Comparisons
Comparisons for each pair using Student's t
Confidence Quantile
    t    Alpha
2.05954    0.05
LSD Threshold Matrix
Abs(Dif)-LSD

|             | L-Carnitine | Control  |
|-------------|-------------|----------|
| L-Carnitine | -0.59677    | 0.08774  |
| Control     | 0.08774     | -0.61930 |

Positive values show pairs of means that are significantly different.
Connecting Letters Report

| Level | | Mean |
|-------|---|------|
| L-Carnitine | A | 0.70357143 |
| Control | B | 0.00769231 |

Levels not connected by same letter are significantly different.

FIG. 24C

Total Lean Mass Change for Male Test Dogs Using a Oneway Analysis of Total Tissue (kg) By Treatment

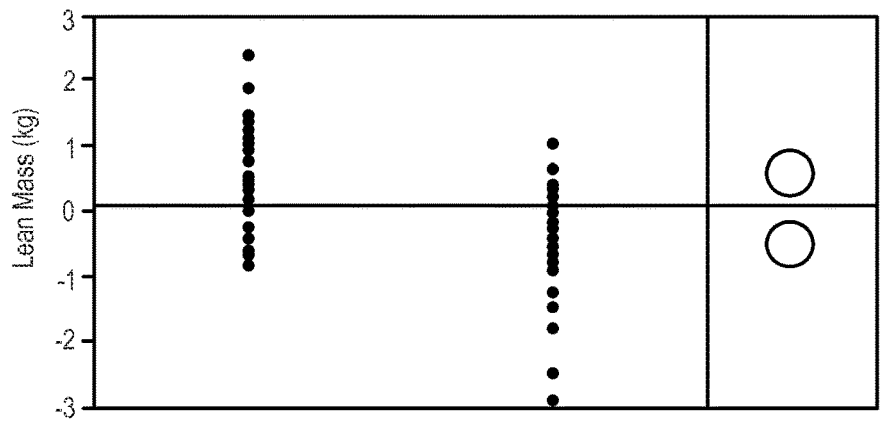

t Test
Control-L-Carnitine
Assuming unequal variances

| | | | |
|---|---|---|---|
| Difference | -1.0893 | t Ratio | -4.64483 |
| Std Err Dif | 0.2345 | DF | 53.3399 |
| Upper CL Dif | -0.6190 | Prob > |t| | <.0001* |
| Lower CL Dif | -1.5596 | Prob > t | 1.0000 |
| Confidence | 0.95 | Prob < t | <.0001* |

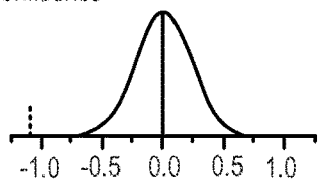

Means Comparisons
Comparisons for each pair using Student's t
Confidence Quantile
      t      Alpha
  2.00488    0.05
LSD Threshold Matrix
Abs(Dif)-LSD

| | L-Carnitine | Control |
|---|---|---|
| L-Carnitine | -0.47018 | 0.61911 |
| Control | 0.61911 | -0.47018 |

Positive values show pairs of means that are significantly different.
Connecting Letters Report

| Level | | Mean |
|---|---|---|
| L-Carnitine | A | 0.6807143 |
| Control | B | -0.4085714 |

Levels not connected by same letter are significantly different.

FIG. 25A

Total Lean Mass Change for Female Test Dogs Using a Oneway Analysis of Total Tissue (kg) By Treatment

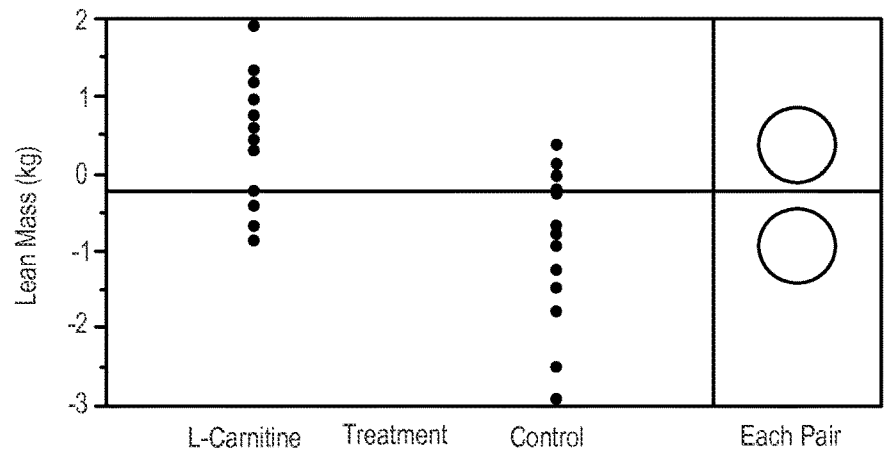

t Test
Control-L-Carnitine
Assuming unequal variances

| | | | |
|---|---|---|---|
| Difference | -1.2894 | t Ratio | -3.90854 |
| Std Err Dif | 0.3299 | DF | 26.29606 |
| Upper CL Dif | -0.6117 | Prob > \|t\| | 0.0006* |
| Lower CL Dif | -1.9672 | Prob > t | 0.9997 |
| Confidence | 0.95 | Prob < t | 0.0003* |

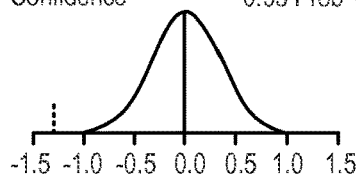

Means Comparisons
Comparisons for each pair using Student's t
Confidence Quantile
  t         Alpha
2.05183     0.05

LSD Threshold Matrix
Abs(Dif)-LSD
               L-Carnitine    Control
L-Carnitine    -0.69424       0.60686
Control         0.60686      -0.67070

Positive values show pairs of means that are significantly different.
Connecting Letters Report
Level              Mean
L-Carnitine   A    0.4514286
Control       B   -0.8380000

Levels not connected by same letter are significantly different.

FIG. 25B

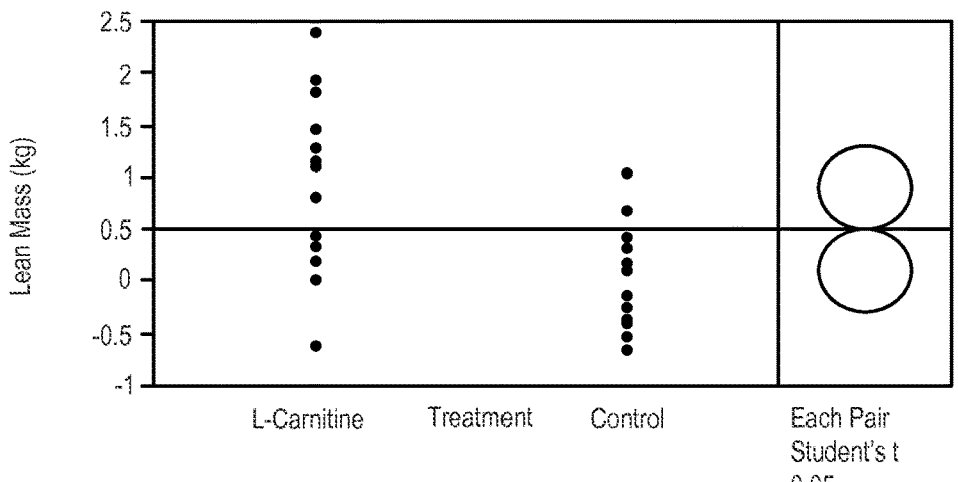

Total Lean Mass Change for Male Test Dogs Using a Oneway Analysis of Total Tissue (kg) By Treatment t Test
Control-L-Carnitine
Assuming unequal variances

| | | | |
|---|---|---|---|
| Difference | -0.8231 | t Ratio | -3.07 |
| Std Err Dif | 0.2681 | DF | 22.27936 |
| Upper CL Dif | -0.2675 | Prob > |t| | 0.0056* |
| Lower CL Dif | -1.3787 | Prob > t | 0.9972 |
| Confidence | 0.95 | Prob < t | 0.0028* |

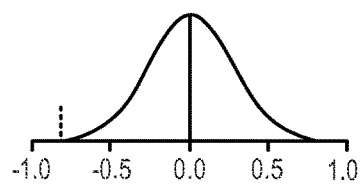

Means Comparisons
Comparisons for each pair using Student's t
Confidence Quantile

```
    t         Alpha
 2.05954      0.05
```

LSD Threshold Matrix
Abs(Dif)-LSD

| | L-Carnitine | Control |
|---|---|---|
| L-Carnitine | -0.55068 | 0.26190 |
| Control | 0.26190 | -0.57147 |

Positive values show pairs of means that are significantly different.
Connecting Letters Report

| Level | | Mean |
|---|---|---|
| L-Carnitine | A | 0.91000000 |
| Control | B | 0.08692308 |

Levels not connected by same letter are significantly different.

FIG. 25C

METHOD FOR DECREASING SKELETAL MUSCLE DAMAGE AND/OR OXIDATIVE STRESS IN MAMMALS

RELATED APPLICATIONS

The present application claims priority to U.S. Provisional Applications Ser. Nos. 62/011,345, filed on Jun. 12, 2014 and 62/147,065, filed on Apr. 14, 2015, which are incorporated herein in their entirety by reference thereto.

BACKGROUND

L-carnitine was first discovered in 1905. Since then, extensive research has demonstrated the important role it plays in helping bodies utilize dietary fat for energy. Without sufficient L-carnitine in the body, humans and animals would not be able to utilize fat effectively and long-term health problems may occur.

In the body, L-carnitine is known to shuttle long-chain fatty acids across the inner-mitochondrial membrane so that the fatty acids can be metabolized and converted into energy. Without L-carnitine, these fatty acids would not be transported and properly utilized.

Mammals can obtain L-carnitine naturally from two sources. First, L-carnitine can be biosynthesized within the body. The body, however, can only produce small amounts of L-carnitine. L-carnitine can also be obtained from foods, such as red meat.

The assignee of the present disclosure markets an L-carnitine and salts thereof as supplements for mammal application. In the past, L-carnitine and derivatives and salts thereof have been administered to mammals. For instance, L-carnitine and derivatives and/or salts thereof can be administered to a mammal when the diet of the mammal is low in L-carnitine. L-carnitine and derivatives and salts thereof have also been administered to mammals in order to prevent obesity. L-carnitine and derivatives and salts thereof have also been marketed to older or senior pets. As mammals increase in age, for instance, the availability of L-carnitine in the body decreases because food intake normally decreases and the body's ability to produce L-carnitine begins to drop. Supplementation with L-carnitine and derivatives and/or salts thereof has shown a positive influence on the aging process.

While L-carnitine supplements have provided great advances in maintaining the health of older mammals, various improvements are still needed. For example, many younger mammals are required or expected to undergo demanding physical activity. For instance, hunting dogs, dogs that race, race horses, farm animals, and the like typically experience demanding exercise. During and after the intense exercise, skeletal muscle damage and/or adverse oxidation may occur, which may require prolonged periods of recovery time after the physical exertion. Consequently, a need exists for a supplement that can decrease skeletal muscle damage and/or decrease oxidative stress after periods of activity in mammals, without having any substantial adverse effects on other body functions. A need also exists for a supplement that can increase performance and activity times without requiring as much food to maintain an ideal body weight/score.

SUMMARY

The present disclosure is generally directed to a method for decreasing skeletal muscle damage and/or oxidative stress during and after physical activity of an active mammal. The present disclosure is also directed to a supplement for increasing performance times without requiring an increase in food intake to maintain an ideal body weight and score. The method of the present disclosure can also increase performance and efficiency. As used herein, an "active mammal" refers to a mammal that undergoes intensive physical activity routinely, such as at least once every 30 days.

In one embodiment, the mammal's body is put into a negative energy balance, such as physical activity or weight loss, and less L-carnitine is produced naturally by the body. Supplementation of L-carnitine can then act to help decrease muscle damage and oxidative stress.

In accordance with the present disclosure, the method comprises the step of administering to a mammal an effective amount of a L-carnitine supplement. Of particular advantage, the L-carnitine supplement can decrease skeletal muscle damage and/or oxidative stress during and after physical activity without the need of administering any other amino acid supplements to the mammal.

The L-carnitine supplement may consist essentially of L-carnitine, meaning the supplement contains no other drugs or dietary supplements. In one embodiment, the L-carnitine supplement consists of L-carnitine. The L-carnitine, for instance, can be biosynthesized from lysine and methionine. L-carnitine may also be manufactured by chemical synthesis methods.

The L-carnitine supplement can be administered to the mammal regularly. For instance, the L-carnitine supplement can be administered to the mammal at least every one to three days, such as daily. Each dose may be from about 5 milligrams to about 10,000 milligrams, such as from about 5 milligrams to about 5,000 milligrams, such as from about 50 milligrams to about 1,000 milligrams. Depending on the mammal, each dose may be from about 1 milligram per kilogram body weight per day to about 50 milligrams per kilogram per day, such as from about 5 milligrams per kilogram per day to about 25 milligrams per kilogram per day. The L-carnitine supplement can be administered orally and can be combined with a food composition.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which:

FIGS. 1, 2, 2A, 2B, 2C, 3, 3A, 3B, 4A, 4B, 5A, 5B, 6, 7, 8, 9, 10A, 10B, 10C, 11A, 11B, 11C, 11D, 12A, 12B, 12C, 13A, 13B, 13C, 14A, 14B, 14C, 14D, 15A, 15B, 16A, 16B, 17A, 17B, 18, 19, 20, 21, 22A, 22B, 23A, 23B, 24A, 24B, 24C, 25A, 25B, and 25C are graphical representations of the results obtained in the example described below.

Figure 1:
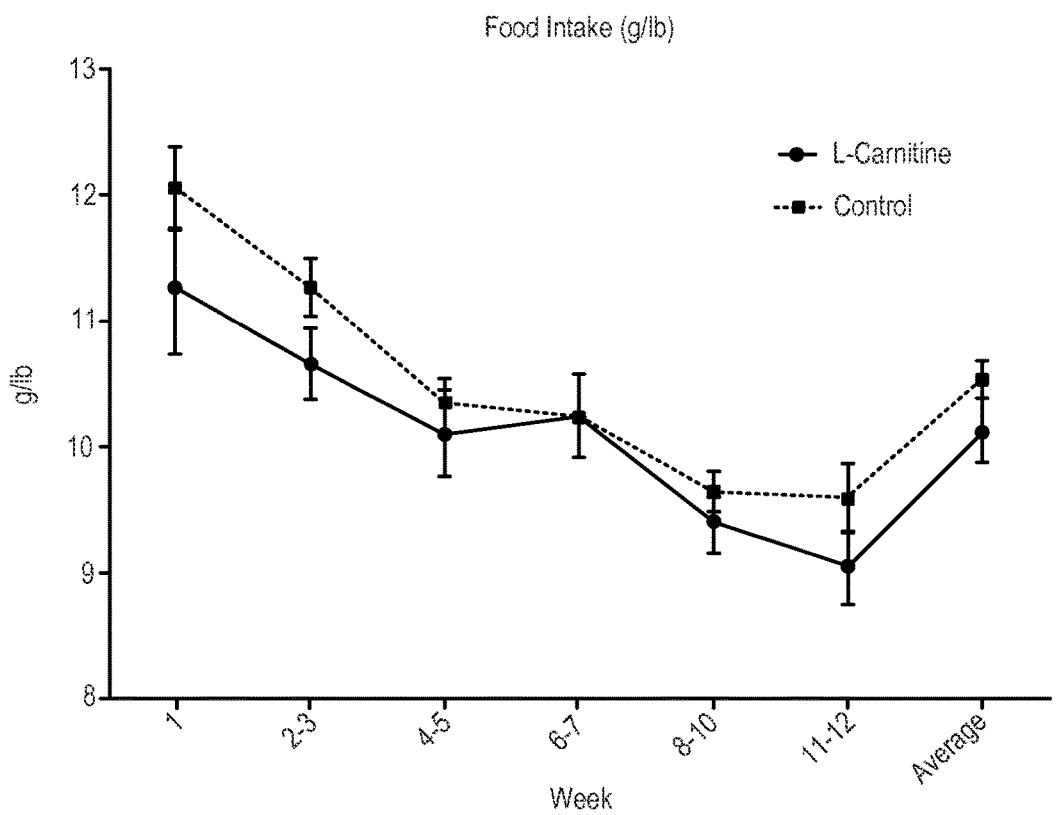

Repeat use of reference characters in the present specification and drawings is intended to represent the same or analogous features or elements of the present invention.

Definitions

The term "intensive physical activity" means activity that lasts at least 20 minutes and where the heart rate increase is generally between 5% and 150% or more of the resting heart rate.

In one embodiment, "intensive physical activity" can mean a negative energy balance in the mammal, such as physical activity, weight loss, diets, aging, gestation, and lactation.

The term "intensive physical activity" can also mean the activity of a mammal during gestation or during the act of giving birth. In one embodiment, a L-carnitine supplement could be administered to a mammal in preparation of a the mammal giving birth.

The term "L-carnitine supplement" may contain L-carnitine and derivatives and/or salts thereof. L-carnitine supplements can include L-carnitine base or derivatives and/or salts thereof including acetyl L-carnitine, valeryl L-carnitine, isovaleryl L-carnitine, benzyl L-carnitine, L-leucyl L-carnitine, L-valyl L-carnitine, other L-amino acyl carnitines, salts of L-amino acyl L-carnitine, L-carnitine HCL, L-carnitine L-tartrate, L-carnitine fumarate, propionylL-carnitine, L-carnitine phosphate, acetyl L-carnitine L-aspartate, acetyl L-carnitine citrate, acetyl L-carnitine maleate, acetyl L-carnitine phosphate, acetyl L-carnitine fumarate, propionyl L-carnitine orotate, acetyl L-carnitine orotate, butyryl L-carnitine orotate, propionyl L-carnitine fumarate, L-carnitine oxalate, L-carnitine sulfate, GPLC glycine propionyl L-carnitine, and the like.

The term "mammal" includes any mammal that may experience skeletal muscle damage and/or oxidative stress during and after physical activity and includes canine, equine, feline, bovine, ovine, human, or porcine mammals.

The phrase "effective amount" means an amount of a compound that promotes, improves, stimulates, or encourages a response to the particular condition or disorder or the particular symptom of the condition or disorder.

The term "supplement" means a product in addition to the normal diet of the mammal but may be combined with a mammal's normal food or drink composition. The supplement may be in any form but not limited to a solid, liquid, gel, capsule, or powder. A supplement may also be administered simultaneously with or as a component of a food composition which may comprise a food product, a beverage, a pet food, a snack, or a treat. In one embodiment, the beverage may be an activity drink.

DETAILED DESCRIPTION

It is to be understood by one of ordinary skill in the art that the present discussion is a description of exemplary embodiments only, and is not intended as limiting the broader aspects of the present disclosure.

Energy production in mammals occurs in the mitochondria. Mitochondria are responsible for the production of ATP and are present in relatively high numbers in essentially all cells in the body.

During intense physical activity, muscle cells have tremendous energy needs. This energy can come from the mitochondria in the form of ATP. The mitochondria can produce ATP, for instance, by breaking down fatty acids and glucose obtained from food sources. ATP is produced in the mitochondria through an aerobic metabolic process.

During intense physical activity, greater amounts of oxygen are required in order to fuel the aerobic metabolic process and produce sufficient amounts of ATP for the muscles. When oxygen supplies dwindle, however, the cells can generate energy anaerobically causing lactic acid to be generated.

During intense physical activity, muscle cells can become damaged which causes the release of various constituents into the bloodstream. If these compounds reach high levels, they can possibly damage the kidneys and/or the liver. These compounds can include creatine kinase and myoglobin. Strenuous physical activity can also impose oxidative stress on the body due to oxygen free radical generation. During oxidative stress, lipid peroxidation in various tissues can occur. One biomarker that may be used to indicate an increase in oxidative stress is demonstrated by an increase in serum thiobarbituric acid reactive substances (TBARS) in the blood. If oxidative stress is not terminated, the condition can lead to the breakdown of cell membranes.

In one embodiment, the mammal may be in a negative energy balance, including physical activity or weight loss, wherein the body naturally produces less L-carnitine. During said negative energy balance, muscle damage and oxidative stress can be reduced by supplementation of L-carnitine.

After periods of intense physical activity, muscle damage and/or oxidative stress can result in soreness and possible muscle injury. The present disclosure is directed to a method for preventing muscle injury and/or oxidative stress in active mammals that periodically undergo intense physical activity. As will be explained below, the present disclosure is generally directed to administering to a mammal an effective amount of a dietary supplement that decreases skeletal muscle damage and/or oxidative stress during and after physical activity.

In one embodiment, the dietary supplement comprises L-carnitine. It was discovered that administering L-carnitine to a mammal undergoing intense physical activity can decrease skeletal muscle breakdown and/or decrease oxidative stress while also improving food conversion, decreasing muscle recovery time, and increasing fat utilization as fuel. Of particular advantage, the above results can be achieved without having to administer other dietary supplements, such as amino acids. In addition, the dietary supplement of the present disclosure produces no noticeable side effects. For instance, administering the dietary supplement regularly can be done without showing any significant change in lean mass, total mass, percent fat, or bone mass.

As stated above, the dietary supplement comprises L-carnitine. L-carnitine is a quaternary amine that can be biosynthesized from lysine and methionine. L-carnitine is known to promote beta-oxidation of long-chain fatty acids by facilitating their transfer across the mitochondrial membrane. L-carnitine supplements have then been provided to mammals in the past, especially aged pets and mammals, that may have a diet-induced L-carnitine deficiency.

L-carnitine has now been discovered to prevent or inhibit muscle damage and/or oxidative stress during physical activity in order to minimize recovery time needed after the activity.

In order to decrease skeletal muscle damage and/or oxidative stress during and after physical activity, the present disclosure is directed to a method of administering to an active mammal an effective amount of an L-carnitine supplement. The above advantages and benefits may be realized without any adverse consequences. In addition, in one embodiment, the mammal may experience no substantial difference in lean mass, total mass, percent fat, or bone mass.

The L-carnitine supplement can be administered regularly, such as at least two to four times a week. For instance, the L-carnitine supplement may be administered to the mammal at least every one to three days. In one particular embodiment, the L-carnitine supplement is administered daily. The dosage can be from about 5 to 10,000 milligrams per day, such as from about 5 to about 5,000 milligrams per day, such as from about 50 milligrams to about 1000 milligrams per day. The dosage, for instance, can be greater than about 100 milligrams per day, such as greater than about 150 milligrams per day, such as greater than about 200 milligrams per day, such as greater than about 250 milligrams per day. Based on body mass, the dosage can be from about 1 milligram per kilogram of body weight per day to about 100 milligrams per kilogram body weight per day. For example, the dosage may be from about 5 milligrams per kilogram body weight per day to about 50 milligrams per kilogram body weight per day. In one particular embodiment, the dosage can be from about 5 milligrams per kilogram body weight per day to about 25 milligrams per kilogram body weight per day. In another particular embodiment, the dosage can be greater than about 1.5 milligrams per kilogram body weight per day, greater than about 1.8 milligrams per kilogram body weight per day, greater than about 2.0 milligrams per kilogram body weight per day, greater than about 2.2 milligrams per kilogram body weight per day, greater than about 2.4 milligrams per kilogram body weight per day, greater than about 2.6 milligrams per kilogram body weight per day, greater than about 2.8 milligrams per kilogram body weight per day, or greater than about 3.0 milligrams per kilogram body weight per day.

The L-carnitine supplement can be administered to the mammal in any suitable form using any suitable administration route. For example, the L-carnitine supplement can be administered orally alone, in combination with a food composition, or as part of a food composition. The L-carnitine supplement may also be part of a dietary supplement or as a nutraceutical composition. The L-carnitine supplement, in one embodiment, may only contain L-carnitine to receive the benefits and advantages of the present disclosure without containing other dietary supplements, such as amino acid supplements.

In addition to being administered orally, the L-carnitine dose can also be administered using other routes including intranasal, intravenous, intramuscular, intragastric, and the like.

When the carnitine supplement is combined with a food or beverage composition, the food or beverage composition may comprise any suitable composition for consumption by the mammal. Such compositions include complete foods or beverages intended to supply the necessary dietary requirements for mammal or food supplements such as treats and snacks. The food composition may comprise pellets, a drink, a bar, a prepared food contained in a can, a dairy food product, or any other functional food composition The food composition may also comprise any form of a supplement such as a pill, soft gel, gummy figurine, wafer, or the like.

The food composition ingested by the mammal in addition to the L-carnitine supplement may also be rich in L-carnitine. The L-carnitine supplement of the present disclosure, for instance, is intended to provide additional L-carnitine in addition to normal amounts of L-carnitine contained in a standard diet and/or the amount of L-carnitine produced by the body.

In this regard, the food composition may comprise from about 5% to about 50% of protein. The protein source may be vegetable such as soy bean meal or may be an animal protein such as meat protein. Examples of meat protein include beef, pork, lamb, poultry, fish and the like.

The food composition may further comprise from about 5% to about 40% fat. The fat may comprise animal fats and/or vegetable fats. The food composition may further comprise a carbohydrate. The carbohydrate may be present in an amount greater than about 10% by weight. The carbohydrate may be obtained from grains and cereals.

The active mammal treated in accordance with the present disclosure can comprise any suitable mammal. For instance, the mammal may be canine or equine. The L-carnitine supplement can be fed to an active mammal of any age such as from parturition through the adult life in the mammal. In various embodiments the mammal may be a dog, a cat, a horse, or a human. In many embodiments, the mammal can be from an adolescent or young adult to an adult. For instance, the active mammal may have an age that is at least 5%, such as least 10%, such as least 15%, such as least 20%, such as least 25%, such as least 30% of its expected life span. The mammal may have an age such that it is less than about 80%, such as less than about 75%, such as less than about 70%, such as less than about 65% of its expected life span. A determination of life span may be based on actuarial tables, calculations, or the like.

The L-carnitine supplement may be administered to the mammal in accordance to the present disclosure as long as the mammal remains active on a regular routine basis. The L-carnitine supplement is administered in an amount sufficient to decrease skeletal muscle damage during and after physical activity, reduce oxidative stress during or after physical activity, or decrease both skeletal muscle damage and oxidative stress. Skeletal muscle damage, in one embodiment, can be determined by monitoring the biomarker, myoglobin, in the blood stream. Specifically, myoglobin values can be taken and recorded 24 hours before physical activity and 24 hours after physical activity. For a mammal treated in accordance with the present disclosure, the myoglobin values before and after physical activity may not vary by more than 300%, such as by not more than 250%, such as by not more than 200%.

In one embodiment, mammals treated in accordance with the present disclosure may have myoglobin values after physical activity that are at least 50%, such as at least 75%, such as at least 100%, such as at least 125%, such as at least 150% less than the same mammal that is not administered the L-carnitine supplement.

In addition to lowering skeletal muscle damage, the L-carnitine supplement can also reduce oxidative stress. In particular, the L-carnitine supplement can reduce peroxidation of membranes due to physical stress. Oxidative stress can be measured by monitoring thiobarbituric acid reactive substances in the blood stream. Comparative measurements can be taken 24 hours prior to physical activity and 24 hours after physical activity.

In one embodiment, mammals treated in accordance with the present disclosure may have levels of TBARS after physical activity that are at least 50%, such as at least 75%, such as at least 100%, such as at least 125%, such as at least 125% less than the same mammal that is not administered the L-carnitine supplement.

The L-carnitine supplement of the present disclosure can also lower creatine kinase present in the bloodstream after physical activity. In one embodiment, mammals treated in accordance with the present disclosure may have creatine kinase values after physical activity that are at least 5%, such as at least 8%, such as at least 10%, such as at least 12% less than the same mammal that is not administered the L-carnitine supplement The present disclosure may be better understood with reference to the following examples.

EXAMPLE 1

A 90 day study was conducted to show that L-carnitine can decrease skeletal muscle breakdown, improve food conversion, decrease oxidative stress, decrease muscle recovery time and increase fat utilization as fuel during intense exercise in performance mammals, namely dogs.

In the following example, the performance dogs were administered an L-carnitine supplement obtained from Lonza, Inc. under the trade name CARNIKING.

Forty Labrador Retrievers were divided into two equal groups of twenty (11 males, 9 females) based on gender, body weight ("BW"), genetics, and lean mass and fed a low L-carnitine basal diet for a 90 day feeding period. The experimental dogs were fed the low L-carnitine basal for 10 days prior to the start of the study. Twenty of the Labs received 250 mg/day of L-carnitine (batch D22312) and 3.75 g of sugar and twenty of the Labs received 4 g/d of sugar. The dogs were scanned with a GE Prodigy DEXA system immediately prior to beginning of the study and the determined lean mass was utilized as a key component for helping assort the dogs equally between the control and L-carnitine group. A serum sample was obtained from each dog to determine a baseline value for blood biomarkers that were used to evaluate muscle damage and antioxidant status. The L-carnitine and control performance dogs were put through a weekly running program consisting of running sprint type shorter runs of higher intensity twice weekly (1200 yds/session increasing to 2400 yds/session over 10 wk period) and running endurance longer runs one time per wk (increasing from 5 miles/session to 10 miles per session over a 10 wk period).

Each test dog wore an Actical activity monitor from Philips Respironics on a collar for the short higher intensity runs and also wore an Actical activity monitor for the weekly longer endurance runs. The activity data was downloaded into spread sheets along with each dogs identity. Twenty four hours after each long run during the 13 wk running program each of the dogs were scored by kennel staff for soreness or any type of lameness The exercise program was decreased in a tapering program during wk 11 and 12 to allow the dogs to rest for the final long run completed on wk 13. Pre-run serum samples from each test dog was taken 24 hr before the last endurance run. The heart rate and basal body temperature was determined for each test dog prior to the last long endurance run.

Each performance dog also wore the Actical activity monitor during the last endurance run. The dogs were put through a 15 mile run that included mud, water, tall grass, and swimming. The dogs were timed when they completed the course. The dogs were encouraged by kennel staff that rode along in a 4 wheel all terrain type vehicle during all of the endurance runs. The dogs were free and could run significantly more than the prescribed distance but all dogs ran at least the stated mileage. Dogs that did not complete the course were eliminated from the data set. Immediately following the 15 mile endurance run, each dog was placed in a kennel and evaluated for recovery time for body temperature (every 15 minutes for 2 hr) and heart rate (every 2 minutes for 14 minutes). Twenty four hours after test dogs ran the last 15 endurance run, post-run serum samples were taken to evaluate biomarkers for muscle damage and antioxidant status. Each test dog was also scanned with the GE Prodigy DEXA to determine body composition change that occurred during the course of the 13 wk study.

Both sexes of dogs receiving L-carnitine ran an average of 6.56 minutes faster (p=0.0028) over a 15-mile timed run at the end of the study with the L-carnitine fed males running 8.69 minutes faster (p=0.0004) than control males. The dogs that were fed L-carnitine produced a significantly (p<0.05) higher 1317 Actical units/mile/lb BW for the average 13 weekly long endurance runs when compared to 1135 units for the control group. The female L-carnitine dogs had an average activity of 1509 units that was significantly higher than 1258 units for control females and both groups of males.

The interesting component for the long run activity units was the significant decrease in activity/mile/lb BW as affected by time and distance for both treatment groups. The L-carnitine dogs also had a significantly (p<0.05) higher activity of 1451 Actical units/mile/lb BW average for the short runs compared to 1255 units for the control dogs during the 13 wk period. The female L-carnitine dogs averaged 1522 activity units for weekly short runs and had significantly higher (p<0.05) activity than 1160 units for the control males.

Both groups gained weight concomitant with an increase in percentage fat and bone mass over the duration of the study. The L-carnitine dogs had a numerical smaller increase in % fat mass (p=0.25) from the beginning of study to the end and the female L-carnitine dogs showed a numerical lower increase in % fat mass (4.2% vs 8.9%)(p=0.22) compared to control females. No increase in lean mass was detected in either group, and the gains in total mass, percentage fat, and bone mass were not considered significantly different between groups.

The increase in myoglobin values after exercise was considered significant (p<0.0001)), with the control group having significantly elevated 30.97 ng/mL serum myoglobin values compared to the 19.67 ng/mL for L-carnitine dogs. The change in myoglobin between control dogs post-run compared to pre-run was 24.92 ng/mL indicating significant muscle damage during the last run.

Total antioxidant capacity of serum significantly increased for both groups during the course of training but the antioxidant capacity values were decreased for both groups after the 15 mile long run (p<0.0001). However, no significant difference was found between groups at any of the timepoints. Thiobarbituric acid reactive substances (TBARS) of serum were unchanged throughout the study. TBARS differences between the pre-run blood and the post-run blood for the individual dogs showed that TBARS increased 2.14 units for the control dogs (P=0.155) whereas the L-carnitine dogs only had an increase of 0.41 units.

Creatine kinase values increased 13.64 units following the long run compared to the pre-run for the control dogs and the units only increased 9.3 for L-carnitine dogs for same time period but the difference was not significantly different (p=0.155).

Each dog was observed 24 hr following each of the long runs to evaluate. The dogs were scored for soreness and lameness. There were no noticeable effects of the long runs on lameness or soreness for either treatment. Each group consumed similar amounts of energy and nutrients throughout the duration of the study. No significant differences in food intake between treatments (g/kg BW or kcal ME/kg BW) was observed. However the L-carnitine group tended to consume less food per kg BW basis especially early and late in the performance study. The food consumption decreased per kg BW for both groups as the study progressed primarily because of improved fitness of dogs and increasing environmental temperatures.

Experimental Design: Forty Labrador Retrievers (labs) ranging in age from 1 to 3.5 years were incorporated into a two dietary treatment study. The two dietary treatments were based on feeding the test dogs the same low L-carnitine diet but adding 250 mg per day of L-carnitine to the L-carnitine group. Each of the L-carnitine dogs received the daily 250 mg of L-carnitine mixed with an additional 3.75 g sugar. The control dogs received 4 g of sugar each day. Twenty labs of equal gender, age, excitement level, frame size, body weight and genetic background were utilized for each of the two treatments. The labs utilized for the nutrition study were from a minimum of 6 different bitches. The lean body mass of the 40 test dogs was determined by scanning with the DEXA and the final key component utilized to assure equal groups. Prior to the start of the study, the labs were acclimated to the experimental diets for a minimum of 10 days. The labs were weighed at the beginning of the 90 day study and weighed every two weeks throughout the study. Feed consumption was determined daily by weighing feed provided and feed refusals. The quantity of food provided each dog on a daily basis was adjusted based on maintaining a minimum initial starting body weight throughout the study. The dog food was provided by Lonza Inc. and was equal to the minimum guaranteed analysis of Gold N Pro (MFA of Missouri) that the performance dogs had been consuming prior to the start of the study (Table 1).

Exercise Regimen: Each group of dogs were put through two different types of exercise programs on a weekly basis. The exercise regimen consisted of both sprint (short runs) and endurance (long runs) type work during the 90 day period. Each group of dogs were put through a simulated amount of work that would be equal to competing in an AKC Junior Hunt Test (American Kennel Club) and also once a week the dogs were put through a simulated endurance run. Each group of test dogs ran the AKC Hunt Test workout 26 times during the 13 wk study which was 2 times per week. During each week, each group ran the test 2 times with 1 day rest between runs.

The AKC Hunt Test workout during the initial week amounted to two days of 6 consecutive sprint type retrieves for a minimum of 100 yd each way making a total of 1200 yd per day or 2400 yd per wk. The dogs brought back a bumper (equivalent to a duck or mark) to the handler during the exercise. The number and length of the sprint type exercises were gradually increased over a 10 wk period to 10 marks that were 120 yd each way making a total of 2400 yd/d and 4800 yd/wk to match the improved athletic fitness and work efficiency of the test dogs. The length of time involved in the intense exercise simulating the AKC Hunt Test was approximately 10 to 15 minutes per dog each of the short run days and was equal for both treatments. The rest time between retrieves (sprints) in a set during the simulated weekly AKC Hunt Test was equal for all dogs.

The distance and number of sprints affiliated with the short runs (marks) were decreased during wk 11 back to 1200 total yd/d or 2400 yd/wk and decreased again on wk 12 to 600 yd/d or a total of 1200 yd/wk to provide rest for the final long run on wk 13. The weekly endurance run was 5 miles in the beginning, increased by ½ mile per wk and was increased to a distance of 10 miles on the $10^{th}$ week. The dogs ran only a 5 mile endurance run on wk 11 and only a 2 mile endurance run on wk 12 in order to rest for the final long run during the $13^{th}$ wk. The endurance (long) runs for the 40 dogs were carried out on the $5^{th}$ and $6^{th}$ day of each wk for both treatments. Half of the dogs were run on Friday ($5^{th}$ d) and half of the dogs were run on the Saturday ($6^{th}$ d). The exercise regimen was finalized during the $13^{th}$ week of the study by resting the dogs for 3 days and then running half of the dogs from each group for a 15 mile endurance run on Monday and the remaining 20 dogs were run the 15 mile endurance run on Tuesday. The longer endurance type runs were slightly slower to enhance fat oxidation and represent an exercise intensity equivalent to 50%-65% VO2 max.

Body Scans: Each dog was scanned for body composition with a GE Prodigy Pro Fan beam instrument during the week prior to the beginning of the 90 day study and the first working day following the last endurance run. Body composition values were determined for % lean mass, % fat mass, and % bone ash for each dog. The difference in body composition was determined by comparing the beginning scan and last scan for each test dog. The final scans were completed 24 hr post run.

Blood Analysis: Serum samples were taken at three different times from each dog during the 90 day period. The blood samples were collected as follows: 1.) just prior to scanning each dog for body composition at the beginning of the study, 2.) prior to the long run on the $13^{th}$ week, and 3.) following the long run on the $13^{th}$ week. The serum samples were analyzed for Phosphocreatine Kinase and Canine Myoglobin to determine the amount of muscle protein leakage that occurred following the long run and TBARS and Total Antioxidant Capacity (TAC) were determined to evaluate the antioxidant status of each of the test dogs during the exercise program. The final blood sample was taken 24 hr after the long run to obtain maximum protein leakage based on previous similar types of exercise research with human athletes.

Performance and Recovery Time: An Actical monitor (Philips Respironics) was worn around the neck of each dog on a collar and utilized to evaluate the amount of movement (measured total movements and intensity) for each dog for the purpose of evaluating equal work between treatments and also to evaluate the individual work intensity while completing the daily retrieves. Each dog wore the Actical monitor for each long run and wore the Actical monitor for the final 15 mile run. The Actical monitor data was downloaded to a computer for evaluation.

The dogs were timed during the last 15 mile run at the end of the study. The body temperature and heart rate for each dog was determined just prior to the long 15 mile run. The heart rate measurements were determined manually and body temperature was determined by using a rectal thermometer. Each staff member was responsible for determining the time required to complete the run for one of the test dogs in each set. Each staff member was also responsible for determining the heart rate and body temperature of their specific assigned dog immediately upon their return after the run. The heart rate was determined every 2 minutes for a fourteen minute period following the last long run and the body temperature was determined every 15 minute for a two hour period after completing the long run. The heart rate and body temperature was determined both before and after to evaluate the fitness and time required after run to reach basal HR and body temperatures.

A subjective recovery score was determined 24 hours after endurance run for each test dog once per week. The subjective recovery score (1-5; score of 1 for no soreness or stiffness in limbs and a score of 5 meant major soreness and stiffness) was based on ease of movement and soreness of each dog. The same subjective system was used 6 hr after the long 15 mile run and again at 24 and 48 hr to evaluate the recovery of the dogs as far as soreness and desire to move.

Biomarkers and Assay Methods: Blood was drawn from each dog using a serum separator tube at three different times during the 90 day period: 1.) just prior to scanning each dog for body composition at the beginning of the study, 2.) prior to the long run on the 13th week, and 3.) following the long run on the 13th week. The final blood sample was taken 24 hr after the long run to obtain maximum protein leakage based on previous similar types of exercise research with human athletes. Each time after the blood was drawn it was allowed to clot before being centrifuged for 15 min at 2000 g at 4° C. Serum was aliquoted into 1.5 mL microcentrifuge tubes and stored at −80° C. until assays were ran following the end of the study.

Creatine kinase (CK) and canine myoglobin were measured to determine the amount of muscle protein leakage that occurred following the long run. Thiobarbituric acid reactive substances (TBARS) and total antioxidant capacity (TAC) were measured to evaluate the antioxidant status of each of the test dogs during the exercise program. Serum samples were analyzed for total antioxidant capacity (TAC) and thiobarbituric acid reactive substances (TBARS) using commercially available colorimetric kits supplied by Cayman Chemical Company (Ann Arbor, Mich.) per manufacturer instructions. Serum canine myoglobin levels were determined using a commercially available ELISA supplied by Innovate Research (Novi, Mich.) per manufacturer instructions. Creatine kinase activity was determined colorimetrically using a commercially available kit supplied by BioVision (San Francisco, Calif.).

Metabolizable Energy Determination: The ME for the low L-carnitine test diet was determined by using the indicator method 2 (AAFCO, 2007). Each of the test dogs were given 500 g daily of the low L-carnitine test diet for a 5 day pre-collection period and given the same amount of the test diet to each dog for a 4 day collection period. Two g of titanium dioxide was given each test dogs by gelatin capsule at the same time as providing 500 g of test food during the collection period. The titanium marker was 0.4% of the test food consumed. Aliquots of feces from each test dog was collected each day during a 4 day collection period and maintained as 4 individual samples. The fecal samples were frozen immediately after collection. Each fecal sample was freeze dried and analyzed for crude protein and gross energy (Parr Bomb calorimeter). Titanium was determined in excreta using the modified method of Myers et al. (2004).

Statistical Methods: GraphPad Prism 6.0 was used to compare means between groups for run time, food intake, body weight, and changes in blood chemistry using an unpaired t-test. Results were considered significant if a p-value of 0.05 was obtained. JMP 10.0.2 was used to create a mixed model for long runs, short runs, body composition, and blood chemistry.

Results: Table 1 shows the basal diet that was fed to the dogs during the study. The ME and DE (digestible energy) of the diet was determined to be 3969 kcal ME/kg and 4214 kcal DE/kg. The food was fed for a 10 day pre-study period to make sure the dogs would be acclimated to the new food at the beginning of the study.

TABLE 1

Low L-carnitine basal fed to all test dogs.

| Step 1: Kibble Ingredients | Base Percent |
|---|---|
| Corn, ground | 42.8550 |
| Chicken meal | 29.0000 |
| Wheat, ground | 12.8000 |
| Rice, brewer's | 5.5000 |
| Beet pulp | 5.5000 |
| Egg, dried | 1.1100 |
| Flaxseed | 1.1100 |
| Salt, plain | 0.5900 |
| Potassium Chloride | 0.5500 |
| Mixed tocopherols | 0.2200 |
| L-Lysine | 0.2180 |
| DL-Methionine | 0.1920 |
| 2011-No K-CNS Dog & Cat Vitamin Premix | 0.1330 |
| 2011-01 CNS Dog & Cat Mineral Premix | 0.1110 |
| Choline chloride 60% | 0.1110 |
| L-Carnitine | 0.0000 |
| Totals | 100.0000 |

| Step 2: Kibble Coating | Formula Percent |
|---|---|
| Extruded kibble | 89.5045 |
| Poultry fat (preserved w. mixed tocopherols) | 10.4955 |

| Guarantees | |
|---|---|
| Crude protein, min % | 23.30 |
| Crude fat, min % | 16.00 |
| Crude fiber, max % | 4.00 |
| Moisture, max % | 10.00 |

| Proximate Analysis | As Received | Dry Weight |
|---|---|---|
| Moisture | 6.64 | ///// |
| Dry Matter | 93.36 | ///// |
| Protein (crude) | 26.8 | 28.7 |
| Fat (acid hydrolysis) | 15.3 | 16.4 |
| Fiber (crude) | 2.99 | 3.2 |
| Ash | 4.80 | 5.14 |

| Model specification | | |
|---|---|---|
| | Response Variables | Fixed Effects |
| Long Runs | APM/lb | ID (Random); Treatment (L-carnitine, Control); Sex (Male, Female); Week (1-13); Distance (5.5, 7, 6.5, 7, 7.5, 8, 8.5, 9, 9.5, 10, 5, 15 miles); Treatment * Sex; Treatment * Week; Treatment * Distance. |
| Short Runs | APM/lb | ID (Random); Treatment (L-carnitine, Control); Sex (Male, Female); Week (3-13); Distance (1.6364, 1.7727, 1.9091, 2.0455, 2.1818, 2.3182, 2.4545, 2.5909, 2.7273, 1.3636, 0.6818 miles); Treatment * Sex; Treatment * Week; Treatment * Distance. |
| Body Composition | Total Mass (lbs); Lean Mass (lbs); % Fat; Bone Mineral Content (g) | ID (Random); Treatment (L-carnitine, Control); Sex (Male, Female); Time (Initial, Final); Treatment * Time; Treatment * Sex |
| Blood Chemistry | Creatine Kinase (mU/mL); Myoglobin (ng/mL); TBARS (μM MDA); TAC (mM Trolox Equiv) | ID (Random), Treatment (L-carnitine, Control); Sex (Male, Female); Time (Baseline, Pre-Run, Post-Run); Treatment * Time; Treatment * Sex |

TABLE 1-continued

| | | |
|---|---|---|
| Metabolizable Energy | 3969 Kcal/Kg | |
| Digestible Energy | 4214 Kcal/Kg | |

L-carnitine basal fed to all test dogs.

| Nutrient Name | Unit | 92.0% DM Amount | 100% DM Amount | 100% DM AAFCO |
|---|---|---|---|---|
| Dry Matter | % | 92.00 | | |
| Moisture | % | 8.00 | | |
| Crude Protein | % | 23.30 | 25.33 | 22.00 |
| Crude Fat | % | 16.20 | 17.61 | 8.00 |
| Crude Fiber | % | 2.57 | 2.79 | |
| Calcium | % | 1.26 | 1.37 | 1.00 |
| Phopshorus | % | 0.89 | 0.96 | 0.80 |
| Ash | % | 6.04 | 6.57 | |
| Methionine | % | 0.54 | 0.59 | 0.53 |
| Lysine | % | 0.98 | 1.07 | 0.77 |
| L-Carnitine | % | 0.00 | 0.00 | |
| Sodium | % | 0.33 | 0.36 | 0.30 |
| Potassium | % | 0.64 | 0.70 | 0.60 |
| Magnesium | % | 0.12 | 0.13 | 0.04 |
| Iron | ppm | 263.45 | 286.35 | 80.00 |
| Copper | ppm | 20.94 | 22.76 | 7.30 |
| Zinc | ppm | 233.44 | 253.74 | 120.00 |
| Linoleic Acid | % | 3.82 | 4.15 | 1.00 |
| Omega 6 Fatty Acids | % | 3.51 | 3.82 | |
| Omega 3 Fatty Acids | % | 0.38 | 0.41 | |

Table 2 shows the time required for the performance dogs to complete the 15 mile final run. The run time was significantly less (p=0.0028) at 95.84 minutes for combined male and female L-carnitine dogs compared to 102.4 minutes for the control dogs of both genders. The male L-carnitine fed dogs ran significantly faster times (p=0.0004) for the 15 mile run compared to the control males. The L-carnitine females required less time to complete the course compared to the control female dogs but the difference was not significant (p=0.38).

TABLE 2

Time of 15 mile run for L-carnitine and control dogs completed at the end of the 90 day study

| Run Time | L-carnitine | Control | P-value |
|---|---|---|---|
| Final run time (min) | 95.84 ± 1.417$^A$ n = 19 | 102.4 ± 1.452$^B$ n = 16 | 0.0028 |
| ♂ | 93.91 ± 0.4564$^A$ n = 11 | 102.6 ± 2.067$^B$ n = 10 | 0.0004 |
| ♀ | 98.50 ± 3.179 n = 8 | 102.2 ± 2.007 n = 6 | 0.3871 |

Unpaired t-test. Data displayed indicates mean ± SEM. Differing letters indicates significant difference (P < 0.05).

The heart rate and body temperature recovery following the final long run was not different for the two treatments (Table 3).

TABLE 3

Heart rate and body temperature recovery following the 15 mile run with L-carnitine and control dogs.

| | L-carnitine | Control | P-value |
|---|---|---|---|
| Heartrate and Body Temp Before Run | | | |
| Temperature (° F.) | 101.3 ± 0.2 n = 20 | 101.2 ± 0.2 n = 20 | 0.7192 |
| ♂ | 101.7 ± 0.4 n = 11 | 101.6 ± 0.2 n = 11 | 0.9210 |
| ♀ | 101.0 ± 0.1 n = 9 | 100.8 ± 0.2 n = 9 | 0.4473 |

TABLE 3-continued

Heart rate and body temperature recovery following the 15 mile run with L-carnitine and control dogs.

| | L-carnitine | Control | P-value |
|---|---|---|---|
| Heartrate | 89$^A$ ± 2 n = 20 | 97$^B$ ± 3 n = 20 | 0.0246 |
| ♂ | 89 ± 3 n = 11 | 95 ± 5 n = 11 | 0.3272 |
| ♀ | 89 ± 3 n = 9 | 100 ± 3 n = 9 | 0.0060 |
| Heartrate After Run | | | |
| 0 min | 159 ± 4 n = 16 | 149 ± 6 n = 18 | 0.1994 |
| ♂ | 164 ± 6 n = 11 | 155 ± 7 n = 11 | 0.3993 |
| ♀ | 155 ± 5 n = 8 | 142 ± 10 n = 9 | 0.2882 |
| 2 min | 146 ± 5 n = 16 | 136 ± 6 n = 18 | 0.2333 |
| ♂ | 149 ± 6 n = 11 | 146 ± 7 n = 11 | 0.775 |
| ♀ | 139 ± 6 n = 8 | 130 ± 8 n = 9 | 0.4267 |
| 4 min | 131 ± 5 n = 16 | 128 ± 5 n = 18 | 0.6744 |
| ♂ | 143 ± 8 n = 11 | 135 ± 5 n = 11 | 0.4206 |
| ♀ | 123 ± 6 n = 8 | 123 ± 7 n = 8 | 1 |
| 6 min | 123 ± 5 n = 16 | 120 ± 5 n = 18 | 0.6491 |
| ♂ | 131 ± 6 n = 11 | 124 ± 6 n = 11 | 0.4136 |
| ♀ | 120 ± 6 n = 8 | 118 ± 7 n = 9 | 0.812 |
| 8 min | 114 ± 4 n = 16 | 111 ± 4 n = 18 | 0.5357 |
| ♂ | 125 ± 6 n = 11 | 118 ± 6 n = 11 | 0.481 |
| ♀ | 111 ± 6 n = 8 | 106 ± 4 n = 9 | 0.4424 |
| 10 min | 113 ± 5 n = 16 | 108 ± 4 n = 18 | 0.5168 |
| ♂ | 120 ± 6 n = 11 | 112 ± 7 n = 10 | 0.3936 |
| ♀ | 109 ± 5 n = 8 | 106 ± 5 n = 9 | 0.6735 |
| 12 min | 107 ± 4 n = 16 | 103 ± 3 n = 18 | 0.4294 |
| ♂ | 112 ± 5 n = 11 | 105 ± 5 n = 11 | 0.408 |
| ♀ | 107 ± 7 n = 7 | 104 ± 4 n = 9 | 0.7271 |
| 14 min | 101 ± 4 n = 16 | 97 ± 4 n = 18 | 0.4101 |
| ♂ | 102 ± 5 n = 10 | 100 ± 5 n = 11 | 0.7842 |
| ♀ | 103 ± 7 n = 7 | 98 ± 6 n = 9 | 0.5828 |
| Dog Body Temperature after run | | | |
| 0 min | 103.7 ± 0.3 n = 19 | 104.1 ± 0.3 n = 20 | 0.3056 |
| ♂ | 103.8 ± 0.3 n = 10 | 104.6 ± 0.3 n = 11 | 0.0571 |
| ♀ | 103.6 ± 0.5 n = 9 | 103.5 ± 0.4 n = 9 | 0.8547 |
| 15 min | 102.6 ± 0.2 n = 20 | 102.6 ± 0.2 n = 20 | 0.8499 |
| ♂ | 102.5 ± 0.2 n = 11 | 102.8 ± 0.2 n = 11 | 0.2919 |
| ♀ | 102.6 ± 0.4 n = 9 | 102.4 ± 0.3 n = 9 | 0.6093 |
| 30 min | 101.6 ± 0.1 n = 20 | 101.6 ± 0.1 n = 20 | 0.956 |
| ♂ | 101.9 ± 0.1 n = 11 | 101.9 ± 0.1 n = 11 | 0.9261 |
| ♀ | 101.3 ± 0.2 n = 9 | 101.4 ± 0.2 n = 9 | 0.8699 |
| 45 min | 101.1 ± 0.1 n = 20 | 100.8 ± 0.2 n = 19 | 0.3502 |
| ♂ | 101.1 ± 0.1 n = 11 | 101.1 ± 0.2 n = 11 | 0.7368 |
| ♀ | 101 ± 0.2 n = 9 | 100.6 ± 0.4 n = 8 | 0.3436 |
| 60 min | 100.9 ± 0.2 n = 20 | 101.1 ± 0.1 n = 20 | 0.4309 |
| ♂ | 101 ± 0.2 n = 11 | 101.2 ± 0.2 n = 11 | 0.2949 |
| ♀ | 100.8 ± 0.3 n = 9 | 100.8 ± 0.2 n = 9 | 0.9034 |
| 75 min | 100.7 ± 0.2 n = 19 | 100.9 ± 0.1 n = 20 | 0.3664 |
| ♂ | 100.7 ± 0.2 n = 11 | 101.1 ± 0.2 n = 11 | 0.1182 |
| ♀ | 100.7 ± 0.3 n = 8 | 100.6 ± 0.2 n = 9 | 0.8404 |
| 90 min | 100.7 ± 0.2 n = 20 | 100.8 ± 0.1 n = 20 | 0.8068 |
| ♂ | 100.8 ± 0.2 n = 11 | 100.9 ± 0.2 n = 11 | 0.6039 |
| ♀ | 100.6 ± 0.3 n = 9 | 100.6 ± 0.2 n = 9 | 0.8825 |
| 105 min | 100.4 ± 0.2 n = 19 | 100.6 ± 0.1 n = 20 | 0.3429 |
| ♂ | 100.5 ± 0.2 n = 11 | 100.9 ± 0.2 n = 11 | 0.2136 |
| ♀ | 100.2 ± 0.4 n = 8 | 100.3 ± 0.2 n = 9 | 0.7995 |
| 120 min | 100.7 ± 0.2 n = 14 | 100.9 ± 0.1 n = 20 | 0.5288 |
| ♂ | 100.8 ± 0.2 n = 10 | 101 ± 0.2 n = 11 | 0.2775 |
| ♀ | 100.7 ± 0.4 n = 4 | 100.7 ± 0.2 n = 9 | 0.9312 |

Unpaired t-test. Data displayed indicates mean ± SEM. Differing letters indicates significant difference (P < 0.05).

The amount of time to get heart rate back to basal levels was approximately 14 minutes and both treatments required this amount of time. The closest place for showing a heart rate difference was immediately following the long run. The L-carnitine dogs (M&F) had a numerical higher 159 average heart rate/minute compared to 149 for the control dogs (p=0.199). Both genders of L-carnitine dogs had numerically higher heart rates immediately following the runs but neither gender had a significant different heart rate compared to the two respective genders for the control dogs. The differential was gone by 4 minutes into the recovery and both groups showed a continuing decrease in heart rate through the 14 minutes of recovery.

The numerical higher heart rate for the L-carnitine dogs indicates they worked harder during the 15 mile run. The control males had a significantly higher (p=0.05) body temperature following the run compared to the L-carnitine males. The difference in body temperature between the L-carnitine males and the control males was gone within 15 minutes and both groups were back to pre-run core temperatures between 30-45 minutes following the 15 mile run. The core body temperature of the control males may have increased above the L-carnitine males because of a less efficient use of fuel during the 15 mile run. The L-carnitine males may have been able to utilize muscle lipids more efficiently during the intense exercise compared to the control males. If lipid utilization is limited because of a lack of L-carnitine in the skeletal muscle, a plausible explanation for the 1 degree increased core temperature of the control males would be because the control males had to shift to protein degradation for fuel in order to supply glucose. Protein catabolism and urea production produces the highest amount of heat production of all nutrients.

Each dog was observed 24 hr after each long run and several times following the final run during the study for the purpose of evaluating the recovery of the dogs. The dogs were scored from 1-5 for soreness and lameness and lack of desire to move. There were no noticeable effects of the long runs causing lameness or soreness for any of the dogs. An observation that everyone noticed was the dogs would eat less food on the morning following the long runs and the dogs were quick to get quiet and lay down when they were placed in their kennel at night following the long runs.

The food consumption was not significantly different over the entire 13 wk period between the treatments as shown in Table 4 below.

TABLE 4

Daily food consumption (g/d/lb BW and kcal/d/lb BW) of L-carnitine and control dogs during the 13 wk study

| | L-carnitine | Control | P-Value |
|---|---|---|---|
| Daily Food Intake (g/d/lb BW) | | | |
| Week 1 | 11.25 ± 0.51 n = 20 | 12.05 ± 0.32 n = 20 | 0.1935 |
| Week 2-3 | 10.67 ± 0.28 n = 20 | 11.27 ± 0.22 n = 20 | 0.0977 |
| Week 4-5 | 10.1 ± 0.35 n = 20 | 10.33 ± 0.2 n = 20 | 0.5639 |
| Week 6-7 | 10.22 ± 0.33 n = 20 | 10.22 ± 0.3 n = 20 | 0.9957 |
| Week 8-10 | 9.4 ± 0.25 n = 20 | 9.64 ± 0.16 n = 20 | 0.4247 |
| Week 11-12 | 9.04 ± 0.28 n = 20 | 9.59 ± 0.26 n = 20 | 0.1597 |
| Average | 10.11 ± 0.26 n = 20 | 10.52 ± 0.16 n = 20 | 0.1905 |
| Daily Food Intake (kcal ME/d/lb BW) | | | |
| Week 1 | 56.3 ± 2.6 n = 20 | 60.3 ± 1.6 n = 20 | 0.1935 |
| Week 2-3 | 53.3 ± 1.4 n = 20 | 56.4 ± 1.1 n = 20 | 0.0977 |
| Week 4-5 | 50.5 ± 1.7 n = 20 | 51.7 ± 1 n = 20 | 0.5639 |
| Week 6-7 | 51.1 ± 1.7 n = 20 | 51.1 ± 1.5 n = 20 | 0.9957 |
| Week 8-10 | 47 ± 1.2 n = 20 | 48.2 ± 0.8 n = 20 | 0.4247 |
| Week 11-12 | 45.2 ± 1.4 n = 20 | 47.9 ± 1.3 n = 20 | 0.1597 |
| Average | 50.6 ± 1.3 n = 20 | 52.6 ± 0.8 n = 20 | 0.1905 |
| Daily Food Intake (g) | | | |
| Week 1 | 717 ± 41 n = 20 | 795 ± 30 n = 20 | 0.1317 |
| Week 2 | 723 ± 26 n = 20 | 795 ± 30 n = 20 | 0.134 |
| Week 3 | 616$^B$ ± 31 n = 20 | 778$^A$ ± 25 n = 20 | 0.0317 |
| Week 4 | 636 ± 30 n = 20 | 714 ± 31 n = 20 | 0.1548 |
| Week 5 | 639 ± 27 n = 20 | 695 ± 28 n = 20 | 0.5409 |
| Week 6 | 651 ± 26 n = 20 | 664 ± 30 n = 20 | 0.2826 |
| Week 7 | 626 ± 24 n = 20 | 692 ± 27 n = 20 | 0.7745 |
| Week 8 | 626 ± 24 n = 20 | 636 ± 24 n = 20 | 0.5464 |
| Week 9 | 622 ± 26 n = 20 | 645 ± 20 n = 20 | 0.3647 |
| Week 10 | 570 ± 25 n = 20 | 655 ± 26 n = 20 | 0.1101 |
| Week 11 | 577 ± 24 n = 20 | 627 ± 23 n = 20 | 0.07 |
| Week 12 | 583$^B$ ± 21 n = 20 | 644$^A$ ± 27 n = 20 | 0.0404 |
| Week 13 | 555 ± 20 n = 20 | 650 ± 23 n = 20 | 0.1237 |
| Average | 626 ± 24 n = 20 | 677 ± 23 n = 20 | 0.1291 |

Unpaired t-test. Data displayed indicates mean ± SEM. Differing letters indicates significant difference (P < 0.05).

During the first 4 wks of the study and the last 4 wks of the study the difference in food consumption between L-carnitine dogs and control dogs is close to being significantly different (FIG. 1). The p values for difference for the first four weeks ranges between 0.03-0.15 and the p values for difference for the last four wks ranged between 0.04-0.13. The overall average food intake per day for L-carnitine dogs was 626 g/day compared to 677 g/day for control dogs (p=0.12). Since the control dogs gained slightly more weight (not significant) during the 90 day study, the food consumption reported on g/day/lb BW or kcal ME/d/lb BW was less different than the L-carnitine dogs (p=0.19).

The L-carnitine dogs are clearly indicating less need for dietary energy to maintain their work and BW. The L-carnitine dogs were able to utilize their fat reserves during the 90 day program and needed less food energy on a daily basis to sustain their BW. The body weights of the dogs were not significantly different during the study (Table 5).

TABLE 5

Bodyweights for the L-carnitine and control dogs during the 13 wk study
Body Weights (lb)

| | L-carnitine | Control | P-Value |
|---|---|---|---|
| Week 1 Wt. (lb) | 61 ± 1.9 n = 20 | 62.6 ± 1.7 n = 20 | 0.5344 |
| ♂ | 65.9 ± 2.5 n = 11 | 68 ± 1.4 n = 11 | 0.4525 |
| ♀ | 55 ± 1.2 n = 9 | 55.9 ± 1.7 n = 9 | 0.6601 |
| Week 3 Wt. (lb) | 63.4 ± 1.9 n = 20 | 66.1 ± 1.9 n = 20 | 0.3405 |
| ♂ | 67.8 ± 2.8 n = 11 | 71.6 ± 1.7 n = 11 | 0.2578 |
| ♀ | 58.1 ± 1.2 n = 9 | 59.3 ± 2.2 n = 9 | 0.639 |
| Week 5 Wt. (lb) | 62.8 ± 2 n = 20 | 66.2 ± 1.9 n = 20 | 0.229 |
| ♂ | 66.6 ± 3 n = 11 | 71.2 ± 1.8 n = 11 | 0.2002 |
| ♀ | 58.3 ± 1.2 n = 9 | 60 ± 2.4 n = 9 | 0.526 |
| Week 7 Wt. (lb) | 63 ± 1.8 n = 20 | 65.4 ± 1.8 n = 20 | 0.3622 |
| ♂ | 66.3 ± 2.7 n = 11 | 69.8 ± 1.8 n = 11 | 0.2965 |
| ♀ | 59 ± 1.4 n = 9 | 60 ± 2.5 n = 9 | 0.7353 |
| Week 9 Wt. (lb) | 62.8 ± 1.9 n = 20 | 65.1 ± 1.8 n = 20 | 0.3829 |
| ♂ | 66.5 ± 2.9 n = 11 | 69.3 ± 1.8 n = 11 | 0.4342 |
| ♀ | 58.2 ± 1.7 n = 9 | 60.1 ± 2.6 n = 9 | 0.5395 |
| Week 11 Wt. (lb) | 64.4 ± 2 n = 20 | 66.6 ± 1.9 n = 20 | 0.426 |
| ♂ | 68.8 ± 2.8 n = 11 | 71.2 ± 1.7 n = 11 | 0.4822 |
| ♀ | 59 ± 1.5 n = 9 | 61.1 ± 2.8 n = 9 | 0.5254 |
| Week 13 Wt. (lb) | 64.9 ± 2 n = 20 | 68 ± 2 n = 20 | 0.2853 |
| ♂ | 69.3 ± 2.8 n = 11 | 72.3 ± 2 n = 11 | 0.3906 |
| ♀ | 59.6 ± 1.5 n = 9 | 62.7 ± 3 n = 9 | 0.3664 |

Unpaired t-test. Data displayed indicates mean ± SEM. Differing letters indicates significant difference (P < 0.05).

Figure 2:
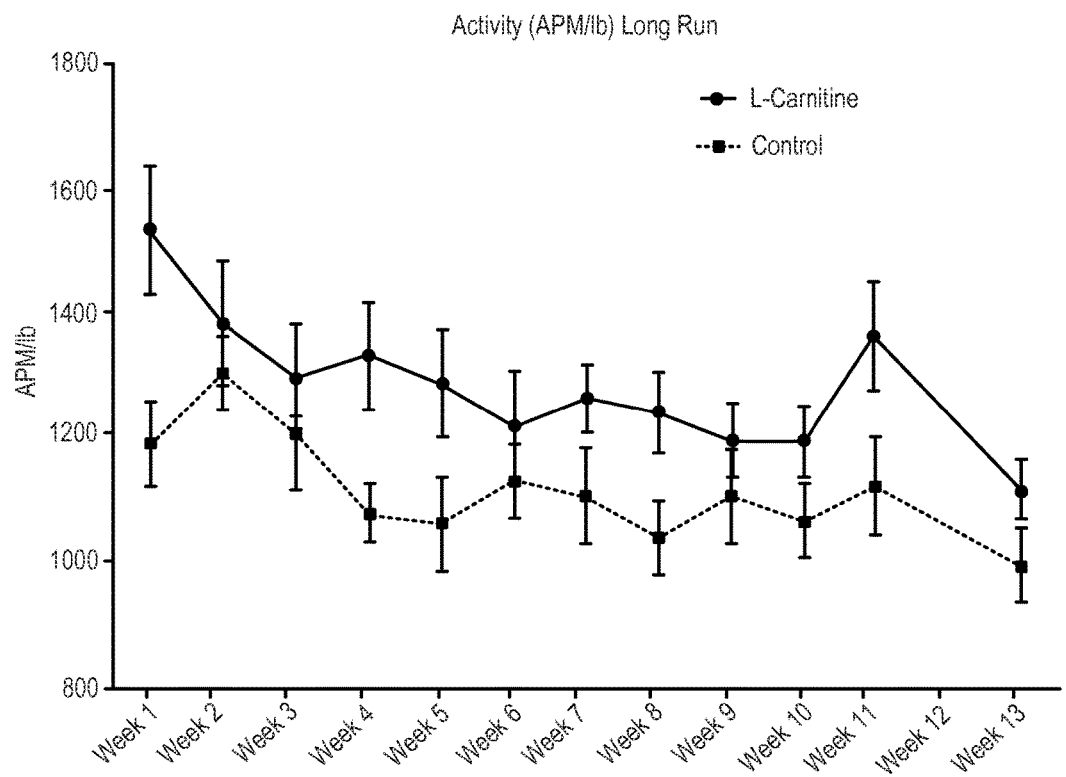
Figure 2A:
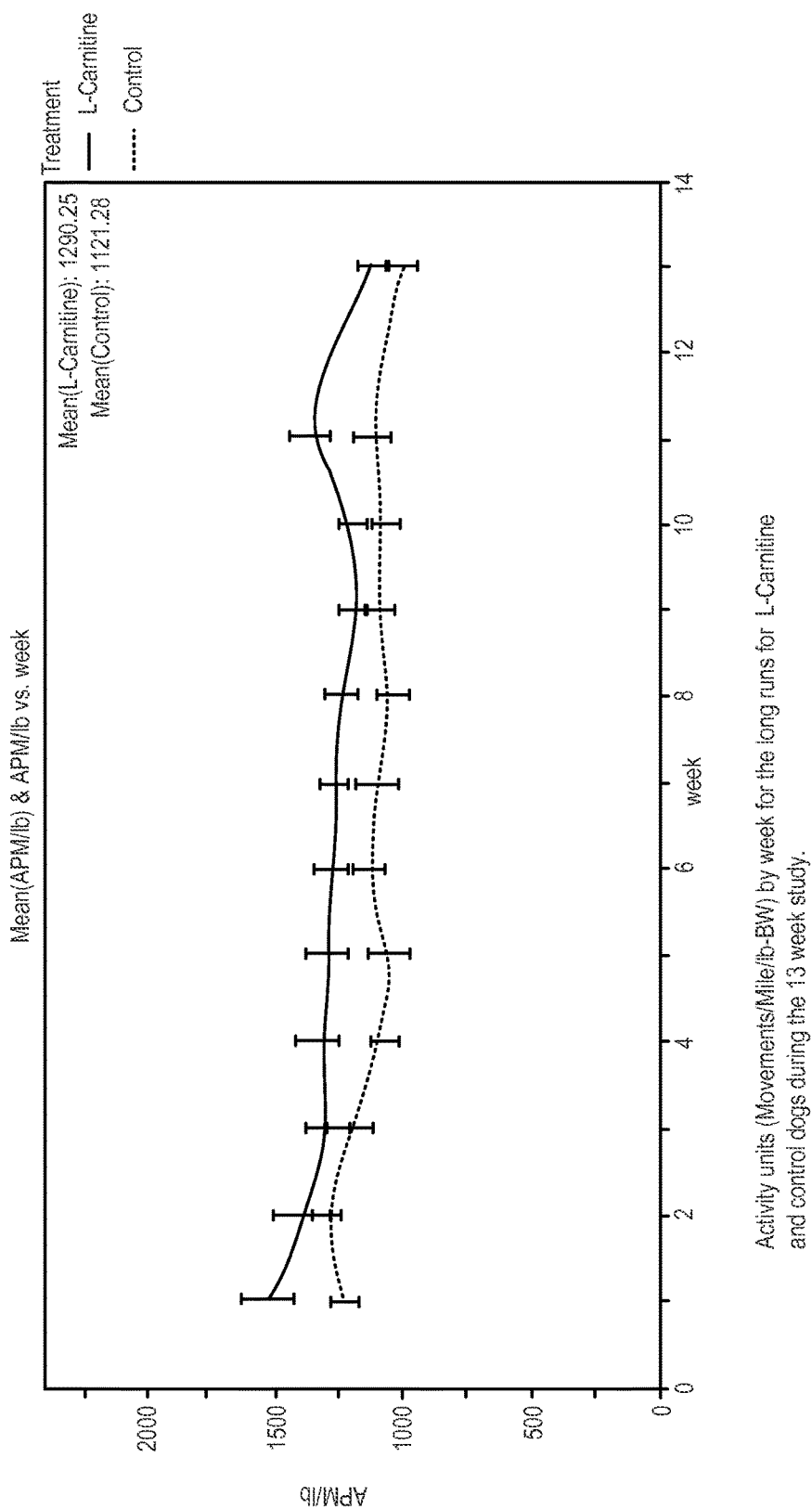
Figure 2B:
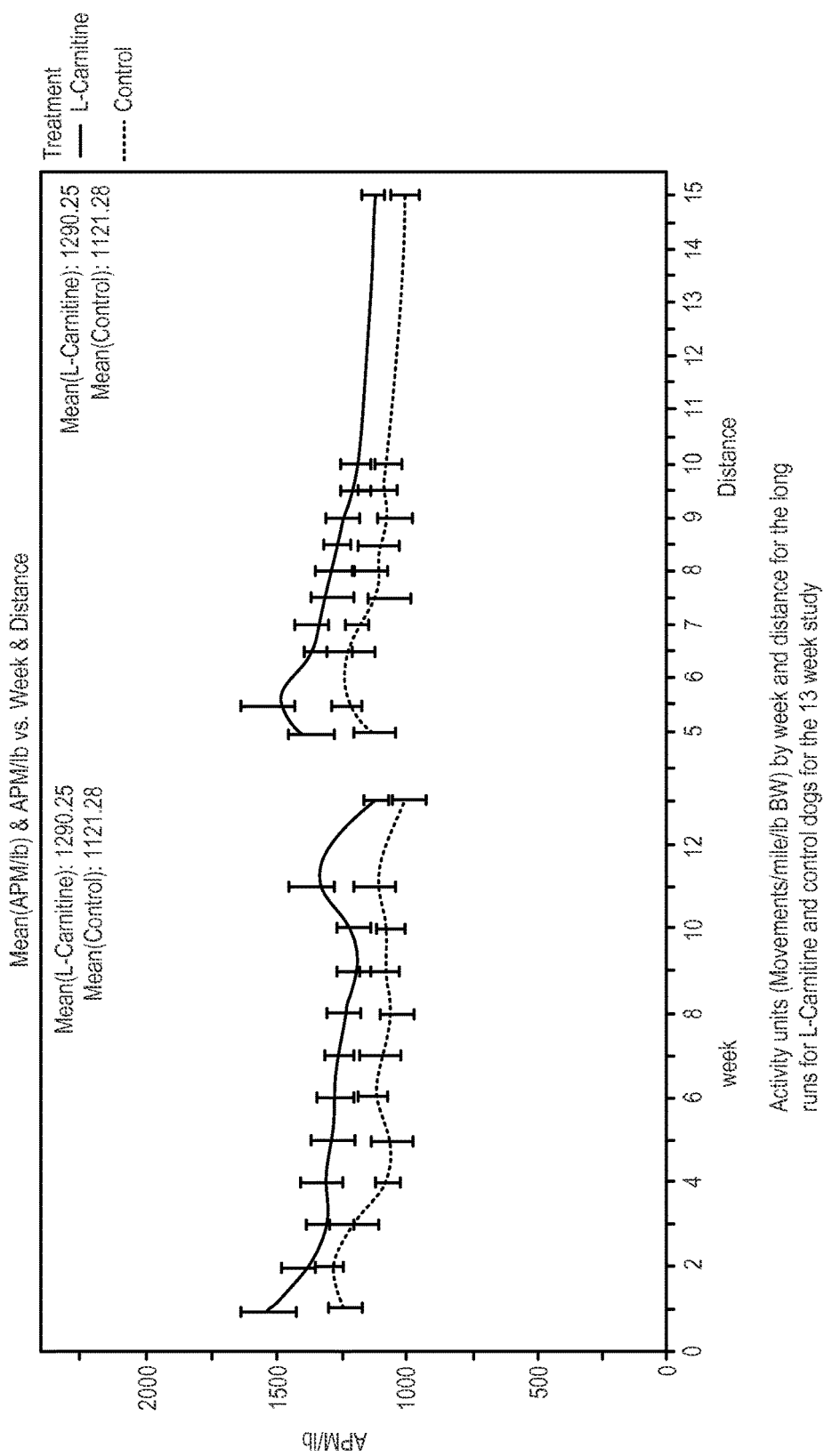
Figure 2C:
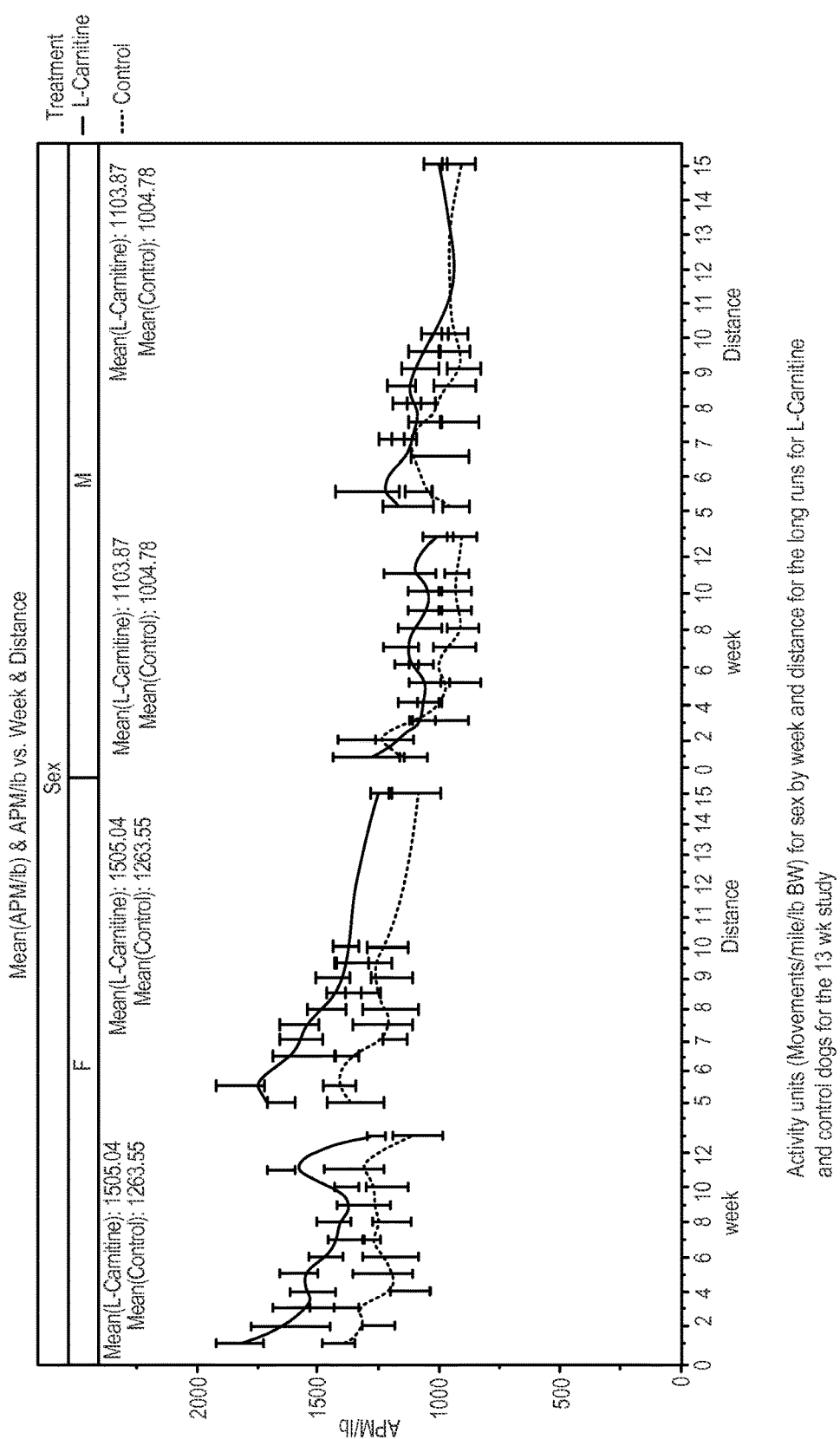

The dogs each gained BW over the 13 wk period but the differences were not significant between treatments. The activity measured by Actical monitors for the long runs are reported in Table 6 and in FIG. 2 (2a,2b,2c in back of report covering long run by wk, long run by wk and distance, long run by wk, distance and sex).

TABLE 6

Activity (Movements/Mile/LB BW) measured by Actical monitors for Long runs for L-carnitine and control dogs using a mixed statistical model.

| Term | Estimate | Std Error | DFDen | t Ratio | Prob > \|t\| |
|---|---|---|---|---|---|
| Intercept | 1453.8949 | 42.13187 | 90.63 | 34.51 | <.0001* |
| Treatment[L-carnitine] | 90.939359 | 33.09474 | 35.63 | 2.75 | 0.0094* |
| Sex[F] | 157.69798 | 33.09473 | 35.63 | 4.77 | <.0001* |
| Week | −14.31297 | 2.924954 | 410.8 | −4.89 | <.0001* |
| Distance | −16.04399 | 4.140661 | 410.6 | −3.87 | 0.0001* |
| Sex[F] * Treatment[L-carnitine] | 34.486651 | 33.09473 | 35.63 | 1.04 | 0.3044 |
| (Distance-8.24396) * Treatment[L-carnitine] | −7.3235 | 4.140661 | 410.6 | −1.77 | 0.0777 |
| (Week-6.67253) * Treatment[L-carnitine] | 0.1852053 | 2.924954 | 410.8 | 0.06 | 0.9495 |

| Level | | | Least Sq Mean |
|---|---|---|---|
| Treatment α = 0.050 | | | |
| L-carnitine | A | | 1317.0647 |
| Control | | B | 1135.1860 |
| Sex α = 0.050 | | | |
| F | A | | 1383.8233 |
| M | | B | 1068.4274 |
| Sex * Treatment α = 0.050 | | | |
| F, L-carnitine | A | | 1509.2493 |
| F, Control | | B | 1258.3973 |
| M, L-carnitine | | B | C | 1124.8801 |
| M, Control | | | C | 1011.9746 |

| | | | Treatment | | | |
|---|---|---|---|---|---|---|
| | | | L-carnitine APM/lb | | Control APM/lb | |
| Sex | Week | N | Mean | Std Err | N | Mean | Std Err |
| | 1 | 20 | 1535 | 103 | 19 | 1233 | 54 |
| | 2 | 19 | 1385 | 97 | 20 | 1303 | 52 |
| | 3 | 17 | 1298 | 88 | 19 | 1209 | 92 |
| | 4 | 16 | 1334 | 82 | 20 | 1079 | 49 |
| | 5 | 20 | 1288 | 81 | 19 | 1063 | 77 |
| | 6 | 17 | 1278 | 71 | 18 | 1135 | 59 |
| | 7 | 18 | 1264 | 54 | 17 | 1105 | 79 |
| | 8 | 20 | 1241 | 65 | 19 | 1040 | 61 |
| | 9 | 20 | 1194 | 54 | 20 | 1108 | 75 |
| | 10 | 19 | 1192 | 57 | 20 | 1067 | 58 |
| | 11 | 20 | 1364 | 85 | 20 | 1122 | 76 |
| | 13 | 20 | 1116 | 44 | 20 | 995 | 59 |
| F | 1 | 9 | 1825 | 102 | 8 | 1417 | 68 |
| | 2 | 9 | 1616 | 163 | 9 | 1250 | 70 |
| | 3 | 8 | 1559 | 126 | 9 | 1440 | 99 |
| | 4 | 9 | 1522 | 91 | 9 | 1122 | 86 |
| | 5 | 9 | 1582 | 81 | 9 | 1235 | 125 |
| | 6 | 8 | 1472 | 75 | 8 | 1205 | 115 |
| | 7 | 8 | 1391 | 69 | 7 | 1340 | 96 |
| | 8 | 9 | 1437 | 68 | 9 | 1200 | 81 |
| | 9 | 9 | 1355 | 58 | 9 | 1317 | 109 |
| | 10 | 9 | 1385 | 48 | 9 | 1216 | 83 |
| | 11 | 9 | 1655 | 58 | 9 | 1352 | 120 |
| | 13 | 9 | 1251 | 39 | 9 | 1097 | 101 |
| M | 1 | 11 | 1298 | 132 | 11 | 1098 | 50 |
| | 2 | 10 | 1177 | 65 | 11 | 1346 | 77 |
| | 3 | 9 | 1065 | 49 | 10 | 1001 | 119 |
| | 4 | 7 | 1093 | 84 | 11 | 1043 | 56 |
| | 5 | 11 | 1048 | 73 | 10 | 908 | 66 |
| | 6 | 9 | 1105 | 83 | 10 | 1078 | 53 |
| | 7 | 10 | 1162 | 65 | 10 | 941 | 86 |
| | 8 | 11 | 1081 | 77 | 10 | 897 | 66 |
| | 9 | 11 | 1062 | 64 | 11 | 937 | 73 |
| | 10 | 10 | 1018 | 57 | 11 | 945 | 61 |
| | 11 | 11 | 1126 | 102 | 11 | 933 | 52 |
| | 13 | 11 | 1006 | 55 | 11 | 912 | 61 |

Levels not connected by same letter are significantly different.

The L-carnitine dogs produced significantly more activity (p=0.0094) during the 13 wk study and the female dog generated more activity compared to the male (p<0.0001). The data also indicates that both treatments of dogs generated less activity as the weeks continued (p<0.0001) during the study and also as the distance of the long runs increased (p<0.0001). The sex by treatment interaction was not significant (p=0.30) but the activity data showed that the female L-carnitine dogs produced significantly more activity (p<0.05) of 1509 (activity movements/mile/lb BW) than 1258 for the female control dogs, 1124 for the male L-carnitine dogs, and 1011 for male control dogs. The male L-carnitine dogs were faster for the time trial at the end of the study compared to male control and female dogs of both treatments but during the weekly long runs the females showed more overall activity. The female dogs may have been more focused on running whereas the male dogs tended to be more occupied with female scent and in marking territory along the track.

Figure 3:
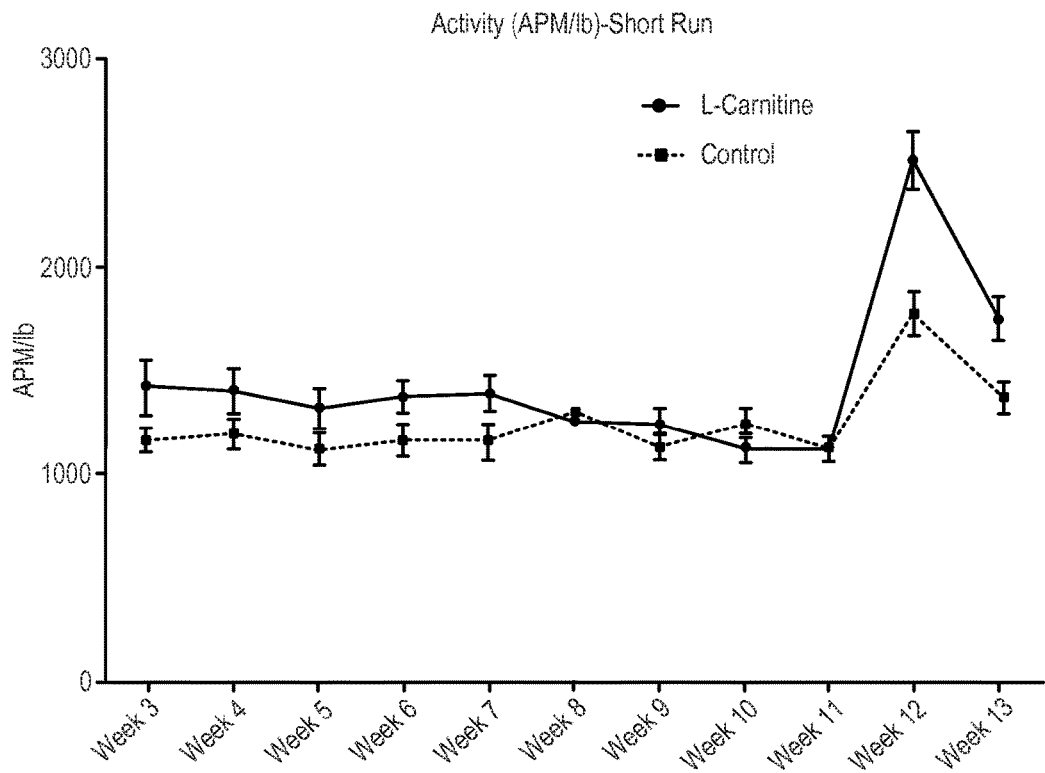
Figure 3A:
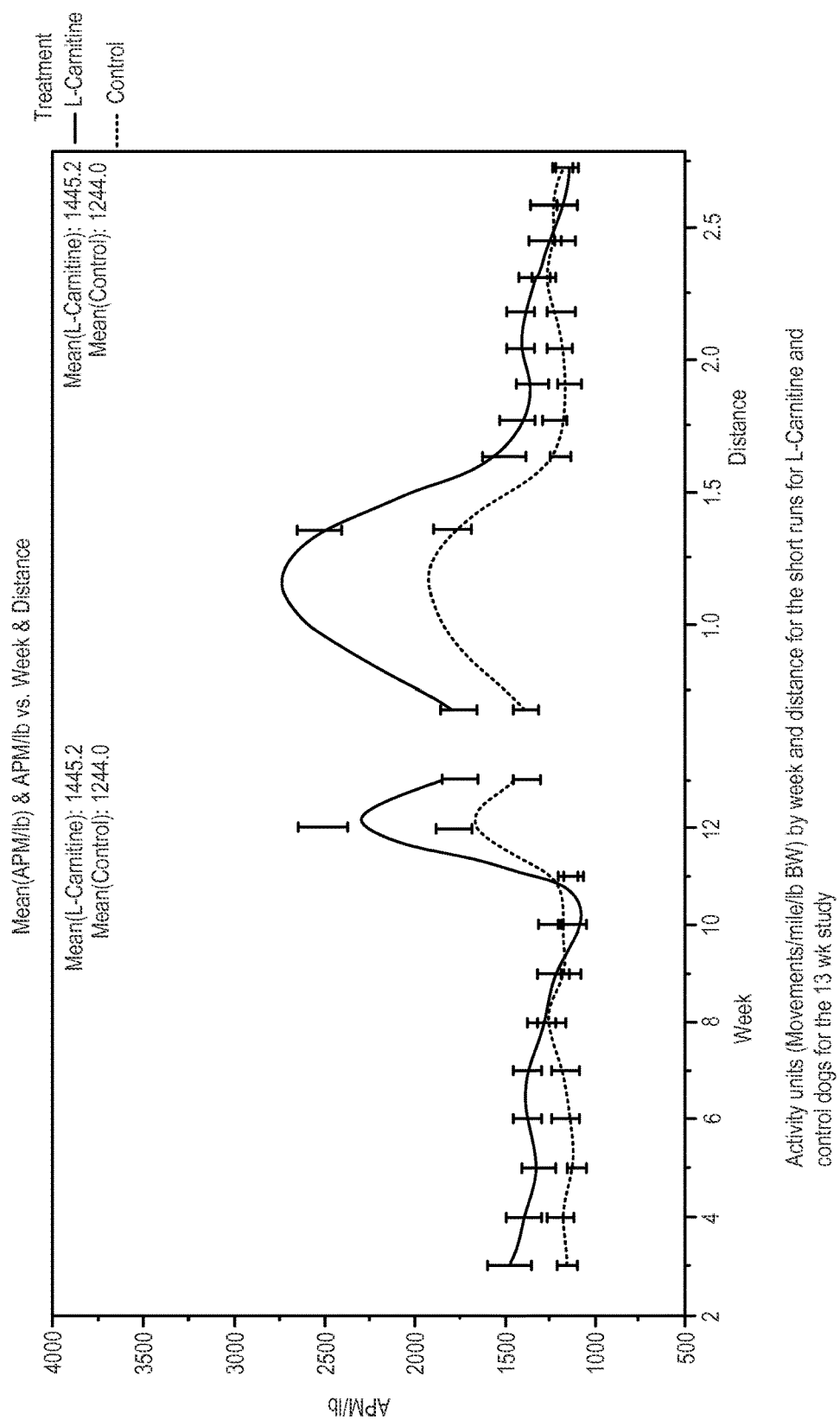
Figure 3B:
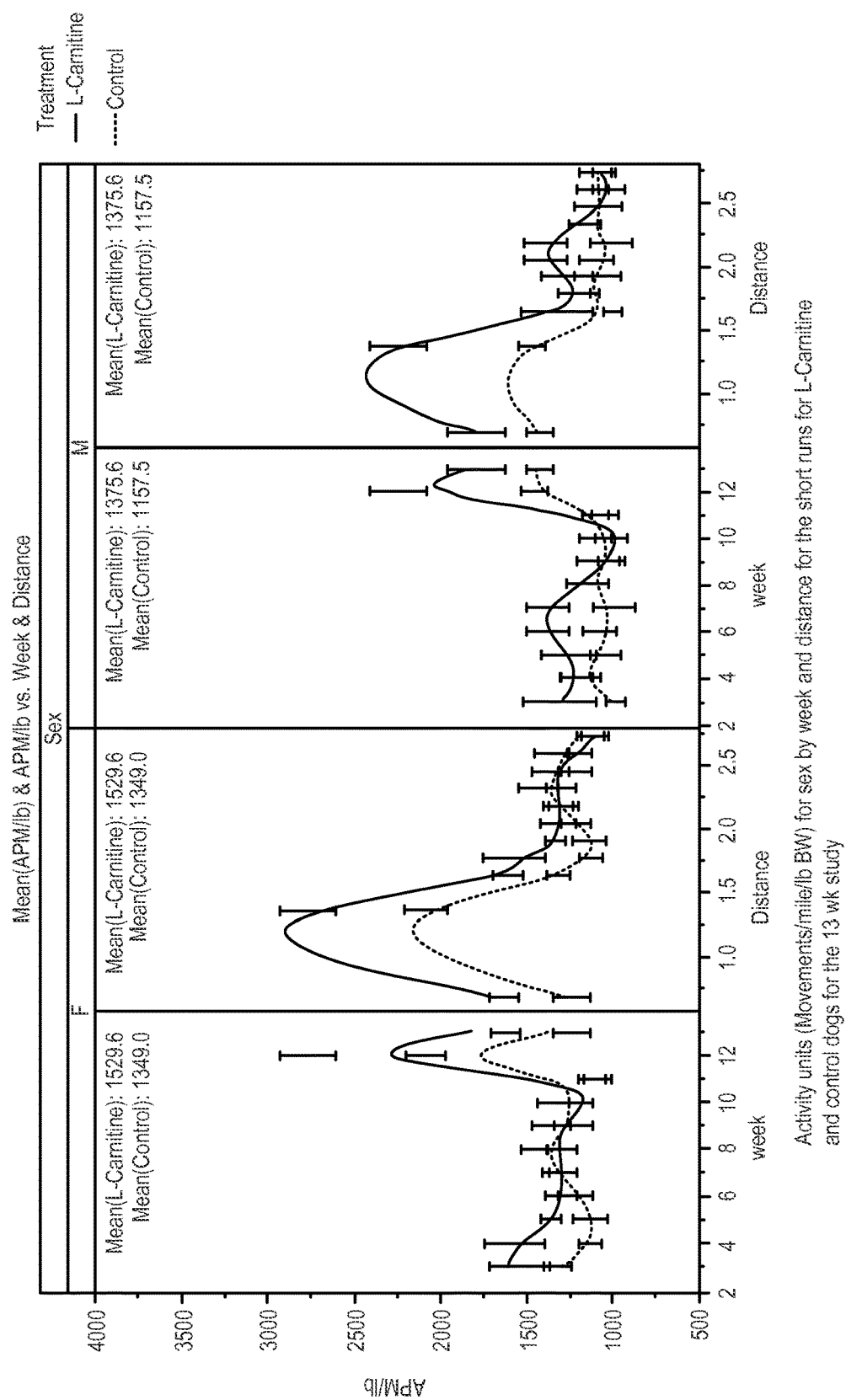

The activities measured by Actical monitors for the weekly short runs (2 sessions per wk) are reported in Table 7 and in FIGS. 3 (3a and 3b in back of report covering short run by wk and distance and short run by wk, distance and sex).

TABLE 7

Activity (Movements/Mile/LB BW) measured by Actical monitors for short runs for L-carnitine and control dogs using a mixed statistical model

| Term | Estimate | Std Error | DFDen | t Ratio | Prob > \|t\| |
|---|---|---|---|---|---|
| Intercept | 1697.6611 | 83.49651 | 336.2 | 20.33 | <.0001* |
| Sex[F] | 86.560639 | 39.94406 | 35.96 | 2.17 | 0.0369* |
| Treatment[L-carnitine] | 97.708637 | 39.94357 | 35.96 | 2.45 | 0.0195* |
| Week | 29.850095 | 5.085583 | 392.2 | 5.87 | <.0001* |
| Distance | −295.5264 | 28.34332 | 392.2 | −10.43 | <.0001* |
| Sex[F] * Treatment[L-carnitine] | −8.973682 | 39.94406 | 35.96 | −0.22 | 0.8235 |
| Treatment[L-carnitine] * (Week-8) | 0.4292492 | 5.085583 | 392.2 | 0.08 | 0.9328 |
| Treatment[L-carnitine] * (Distance-1.97321) | −150.1119 | 28.34332 | 392.2 | −5.30 | <.0001* |

| Level | | | Least Sq Mean |
|---|---|---|---|
| Treatment α = 0.050 | | | |
| L-carnitine | A | | 1451.0357 |
| Control | | B | 1255.6184 |
| Sex α = 0.050 | | | |
| F | A | | 1439.8877 |
| M | | B | 1266.7664 |

TABLE 7-continued

| Sex * Treatment α = 0.050 | | | | |
|---|---|---|---|---|
| F, L-carnitine | A | | | 1528.6226 |
| M, L-carnitine | A | B | | 1373.4487 |
| F, Control | A | B | | 1351.1527 |
| M, Control | | B | | 1160.0841 |

| | | Treatment | | | | |
|---|---|---|---|---|---|---|
| | | L-carnitine APM/lb | | | Control APM/lb | |
| Sex | Week | N | Mean | Std Err | N | Mean | Std Err |
| | 3 | 19 | 1479 | 121 | 20 | 1159 | 57 |
| | 4 | 20 | 1402 | 101 | 20 | 1190 | 66 |
| | 5 | 20 | 1314 | 92 | 19 | 1107 | 66 |
| | 6 | 20 | 1375 | 79 | 20 | 1161 | 66 |
| | 7 | 20 | 1380 | 76 | 20 | 1152 | 85 |
| | 8 | 20 | 1249 | 65 | 20 | 1299 | 83 |
| | 9 | 20 | 1234 | 90 | 20 | 1122 | 59 |
| | 10 | 20 | 1114 | 60 | 20 | 1236 | 71 |
| | 11 | 20 | 1111 | 61 | 19 | 1117 | 48 |
| | 12 | 20 | 2500 | 128 | 20 | 1766 | 97 |
| | 13 | 20 | 1741 | 97 | 19 | 1367 | 68 |
| F | 3 | 9 | 1636 | 88 | 9 | 1341 | 66 |
| | 4 | 9 | 1608 | 174 | 9 | 1161 | 61 |
| | 5 | 9 | 1362 | 54 | 9 | 1160 | 99 |
| | 6 | 9 | 1340 | 100 | 9 | 1239 | 81 |
| | 7 | 9 | 1347 | 100 | 9 | 1319 | 84 |
| | 8 | 9 | 1330 | 82 | 9 | 1454 | 110 |
| | 9 | 9 | 1388 | 112 | 9 | 1238 | 89 |
| | 10 | 9 | 1222 | 71 | 9 | 1380 | 94 |
| | 11 | 9 | 1128 | 81 | 9 | 1152 | 83 |
| | 12 | 9 | 2804 | 157 | 9 | 2115 | 115 |
| | 13 | 9 | 1661 | 86 | 8 | 1269 | 111 |
| M | 3 | 10 | 1338 | 211 | 11 | 1009 | 58 |
| | 4 | 11 | 1234 | 95 | 11 | 1214 | 112 |
| | 5 | 11 | 1275 | 164 | 10 | 1060 | 90 |
| | 6 | 11 | 1403 | 121 | 11 | 1098 | 99 |
| | 7 | 11 | 1407 | 116 | 11 | 1015 | 128 |
| | 8 | 11 | 1183 | 96 | 11 | 1172 | 111 |
| | 9 | 11 | 1108 | 127 | 11 | 1028 | 71 |
| | 10 | 11 | 1026 | 87 | 11 | 1118 | 92 |
| | 11 | 11 | 1098 | 93 | 10 | 1086 | 54 |
| | 12 | 11 | 2251 | 164 | 11 | 1480 | 74 |
| | 13 | 11 | 1806 | 164 | 11 | 1438 | 83 |

Levels not connected by same letter are significantly different.

The female for both treatments produced more activity (activity units/mile/lb BW) compared to the male throughout the 13 wk study (p=0.0369). The L-carnitine dogs significantly produced more activity (activity units/mile/lb BW) compared to the control dogs (p=0.0195). The short runs also showed that the dogs decreased in activity as the distance increased (p<0.0001) and as the weeks of the study continued (p<0.0001). The only part of the study that does not equate weeks and increasing distance is when the dogs go through a reduction of distance in wk 11 and 12 for the training taper program thus allowing a build-up of energy that was needed to complete the 15 mile final run. The L-carnitine dogs clearly put more energy into their short runs throughout the 13 wk period compared to the control dogs.

The mean values for each of the serum biomarkers representing the different stages of training and exercise (baseline, pre-run, and post-run) are included in Table 8.

TABLE 8

Blood biomarkers for baseline, pre-run and post-run time periods for L-carnitine and control groups using a mixed statistical model.

| | | | Treatment | | | | | |
|---|---|---|---|---|---|---|---|---|
| | | | L-carnitine | | | Control | | |
| | | | N | Mean | Std Err | N | Mean | Std Err |
| | Time | | | | | | | |
| Creatine Kinase (mU · mL) | Baseline | | 17 | 22.9 | 4.9 | 18 | 18.8 | 1.9 |
| | Pre-run | | 20 | 7.0 | 0.6 | 20 | 6.8 | 0.8 |
| | Post-run | | 18 | 16.1 | 2.0 | 15 | 20.7 | 2.3 |
| Myoglobin (ng/mL) | Baseline | | 14 | 10.0 | 3.2 | 16 | 5.2 | 0.9 |
| | Pre-run | | 16 | 9.0 | 1.7 | 19 | 6.5 | 1.6 |
| | Post-run | | 20 | 19.2 | 4.6 | 20 | 30.0 | 5.9 |
| TBARS (uM MDA) | Baseline | | 20 | 12.37 | 0.92 | 20 | 13.50 | 1.44 |
| | Pre-run | | 20 | 12.18 | 0.90 | 20 | 11.70 | 0.87 |
| | Post-run | | 20 | 12.59 | 0.82 | 20 | 13.84 | 1.05 |
| TAC (mM Trolox Equiv) | Baseline | | 20 | 0.107 | 0.003 | 20 | 0.104 | 0.004 |
| | Pre-run | | 20 | 0.118 | 0.006 | 20 | 0.118 | 0.006 |
| | Post-run | | 20 | 0.087 | 0.005 | 20 | 0.089 | 0.006 |
| Sex | Time | | | | | | | |
| F | Baseline | Creatine Kinase (mU · mL) | 7 | 35.8 | 10.0 | 7 | 17.7 | 4.2 |
| | | Myoglobin (ng/mL) | 5 | 17.6 | 6.8 | 6 | 5.6 | 1.7 |
| | | TBARS (uM MDA) | 9 | 14.10 | 1.21 | 9 | 14.34 | 2.90 |
| | | TAC (mM Trolox Equiv) | 9 | 0.106 | 0.004 | 9 | 0.100 | 0.006 |
| | Pre-run | Creatine Kinase (mU · mL) | 9 | 6.9 | 1.2 | 9 | 6.2 | 0.8 |
| | | Myoglobin (ng/mL) | 6 | 8.4 | 4.4 | 8 | 5.2 | 2.3 |
| | | TBARS (uM MDA) | 9 | 15.13 | 1.32 | 9 | 13.32 | 1.60 |
| | | TAC (mM Trolox Equiv) | 9 | 0.106 | 0.005 | 9 | 0.098 | 0.007 |
| | Post-run | Creatine Kinase (mU · mL) | 9 | 19.9 | 2.4 | 4 | 21.6 | 6.6 |
| | | Myoglobin (ng/mL) | 9 | 24.5 | 9.3 | 9 | 40.6 | 9.5 |
| | | TBARS (uM MDA) | 9 | 14.47 | 0.98 | 9 | 16.06 | 1.88 |
| | | TAC (mM Trolox Equiv) | 9 | 0.069 | 0.005 | 9 | 0.066 | 0.008 |

TABLE 8-continued

Blood biomarkers for baseline, pre-run and post-run time periods for L-carnitine and control groups using a mixed statistical model.

| | | | Treatment | | | | | |
|---|---|---|---|---|---|---|---|---|
| | | | L-carnitine | | | Control | | |
| | | | N | Mean | Std Err | N | Mean | Std Err |
| M | Baseline | Creatine Kinase (mU · mL) | 10 | 13.9 | 1.6 | 11 | 19.5 | 1.7 |
| | | Myoglobin (ng/mL) | 9 | 5.8 | 2.6 | 10 | 5.0 | 1.0 |
| | | TBARS (uM MDA) | 11 | 10.96 | 1.22 | 11 | 12.81 | 1.24 |
| | | TAC (mM Trolox Equiv) | 11 | 0.107 | 0.005 | 11 | 0.107 | 0.004 |
| | Pre-run | Creatine Kinase (mU · mL) | 11 | 7.0 | 0.6 | 11 | 7.4 | 1.3 |
| | | Myoglobin (ng/mL) | 10 | 9.3 | 1.2 | 11 | 7.4 | 2.2 |
| | | TBARS (uM MDA) | 11 | 9.77 | 0.61 | 11 | 10.38 | 0.74 |
| | | TAC (mM Trolox Equiv) | 11 | 0.128 | 0.010 | 11 | 0.134 | 0.006 |
| | Post-run | Creatine Kinase (mU · mL) | 9 | 12.2 | 2.8 | 11 | 20.3 | 2.4 |
| | | Myoglobin (ng/mL) | 11 | 14.9 | 3.3 | 11 | 21.3 | 6.6 |
| | | TBARS (uM MDA) | 11 | 11.06 | 1.08 | 11 | 12.03 | 0.89 |
| | | TAC (mM Trolox Equiv) | 11 | 0.102 | 0.006 | 11 | 0.108 | 0.004 |

Myoglobin values were compared for the different treatments in Table 9.

TABLE 9

Myoglobin for L-carnitine and control dogs using a mixed statistical model

| Term | Estimate | Std Error | DFDen | t Ratio | Prob > \|t\| |
|---|---|---|---|---|---|
| Intercept | 8.4493372 | 2.927565 | 89.84 | 2.89 | 0.0049* |
| Time[Pre-run-Baseline] | −0.41628 | 3.569878 | 54.55 | −0.12 | 0.9076 |
| Time[Post-run-Pre-run] | 17.289569 | 3.223496 | 51.37 | 5.36 | <.0001* |
| Treatment[L-carnitine] | 1.6530698 | 2.927565 | 89.84 | 0.56 | 0.5737 |
| Sex[F] | 3.0902931 | 2.927565 | 89.84 | 1.06 | 0.2940 |
| Time[Pre-run-Baseline] * Treatment[L-carnitine] | 0.3221531 | 3.569878 | 54.55 | 0.09 | 0.9284 |
| Time[Post-run-Pre-run] * Treatment[L-carnitine] | −7.62492 | 3.223496 | 51.37 | −2.37 | 0.0218* |
| Treatment[L-carnitine] * Sex[F] | 1.5819967 | 2.927565 | 89.84 | 0.54 | 0.5903 |
| Time[Pre-run-Baseline] * Sex[F] | −3.255362 | 3.569878 | 54.55 | −0.91 | 0.3658 |
| Time[Post-run-Pre-run] * Sex[F] | 7.3713314 | 3.223496 | 51.37 | 2.29 | 0.0264* |
| Time[Pre-run-Baseline] * Treatment[L-carnitine] * Sex[F] | −0.369018 | 3.569878 | 54.55 | −0.10 | 0.9180 |
| Time[Post-run-Pre-run] * Treatment[L-carnitine] * Sex[F] | −3.629948 | 3.223496 | 51.37 | −1.13 | 0.2654 |

Effect Details

| Level | | | Least Sq Mean |
|---|---|---|---|

Myoglobin (ng/mL) - Time - LSMeans Differences Student's t
α = 0.050

| Post-run | A | | 25.322626 |
| Baseline | B | | 8.449337 |
| Pre-run | B | | 8.033058 |

Myoglobin (ng/mL) - Treatment - LSMeans Differences Student's t
α = 0.050

| L-carnitine | A | | 10.102407 |
| Control | A | | 6.796267 |

Myoglobin (ng/mL) - Sex - LSMeans Differences Student's t
α = 0.050

| F | A | | 11.539630 |
| M | A | | 5.359044 |

Myoglobin (ng/mL) - Time * Treatment - LSMeans Differences Student's t
α = 0.050

| Post-run, Control | A | | 30.972323 |
| Post-run, L-carnitine | B | | 19.672929 |
| Baseline, L-carnitine | B | C | 10.102407 |
| Pre-run, L-carnitine | | C | 10.008281 |
| Baseline, Control | | C | 6.796267 |
| Pre-run, Control | | C | 6.057835 |

TABLE 9-continued

Myoglobin for L-carnitine and control dogs using a mixed statistical model

Myoglobin (ng/mL) - Treatment * Sex - LSMeans Differences Student's t
α = 0.050

| | | | | | |
|---|---|---|---|---|---|
| L-carnitine, F | A | | | | 14.774697 |
| Control, F | A | | | | 8.304564 |
| L-carnitine, M | A | | | | 5.430117 |
| Control, M | A | | | | 5.287971 |

Myoglobin (ng/mL) - Time * Sex - LSMeans Differences Student's t
α = 0.050

| | | | | | |
|---|---|---|---|---|---|
| Post-run, F | A | | | | 32.528889 |
| Post-run, M | | B | | | 18.116364 |
| Baseline, F | | B | C | | 11.539630 |
| Pre-run, M | | | C | | 8.198126 |
| Pre-run, F | | B | C | | 7.867989 |
| Baseline, M | | | C | | 5.359044 |

Myoglobin (ng/mL) - Time * Treatment * Sex - LSMeans Differences Student's t
α = 0.050

| | | | | | |
|---|---|---|---|---|---|
| Post-run, Control, F | A | | | | 40.595556 |
| Post-run, L-carnitine, F | | B | | | 24.462222 |
| Post-run, Control, M | | B | C | | 21.349091 |
| Post-run, L-carnitine, M | | B | C | D | 14.883636 |
| Baseline, L-carnitine, F | | B | C | D | 14.774697 |
| Pre-run, L-carnitine, F | | B | C | D | 11.056190 |
| Pre-run, L-carnitine, M | | | C | D | 8.960371 |
| Baseline, Control, F | | | C | D | 8.304564 |
| Pre-run, Control, M | | | | D | 7.435882 |
| Baseline, L-carnitine, M | | | | D | 5.430117 |
| Baseline, Control, M | | | | D | 5.287971 |
| Pre-run, Control, F | | | | D | 4.679788 |

Levels not connected by same letter are significantly different.

Myoglobin values in the serum show there was a significant increase ($p<0.0001$) in myoglobin from the pre-run to the post-run period. The results clearly show that myoglobin is being lost from the skeletal muscle because of muscle damage during the long 15 final run. The L-carnitine dogs had a significantly smaller ($p=0.0218$) increase in myoglobin in the post-run serum compared to the pre-run serum which indicates less muscle damage and loss from the L-carnitine dogs. There was a significant time (post-run minus pre-run) interaction with sex ($p=0.0264$). The female control dogs had a 40.59 ng/mL myoglobin post-run value compared to only 4.68 ng·mL for pre-run control dogs is the key change that produced a time and sex interaction.

Creatine kinase (CK) in the serum for baseline, pre-run and post-run dogs is reported in Table 10.

TABLE 10

Creatine Kinase (mU/mL) for L-carnitine and control dogs using a mixed statistical model

| Term | Estimate | Std Error | DFDen | t Ratio | Prob > \|t\| |
|---|---|---|---|---|---|
| Intercept | 21.762655 | 1.577326 | 95.98 | 13.80 | <.0001* |
| Time[Pre-run-Baseline] | −14.89398 | 2.127842 | 68.82 | −7.00 | <.0001* |
| Time[Post-run-Pre-run] | 11.661206 | 2.234777 | 72.24 | 5.22 | <.0001* |
| Treatment[L-carnitine] | 3.120698 | 1.577326 | 95.98 | 1.98 | 0.0507 |
| Sex[F] | 5.0356025 | 1.577326 | 95.98 | 3.19 | 0.0019* |
| Time[Pre-run-Baseline] * Treatment[L-carnitine] | −3.029114 | 2.127842 | 68.82 | −1.42 | 0.1591 |
| Time[Post-run-Pre-run] * Treatment[L-carnitine] | −2.54442 | 2.234777 | 72.24 | −1.14 | 0.2586 |
| Treatment[L-carnitine] * Sex[F] | 5.9352122 | 1.577326 | 95.98 | 3.76 | 0.0003* |
| Time[Pre-run-Baseline] * Sex[F] | −5.381441 | 2.127842 | 68.82 | −2.53 | 0.0137* |
| Time[Post-run-Pre-run] * Sex[F] | 2.6035867 | 2.234777 | 72.24 | 1.17 | 0.2478 |
| Time[Pre-run-Baseline] * Treatment[L-carnitine] * Sex[F] | −5.661499 | 2.127842 | 68.82 | −2.66 | 0.0097* |
| Time[Post-run-Pre-run] * Treatment[L-carnitine] * Sex[F] | 1.3348877 | 2.234777 | 72.24 | 0.60 | 0.5522 |

Effect Details

| Level | | Least Sq Mean |
|---|---|---|

Creatine Kinase - Time - LSMeans Differences Student's t
α = 0.050

| | | | |
|---|---|---|---|
| Baseline | A | | 21.762655 |
| Post-run | A | | 18.529875 |
| Pre-run | | B | 6.868670 |

TABLE 10-continued

Creatine Kinase (mU/mL) for L-carnitine and control dogs using a mixed statistical model Creatine Kinase - Treatment - LSMeans Differences Student's t
α = 0.050

| | | | | |
|---|---|---|---|---|
| L-carnitine | A | | | 24.883353 |
| Control | A | | | 18.641957 |

Creatine Kinase - Sex - LSMeans Differences Student's t
α = 0.050

| | | | | |
|---|---|---|---|---|
| F | A | | | 26.798257 |
| M | | B | | 16.727052 |

Creatine Kinase - Time * Treatment - LSMeans Differences Student's t
α = 0.050

| | | | | |
|---|---|---|---|---|
| Baseline, L-carnitine | A | | | 24.883353 |
| Post-run, Control | A | B | | 20.982711 |
| Baseline, Control | A | B | | 18.641957 |
| Post-run, L-carnitine | | B | | 16.077039 |
| Pre-run, L-carnitine | | | C | 6.960253 |
| Pre-run, Control | | | C | 6.777086 |

Creatine Kinase - Treatment * Sex - LSMeans Differences Student's t
α = 0.050

| | | | | |
|---|---|---|---|---|
| L-carnitine, F | A | | | 35.854167 |
| Control, M | | B | | 19.541566 |
| Control, F | | B | | 17.742347 |
| L-carnitine, M | | B | | 13.912538 |

Creatine Kinase - Time * Sex - LSMeans Differences Student's t
α = 0.050

| | | | | |
|---|---|---|---|---|
| Baseline, F | A | | | 26.798257 |
| Post-run, F | A | B | | 20.787623 |
| Baseline, M | | B | | 16.727052 |
| Post-run, M | | B | | 16.272127 |
| Pre-run, M | | | C | 7.214508 |
| Pre-run, F | | | C | 6.522831 |

Creatine Kinase - Time * Treatment * Sex - LSMeans Differences Student's t
α = 0.050

| | | | | |
|---|---|---|---|---|
| Baseline, L-carnitine, F | A | | | 35.854167 |
| Post-run, Control, F | | B | | 21.631858 |
| Post-run, Control, M | | B | | 20.333564 |
| Post-run, L-carnitine, F | | B | | 19.943388 |
| Baseline, Control, M | | B | | 19.541566 |
| Baseline, Control, F | | B | | 17.742347 |
| Baseline, L-carnitine, M | | B | C | 13.912538 |
| Post-run, L-carnitine, M | | B | C | 12.210690 |
| Pre-run, Control, M | | | C | 7.396638 |
| Pre-run, L-carnitine, M | | | C | 7.032379 |
| Pre-run, L-carnitine, F | | | C | 6.888128 |
| Pre-run, Control, F | | | C | 6.157534 |

Levels not connected by same letter are significantly different.

The CK values are lower in the pre-run dogs compared to the CK found in dogs prior to the beginning of the study (p<0.0001). The dogs were not as conditioned in the beginning of the study compared to the condition of the dogs prior to the final run. The continual training that occurred prior to the beginning of the study may have caused a higher CK value for the baseline beginning value. The pre-run CK values represent a dog that is resting and the only exercise that occurred during the taper was significantly reduced in length compared to the exercise regimen that was occurring at wk 10. All dogs showed a significant increase (p<0.0001) in post-run CK values compared to pre-run CK values. The overall CK value when considering the baseline, pre-run, and post-run values indicate that L-carnitine dogs were significantly different than the control dogs (p=0.05). The baseline CK L-carnitine dogs were high compared to the control dogs and greatly influenced the value. The higher CK baseline value for the L-carnitine dogs was not a reflection of the treatment other than the L-carnitine dogs were showing muscle damage prior to the beginning of L-carnitine feeding and the beginning of the 90 day study. The female dogs also showed the significant p=0.0019) highest values for the three time points but this difference is also related to the female L-carnitine baseline dogs that were the highest before the study begin. The treatment and sex interaction (p=0.0003) was highly influenced by the CK baseline value for the female L-carnitine dogs that was higher than the control female baseline value.

Table 11 shows the Total Antioxidant Capacity (TAC) for the three time points for each of the test dogs.

TABLE 11

Total Antioxidant capacity for L-carnitine and control dogs using a mixed statistical model

| Term | Estimate | Std Error | DFDen | t Ratio | Prob > \|t\| |
|---|---|---|---|---|---|
| Intercept | 0.1052274 | 0.003034 | 103.1 | 34.69 | <.0001* |
| Time[Pre-run-Baseline] | 0.011405 | 0.003946 | 72 | 2.89 | 0.0051* |
| Time[Post-run-Pre-run] | −0.030493 | 0.003946 | 72 | −7.73 | <.0001* |
| Treatment[L-carnitine] | 0.0013564 | 0.003034 | 103.1 | 0.45 | 0.6557 |
| Sex[F] | −0.001817 | 0.003034 | 103.1 | −0.60 | 0.5506 |
| Time[Pre-run-Baseline] * Treatment[L-carnitine] | −0.00085 | 0.003946 | 72 | −0.22 | 0.8301 |
| Time[Post-run-Pre-run] * Treatment[L-carnitine] | −0.001428 | 0.003946 | 72 | −0.36 | 0.7186 |
| Treatment[L-carnitine] * Sex[F] | 0.0016711 | 0.003034 | 103.1 | 0.55 | 0.5829 |
| Time[Pre-run-Baseline] * Sex[F] | −0.012678 | 0.003946 | 72 | −3.21 | 0.0020* |
| Time[Post-run-Pre-run] * Sex[F] | −0.004465 | 0.003946 | 72 | −1.13 | 0.2616 |
| Time[Pre-run-Baseline] * Treatment[L-carnitine] * Sex[F] | 0.0019577 | 0.003946 | 72 | 0.50 | 0.6214 |
| Time[Post-run-Pre-run] * Treatment[L-carnitine] * Sex[F] | −0.001227 | 0.003946 | 72 | −0.31 | 0.7567 |

Effect Details

| Level | | | | Least Sq Mean |
|---|---|---|---|---|
| *TAC (mM Trolox Equiv) - Time - LSMeans Differences Student's t* $\alpha = 0.050$ | | | | |
| Pre-run | A | | | 0.11663238 |
| Baseline | | B | | 0.10522735 |
| Post-run | | | C | 0.08613891 |
| *TAC (mM Trolox Equiv) - Treatment - LSMeans Differences Student's t* $\alpha = 0.050$ | | | | |
| L-carnitine | A | | | 0.10658377 |
| Control | A | | | 0.10387094 |
| *TAC (mM Trolox Equiv) - Sex - LSMeans Differences Student's t* $\alpha = 0.050$ | | | | |
| M | A | | | 0.10704411 |
| F | A | | | 0.10341060 |
| *TAC (mM Trolox Equiv) - Time * Treatment - LSMeans Differences Student's t* $\alpha = 0.050$ | | | | |
| Pre-run, L-carnitine | A | | | 0.11713904 |
| Pre-run, Control | A | | | 0.11612572 |
| Baseline, L-carnitine | A | B | | 0.10658377 |
| Baseline, Control | | B | | 0.10387094 |
| Post-run, Control | | | C | 0.08705988 |
| Post-run, L-carnitine | | | C | 0.08521795 |
| *TAC (mM Trolox Equiv) - Treatment * Sex - LSMeans Differences Student's t* $\alpha = 0.050$ | | | | |
| Control, M | A | | | 0.10735883 |
| L-carnitine, M | A | | | 0.10672938 |
| L-carnitine, F | A | | | 0.10643815 |
| Control, F | A | | | 0.10038305 |
| *TAC (mM Trolox Equiv) - Time * Sex - LSMeans Differences Student's t* $\alpha = 0.050$ | | | | |
| Pre-run, M | A | | | 0.13112681 |
| Baseline, M | | B | | 0.10704411 |
| Post-run, M | | B | | 0.10509850 |
| Baseline, F | | B | | 0.10341060 |
| Pre-run, F | | B | | 0.10213795 |
| Post-run, F | | | C | 0.06717933 |
| *TAC (mM Trolox Equiv) - Time * Treatment * Sex - LSMeans Differences Student's t* $\alpha = 0.050$ | | | | |
| Pre-run, Control, M | A | | | 0.13424895 |
| Pre-run, L-carnitine, M | A | | | 0.12800467 |
| Post-run, Control, M | | B | | 0.10842089 |
| Baseline, Control, M | | B | | 0.10735883 |
| Baseline, L-carnitine, M | | B | | 0.10672938 |
| Baseline, L-carnitine, F | | B | | 0.10643815 |
| Pre-run, L-carnitine, F | | B | | 0.10627341 |
| Post-run, L-carnitine, M | | B | | 0.10177610 |
| Baseline, Control, F | | B | | 0.10038305 |
| Pre-run, Control, F | | B | | 0.09800250 |
| Post-run, L-carnitine, F | | | C | 0.06865980 |
| Post-run, Control, F | | | C | 0.06569886 |

Levels not connected by same letter are significantly different.

The dogs going through the 13 wk performance study actually increased the TAC from their baseline values to the pre-run TAC. The TAC data correlates to the CK values in that both tended to show that as the dogs went through the 13 wk study they become increasingly more fit with more TAC compared to the beginning of the study. The CK for the test dogs showed the same thing when comparing the baseline to the pre-run serum values for all dogs. The TAC decreased following the final long run for both groups compared to the pre-run TAC values ($p<0.0001$) which is showing the dogs are having to use the antioxidant capacity to deal with the oxidative stress that is involved in running the 15 mile final run. The female had less TAC increase between the baseline dog serum values and the pre-run values compared to the male dogs because the female put out consistently more effort during the course of the 13 wk study. L-carnitine did not have a significant effect on changing the TAC of the test dogs during the study.

The TBARS for the test dogs was determined for the baseline, pre-run and post-run time periods (Table 12).

TABLE 12

TBARS for L-carnitine and control dogs using a mixed statistical model

| Term | Estimate | Std Error | DFDen | t Ratio | Prob > \|t\| |
|---|---|---|---|---|---|
| Intercept | 13.054293 | 0.682261 | 91.5 | 19.13 | <.0001* |
| Time[Pre-run-Baseline] | −0.904966 | 0.807078 | 72 | −1.12 | 0.2659 |
| Time[Post-run-Pre-run] | 1.2553451 | 0.807078 | 72 | 1.56 | 0.1242 |
| Treatment[L-carnitine] | −0.522186 | 0.682261 | 91.5 | −0.77 | 0.4460 |
| Sex[F] | 1.1679293 | 0.682261 | 91.5 | 1.71 | 0.0903 |
| Time[Pre-run-Baseline] * Treatment[L-carnitine] | 0.8243747 | 0.807078 | 72 | 1.02 | 0.3105 |
| Time[Post-run-Pre-run] * Treatment[L-carnitine] | −0.942971 | 0.807078 | 72 | −1.17 | 0.2465 |
| Treatment[L-carnitine] * Sex[F] | 0.4031385 | 0.682261 | 91.5 | 0.59 | 0.5561 |
| Time[Pre-run-Baseline] * Sex[F] | 0.90867 | 0.807078 | 72 | 1.13 | 0.2640 |
| Time[Post-run-Pre-run] * Sex[F] | −0.217382 | 0.807078 | 72 | −0.27 | 0.7884 |
| Time[Pre-run-Baseline] * Treatment[L-carnitine] * Sex[F] | 0.2020803 | 0.807078 | 72 | 0.25 | 0.8030 |
| Time[Post-run-Pre-run] * Treatment[L-carnitine] * Sex[F] | −0.763047 | 0.807078 | 72 | −0.95 | 0.3476 |

Effect Details

| Level | | | | | Least Sq Mean |
|---|---|---|---|---|---|
| TBARS (μM MDA) - Time - LSMeans Differences Student's t $\alpha = 0.050$ | | | | | |
| Post-run | A | | | | 13.404672 |
| Baseline | A | | | | 13.054293 |
| Pre-run | A | | | | 12.149327 |
| TBARS (μM MDA) - Treatment - LSMeans Differences Student's t $\alpha = 0.050$ | | | | | |
| Control | A | | | | 13.576479 |
| L-carnitine | A | | | | 12.532107 |
| TBARS (μM MDA) - Sex - LSMeans Differences Student's t $\alpha = 0.050$ | | | | | |
| F | A | | | | 14.222222 |
| M | A | | | | 11.886364 |
| TBARS (μM MDA) - Time * Treatment - LSMeans Differences Student's t $\alpha = 0.050$ | | | | | |
| Post-run, Control | A | | | | 14.045455 |
| Baseline, Control | A | | | | 13.576479 |
| Post-run, L-carnitine | A | | | | 12.763889 |
| Baseline, L-carnitine | A | | | | 12.532107 |
| Pre-run, L-carnitine | A | | | | 12.451515 |
| Pre-run, Control | A | | | | 11.847138 |
| TBARS (μM MDA) - Treatment * Sex - LSMeans Differences Student's t $\alpha = 0.050$ | | | | | |
| Control, F | A | | | | 14.341270 |
| L-carnitine, F | A | | | | 14.103175 |
| Control, M | A | | | | 12.811688 |
| L-carnitine, M | A | | | | 10.961039 |
| TBARS (μM MDA) - Time * Sex - LSMeans Differences Student's t $\alpha = 0.050$ | | | | | |
| Post-run, F | A | | | | 15.263889 |
| Pre-run, F | A | B | | | 14.225926 |
| Baseline, F | A | B | | | 14.222222 |
| Baseline, M | | B | C | | 11.886364 |
| Post-run, M | | B | C | | 11.545455 |
| Pre-run, M | | | C | | 10.072727 |

TABLE 12-continued

TBARS for L-carnitine and control dogs using a mixed statistical model

TBARS (µM MDA) - Time * Treatment * Sex - LSMeans Differences Student's t
α = 0.050

| | | | | | | |
|---|---|---|---|---|---|---|
| Post-run, Control, F | A | | | | | 16.062500 |
| Pre-run, L-carnitine, F | A | B | | | | 15.133333 |
| Post-run, L-carnitine, F | A | B | C | | | 14.465278 |
| Baseline, Control, F | A | B | C | | | 14.341270 |
| Baseline, L-carnitine, F | A | B | C | D | | 14.103175 |
| Pre-run, Control, F | A | B | C | D | E | 13.318519 |
| Baseline, Control, M | A | B | C | D | E | 12.811688 |
| Post-run, Control, M | | B | C | D | E | 12.028409 |
| Post-run, L-carnitine, M | | | C | D | E | 11.062500 |
| Baseline, L-carnitine, M | | | C | D | E | 10.961039 |
| Pre-run, Control, M | | | | D | E | 10.375758 |
| Pre-run, L-carnitine, M | | | | | E | 9.769697 |

Levels not connected by same letter are significantly different.

The mixed model indicates that the female dogs showed a numerical increase (p=0.09) in TBARS compared to the male dogs for the three time periods but did not show anything significant for the treatment effects or interactions. The mixed model also shows that the post-run values were numerically higher than pre-run values for all groups of dogs (p=0.12) indicating lipid peroxidation took place during the oxidative stress of the final long run and the lipid products were degraded into Malondialdehyde (MDA) for an increase in TBARS. The female increase in TBARS indicates more lipid degradation of membranes and also fits the significant increase in myoglobin following the final run.

Table 13 shows the individual change in post-run from the pre-run of the blood biomarkers that have been discussed.

TABLE 13

Pre-run and post-run change in blood biomarkers for L-carnitine and control dogs using a standard unpaired Student T-test.
Change in Blood Chemistry following 15 mile long run at 13 wk

| | L-carnitine | Control | P-Value |
|---|---|---|---|
| TAC (mM Trolox Equiv) | −0.03 ± 0.01 n = 20 | −0.03 ± 0.01 n = 20 | 0.7709 |
| ♂ | −0.03 ± 0.01 n = 11 | −0.03 ± 0.01 n = 11 | 0.9765 |
| ♀ | −0.04 ± 0.01 n = 9 | −0.03 ± 0.01 n = 9 | 0.6496 |
| TBARS (µM MDA) | 0.41 ± 0.71 n = 20 | 2.14 ± 0.96 n = 20 | 0.1552 |
| ♂ | 1.3 ± 0.9 n = 11 | 1.7 ± 0.4 n = 11 | 0.7184 |
| ♀ | −0.7 ± 1.1 n = 9 | 2.7 ± 2.1 n = 9 | 0.1727 |
| Myoglobin (ng/mL) | 6.69$^A$ ± 2.7 n = 16 | 24.02$^B$ ± 6.59 n = 19 | 0.0295 |
| ♂ | 7.04 ± 3.9 n = 10 | 13.91 ± 6.74 n = 11 | 0.4008 |
| ♀ | 6.11 ± 3.51 n = 6 | 37.91 ± 11.34 n = 8 | 0.0371 |
| Creatine Kinase Activity | 9.3 ± 1.86 n = 18 | 13.64 ± 2.28 n = 15 | 0.1452 |
| ♂ | 5.54 ± 2.63 n = 9 | 12.94 ± 2.4 n = 11 | 0.0522 |
| ♀ | 13.06 ± 2.06 n = 9 | 15.58 ± 6.03 n = 4 | 0.6185 |

Unpaired t-test. Data displayed indicates mean ± SEM. Hemolyzed samples were excluded from CK analysis. Differing letters indicates significant difference (P < 0.05).

The data does not consider the baseline information that was evaluated in the mixed model data in previous tables. Table 13 mainly shows that the TBARS and creatine kinase are numerically increased in individual dogs for the post-run compared to the pre-run. The change in blood biomarkers allows the individual dogs to be taken into account and supports that L-carnitine is helping minimize the muscle damage during the run and also helps keep down peroxidation of membranes due to the stress involved with the final run.

The mixed model was used for the mean values for gender differences and comparing treatments and time periods but the mixed model could not be used for comparing the actual change for each dog between time periods for the different groups. The TBARS increases 2.14 for the male and female control dogs following the long final run compared to pre-run values and the L-carnitine dogs only showed an increase of 0.41 for the same two periods (p=0.155). The CK values increase 13.64 in control dogs comparing post-run serum values to pre-run CK whereas the CK only increases 9.3 enzyme units for the L-carnitine dogs (p=0.145). The male control dogs tended to show more CK increase in post-run serum values (12.94 units) reflecting muscle damage compared to the L-carnitine male dogs only having a 5.54 unit increase (p=0.052). The L-carnitine male dogs showed less increase in CK compared to the control males and also less CK than both female treatments.

Myoglobin as a biomarker for muscle damage indicated the control female had the largest increase in muscle damage during the long run compared to the L-carnitine female (p=0.03). The biomarkers show that both male and female L-carnitine dogs had less muscle damage during the final long run. The myoglobin values were best for seeing less muscle damage in females consuming L-carnitine whereas the CK values were best for describing less muscle damage for male dogs consuming L-carnitine.

The body composition for the performance dogs is shown in Table 14.

TABLE 14

Body composition of dogs in L-carnitine and control groups using a mixed statistical model.

| | | Treatment | | | | | | | | | | | | |
|---|---|---|---|---|---|---|---|---|---|---|---|---|---|---|
| | | L-carnitine | | | | | | Control | | | | | | |
| | | Time | | | | | | Time | | | | | | |
| | | Initial | | | Final | | | Initial | | | Final | | | |
| Measurement | | N | Mean | Std Err | N | Mean | Std Err | N | Mean | Std Err | N | Mean | Std Err |
| Total Mass (lb) | | 18 | 56.3 | 1.7 | 20 | 58.8 | 1.7 | 19 | 56.3 | 1.6 | 20 | 61.3 | 1.8 |
| Lean Mass (lb) | | 18 | 50.3 | 1.6 | 20 | 50.3 | 1.5 | 19 | 50.6 | 1.6 | 20 | 51.7 | 1.8 |
| % Fat | | 18 | 10.6 | 1.3 | 20 | 14.3 | 1.4 | 19 | 10.2 | 1.2 | 20 | 15.7 | 1.4 |
| BMC (g) | | 18 | 787 | 49 | 20 | 866 | 26 | 19 | 833 | 29 | 20 | 902 | 31 |
| Sex | | | | | | | | | | | | | |
| F | Total Mass (lb) | 7 | 50.8 | 0.9 | 9 | 54.5 | 1.4 | 9 | 50.5 | 1.6 | 9 | 56.4 | 2.8 |
| | Lean Mass (lb) | 7 | 44.7 | 1.4 | 9 | 45.6 | 1.7 | 9 | 45.4 | 1.7 | 9 | 45.3 | 2.0 |
| | % Fat | 7 | 12.1 | 2.2 | 9 | 16.3 | 2.2 | 9 | 10.2 | 2.0 | 9 | 19.1 | 2.5 |
| | BMC (g) | 7 | 764 | 23 | 9 | 820 | 19 | 9 | 737 | 33 | 9 | 811 | 41 |
| M | Total Mass (lb) | 11 | 59.8 | 2.2 | 11 | 62.3 | 2.6 | 10 | 61.5 | 1.4 | 11 | 65.3 | 1.6 |
| | Lean Mass (lb) | 11 | 53.9 | 1.8 | 11 | 54.0 | 1.7 | 10 | 55.2 | 1.5 | 11 | 56.9 | 1.5 |
| | % Fat | 11 | 9.6 | 1.6 | 11 | 12.7 | 1.6 | 10 | 10.2 | 1.4 | 11 | 12.8 | 1.0 |
| | BMC (g) | 11 | 802 | 80 | 11 | 903 | 42 | 10 | 919 | 26 | 11 | 976 | 30 |

The total mass (lbs), lean mass (lbs), percent fat, and g Body Mineral Content (BMC) are reported by sex, treatment, and time for the study.

Table 15 shows the total body mass for the test dogs using a mixed statistical model for evaluation.

TABLE 15

Total Body Mass for L-carnitine and control dogs using a mixed statistical model

| Term | Estimate | Std Error | DFDen | t Ratio | Prob > \|t\| |
|---|---|---|---|---|---|
| Intercept | 55.838881 | 0.990252 | 43.3 | 56.39 | <.0001* |
| Treatment[L-carnitine] | −0.353569 | 0.990252 | 43.3 | −0.36 | 0.7228 |
| Sex[F] | −4.998872 | 0.990252 | 43.3 | −5.05 | <.0001* |
| Time[Final-Initial] | 3.7762401 | 0.55147 | 33.73 | 6.85 | <.0001* |
| Treatment[L-carnitine] * Sex[F] | 0.6569114 | 0.990252 | 43.3 | 0.66 | 0.5106 |
| Treatment[L-carnitine] * Time[Final-Initial] | −0.872385 | 0.55147 | 33.73 | −1.58 | 0.1230 |
| Sex[F] * Time[Final-Initial] | 0.8275844 | 0.55147 | 33.73 | 1.50 | 0.1427 |
| Treatment[L-carnitine] * Sex[F] * Time[Final-Initial] | −0.365457 | 0.55147 | 33.73 | −0.66 | 0.5120 |

| Level | | Least Sq Mean |
|---|---|---|

Total Mass (lb) - Treatment - LSMeans Differences Student's t
α = 0.050

| Control | A | 56.192450 |
|---|---|---|
| L-carnitine | A | 55.485312 |

Total Mass (lb) - Sex - LSMeans Differences Student's t
α = 0.050

| M | A | 60.837753 |
|---|---|---|
| F | B | 50.840009 |

Total Mass (lb) - Time - LSMeans Differences Student's t
α = 0.050

| Final | A | 59.615121 |
|---|---|---|
| Initial | B | 55.838881 |

Total Mass (lbs) - Treatment * Sex - LSMeans Differences Student's t
α = 0.050

| Control, M | A | 61.848234 |
|---|---|---|
| L-carnitine, M | A | 59.827273 |

TABLE 15-continued

Total Body Mass for L-carnitine and control dogs using a mixed statistical model

| | | | | | | | |
|---|---|---|---|---|---|---|---|
| L-carnitine, F | | B | | | | | 51.143351 |
| Control, F | | B | | | | | 50.536667 |

Total Mass (lbs) - Treatment * Time - LSMeans Differences Student's t
$\alpha = 0.050$

| | | | | | | | |
|---|---|---|---|---|---|---|---|
| Control, Final | A | | | | | | 60.841076 |
| L-carnitine, Final | A | B | | | | | 58.389167 |
| Control, Initial | | B | C | | | | 56.192450 |
| L-carnitine, Initial | | | C | | | | 55.485312 |

Total Mass (lbs) - Sex * Time - LSMeans Differences Student's t
$\alpha = 0.050$

| | | | | | | | |
|---|---|---|---|---|---|---|---|
| M, Final | A | | | | | | 63.786409 |
| M, Initial | | B | | | | | 60.837753 |
| F, Final | | | C | | | | 55.443833 |
| F, Initial | | | | D | | | 50.840009 |

Total Mass (lbs) - Treatment * Sex * Time - LSMeans Differences Student's t
$\alpha = 0.050$

| | | | | | | | |
|---|---|---|---|---|---|---|---|
| Control, M, Final | A | | | | | | 65.303818 |
| L-carnitine, M, Final | A | B | | | | | 62.269000 |
| Control, M, Initial | | B | C | | | | 61.848234 |
| L-carnitine, M, Initial | | | C | D | | | 59.827273 |
| Control, F, Final | | | C | D | E | | 56.378333 |
| L-carnitine, F, Final | | | | D | | F | 54.509333 |
| L-carnitine, F, Initial | | | | | E | | G | 51.143351 |
| Control, F, Initial | | | | | | F | G | 50.536667 |

Levels not connected by same letter are significantly different.

There was a statistical difference in total body mass for sex ($p<0.0001$) with the females containing less body mass. There was a statistical significant increase ($p<0.0001$) in total body mass for all of the dogs but there was no significant difference for treatments. The female L-carnitine dogs had a numerical lower total body mass gain from the beginning until after the final run compared to the control female dogs ($p=0.123$). The overall total mass gain of the female was numerically higher than observed for the male dogs during the study although the gain was not significant ($p=0.147$). The female total mass gain was proportionally higher in fat gain.

An increase in fat percentage ($p<0.0001$) occurred for all dogs (Table 16).

TABLE 16

Fat percentage of L-carnitine and control dogs using a mixed statistical model.

| Term | Estimate | Std Error | DFDen | t Ratio | Prob > \|t\| |
|---|---|---|---|---|---|
| Intercept | 10.149735 | 0.918937 | 51.42 | 11.05 | <.0001* |
| Treatment[L-carnitine] | 0.1572755 | 0.918937 | 51.42 | 0.17 | 0.8648 |
| Sex[F] | 0.4441442 | 0.918937 | 51.42 | 0.48 | 0.6309 |
| Time[Final-Initial] | 5.1045581 | 0.765819 | 33.04 | 6.67 | <.0001* |
| Treatment[L-carnitine] * Sex[F] | 0.2810479 | 0.918937 | 51.42 | 0.31 | 0.7610 |
| Treatment[L-carnitine] * Time[Final-Initial] | −0.886821 | 0.765819 | 33.04 | −1.16 | 0.2552 |
| Sex[F] * Time[Final-Initial] | 2.0237851 | 0.765819 | 33.04 | 2.64 | 0.0125* |
| Treatment[L-carnitine] * Sex[F] * Time[Final-Initial] | −0.951502 | 0.765819 | 33.04 | −1.24 | 0.2228 |

| Level | | | Least Sq Mean |
|---|---|---|---|

Fat Percentage - Treatment - LSMeans Differences Student's t
$\alpha = 0.050$

| | | | |
|---|---|---|---|
| L-carnitine | A | | 10.307010 |
| Control | A | | 9.992459 |

Fat Percentage - Sex - LSMeans Differences Student's t
$\alpha = 0.050$

| | | | |
|---|---|---|---|
| F | A | | 10.593879 |
| M | A | | 9.705591 |

Fat Percentage - Time - LSMeans Differences Student's t
$\alpha = 0.050$

| | | | |
|---|---|---|---|
| Final | A | | 15.254293 |
| Initial | | B | 10.149735 |

TABLE 16-continued

Fat percentage of L-carnitine and control dogs using a mixed statistical model.

Fat Percentage - Treatment * Sex - LSMeans Differences Student's t
α = 0.050

| | | | | | | |
|---|---|---|---|---|---|---|
| L-carnitine, F | A | | | | | 11.032202 |
| Control, F | A | | | | | 10.155556 |
| Control, M | A | | | | | 9.829363 |
| L-carnitine, M | A | | | | | 9.581818 |

Fat Percentage - Treatment * Time - LSMeans Differences Student's t
α = 0.050

| | | | | | | |
|---|---|---|---|---|---|---|
| Control, Final | A | | | | | 15.983838 |
| L-carnitine, Final | A | | | | | 14.524747 |
| L-carnitine, Initial | | B | | | | 10.307010 |
| Control, Initial | | B | | | | 9.992459 |

Fat Percentage - Sex * Time - LSMeans Differences Student's t
α = 0.050

| | | | | | | |
|---|---|---|---|---|---|---|
| F, Final | A | | | | | 17.722222 |
| M, Final | | B | | | | 12.786364 |
| F, Initial | | B | C | | | 10.593879 |
| M, Initial | | | C | | | 9.705591 |

Fat Percentage - Treatment * Sex * Time - LSMeans Differences Student's t
α = 0.050

| | | | | | | |
|---|---|---|---|---|---|---|
| Control, F, Final | A | | | | | 19.122222 |
| L-carnitine, F, Final | A | B | | | | 16.322222 |
| Control, M, Final | | B | C | | E | 12.845455 |
| L-carnitine, M, Final | | B | C | D | | 12.727273 |
| L-carnitine, F, Initial | | | C | D | E | F | 11.032202 |
| Control, F, Initial | | | C | D | E | F | 10.155556 |
| Control, M, Initial | | | | D | | F | 9.829363 |
| L-carnitine, M, Initial | | | | | E | F | 9.581818 |

Levels not connected by same letter are significantly different.

The female dogs increased fat percentage significantly (p=0.0125) during the study compared to the male dogs. The L-carnitine dogs of both sexes showed a numerical lower increase (p=0.255) in fat percentage with the female L-carnitine dogs producing a lower increase (p=0.22) in fat percentage compared to the control female dogs. The fat mass data also indicates that all dogs contained less fat mass in the beginning of the study compared to final fat mass (Table 17).

TABLE 17

Fat mass for the L-carnitine and control dogs using a mixed statistical model.

| Term | Estimate | Std Error | DFDen | t Ratio | Prob > \|t\| |
|---|---|---|---|---|---|
| Intercept | 7.4232892 | 0.509979 | 35.52 | 14.56 | <.0001* |
| Treatment[L-carnitine] | −0.254557 | 0.509979 | 35.52 | −0.50 | 0.6207 |
| Sex[F] | 0.268857 | 0.509979 | 35.52 | 0.53 | 0.6013 |
| Time[Initial] | −1.730519 | 0.256803 | 33.55 | −6.74 | <.0001* |
| Treatment[L-carnitine] * Sex[F] | −0.176352 | 0.509979 | 35.52 | −0.35 | 0.7315 |
| Treatment[L-carnitine] * Time[Initial] | 0.3408267 | 0.256803 | 33.55 | 1.33 | 0.1934 |
| Sex[F] * Time[Initial] | −0.571724 | 0.256803 | 33.55 | −2.23 | 0.0328* |
| Treatment[L-carnitine] * Sex[F] * Time[Initial] | 0.3309862 | 0.256803 | 33.55 | 1.29 | 0.2063 |

| Level | | | Least Sq Mean |
|---|---|---|---|

Fat (lbs) - Treatment - LSMeans Differences Student's t
α = 0.050

| | | | |
|---|---|---|---|
| Control | A | | 7.6778464 |
| L-carnitine | A | | 7.1687321 |

Fat (lbs) - Sex - LSMeans Differences Student's t
α = 0.050

| | | | |
|---|---|---|---|
| F | A | | 7.6921462 |
| M | A | | 7.1544322 |

Fat (lbs) - Time - LSMeans Differences Student's t
α = 0.050

| | | | |
|---|---|---|---|
| Final | A | | 9.1538081 |
| Initial | | B | 5.6927704 |

TABLE 17-continued

Fat mass for the L-carnitine and control dogs using a mixed statistical model.

Fat (lbs) - Treatment * Sex - LSMeans Differences Student's t
α = 0.050

| | | | | | | | |
|---|---|---|---|---|---|---|---|
| Control, F | A | | | | | | 8.1230556 |
| L-carnitine, F | A | | | | | | 7.2612369 |
| Control, M | A | | | | | | 7.2326372 |
| L-carnitine, M | A | | | | | | 7.0762273 |

Fat (lbs) - Treatment * Time - LSMeans Differences Student's t
α = 0.050

| | | | | | | | |
|---|---|---|---|---|---|---|---|
| Control, Final | A | | | | | | 9.7491919 |
| L-carnitine, Final | A | | | | | | 8.5584242 |
| L-carnitine, Initial | | B | | | | | 5.7790399 |
| Control, Initial | | B | | | | | 5.6065008 |

Fat (lbs) - Sex * Time - LSMeans Differences Student's t
α = 0.050

| | | | | | | | |
|---|---|---|---|---|---|---|---|
| F, Final | A | | | | | | 9.9943889 |
| M, Final | A | | | | | | 8.3132273 |
| M, Initial | | B | | | | | 5.9956372 |
| F, Initial | | B | | | | | 5.3899036 |

Fat (lbs) - Treatment * Sex * Time - LSMeans Differences Student's t
α = 0.050

| | | | | | | | |
|---|---|---|---|---|---|---|---|
| Control, F, Final | A | | | | | | 11.097111 |
| L-carnitine, F, Final | A | B | C | | E | | 8.891667 |
| Control, M, Final | A | | C | D | | F | 8.401273 |
| L-carnitine, M, Final | A | B | | D | | | G | 8.225182 |
| Control, M, Initial | | B | | | E | | G | 6.064002 |
| L-carnitine, M, Initial | | | C | | E | F | | 5.927273 |
| L-carnitine, F, Initial | | | | D | | F | G | 5.630807 |
| Control, F, Initial | | | | | | | G | 5.149000 |

Levels not connected by same letter are significantly different.

The fat mass of all female dogs at the beginning of the study was significantly less (p=0.03) than found in the male dogs. Both sexes of L-carnitine dogs had a numerical higher fat mass (p=0.19) compared to the control dogs at the beginning of the study. The L-carnitine female dogs also contained a numerical higher amount of fat mass (p=0.20) compared to the female control dogs at the beginning.

Table 18 shows that the lean mass (lbs) is significantly lower for females than for males (p<0.0001) and that females showed a numerical lower gain (p=0.1576) in lean mass from beginning to the end of the study compared to males during the study. There was no effect of treatment on lean mass during the study.

TABLE 18

Lean mass for the L-carnitine and control dogs using a mixed statistical model.

| Term | Estimate | Std Error | DFDen | t Ratio | Prob > \|t\| |
|---|---|---|---|---|---|
| Intercept | 50.261692 | 0.852688 | 37.82 | 58.95 | <.0001* |
| Treatment[L-carnitine] | −0.396561 | 0.852688 | 37.82 | −0.47 | 0.6445 |
| Sex[F] | −4.652737 | 0.852688 | 37.82 | −5.46 | <.0001* |
| Time[Final-Initial] | 0.1996088 | 0.248293 | 33.07 | 0.80 | 0.4272 |
| Treatment[L-carnitine] * Sex[F] | 0.6179594 | 0.852688 | 37.82 | 0.72 | 0.4731 |
| Treatment[L-carnitine] * Time[Final-Initial] | −0.234043 | 0.248293 | 33.07 | −0.94 | 0.3527 |
| Sex[F] * Time[Final-Initial] | −0.359008 | 0.248293 | 33.07 | −1.45 | 0.1576 |
| Treatment[L-carnitine] * Sex[F] * Time[Final-Initial] | 0.1807552 | 0.248293 | 33.07 | 0.73 | 0.4717 |

| Level | | Least Sq Mean |
|---|---|---|

Lean Mass (lbs) - Treatment - LSMeans Differences Student's t
α = 0.050

| | | |
|---|---|---|
| Control | A | 50.658252 |
| L-carnitine | A | 49.865131 |

Lean Mass (lbs) - Sex - LSMeans Differences Student's t
α = 0.050

| | | |
|---|---|---|
| M | A | 54.914429 |
| F | B | 45.608954 |

TABLE 18-continued

Lean mass for the L-carnitine and control dogs using a mixed statistical model.

Lean Mass (lbs) - Time - LSMeans Differences Student's t
α = 0.050

| | | | | |
|---|---|---|---|---|
| Final | A | | | 50.461301 |
| Initial | A | | | 50.261692 |

Lean Mass (lbs) - Treatment * Sex - LSMeans Differences Student's t
α = 0.050

| | | | | |
|---|---|---|---|---|
| Control, M | A | | | 55.928949 |
| L-carnitine, M | A | | | 53.899909 |
| L-carnitine, F | | B | | 45.830353 |
| Control, F | | B | | 45.387556 |

Lean Mass (lbs) - Treatment * Time - LSMeans Differences Student's t
α = 0.050

| | | | | |
|---|---|---|---|---|
| Control, Final | A | | | 51.091904 |
| Control, Initial | A | | | 50.658252 |
| L-carnitine, Initial | A | | | 49.865131 |
| L-carnitine, Final | A | | | 49.830697 |

Lean Mass (lbs) - Sex * Time - LSMeans Differences Student's t
α = 0.050

| | | | | |
|---|---|---|---|---|
| M, Final | A | | | 55.473045 |
| M, Initial | A | | | 54.914429 |
| F, Initial | | B | | 45.608954 |
| F, Final | | B | | 45.449556 |

Lean Mass (lbs) - Treatment * Sex * Time - LSMeans Differences Student's t
α = 0.050

| | | | | |
|---|---|---|---|---|
| Control, M, Final | A | | | 56.902364 |
| Control, M, Initial | A | B | | 55.928949 |
| L-carnitine, M, Final | A | B | | 54.043727 |
| L-carnitine, M, Initial | A | B | | 53.899909 |
| L-carnitine, F, Initial | | | C | 45.830353 |
| L-carnitine, F, Final | | | C | 45.617667 |
| Control, F, Initial | | | C | 45.387556 |
| Control, F, Final | | | C | 45.281444 |

Levels not connected by same letter are significantly different.

The female dogs contained significantly less (p=0.0179) body mineral content (BMC) than the male dogs but both males and females gained a significant (p=0.0085) amount of BMC during the course of the study (Table 19).

TABLE 19

Body mineral content (BMC) of L-carnitine and control dogs using a mixed statistical model.

| Term | Estimate | Std Error | DFDen | t Ratio | Prob > \|t\| |
|---|---|---|---|---|---|
| Intercept | 807.02467 | 22.75191 | 63.62 | 35.47 | <.00001* |
| Treatment[L-carnitine] | −22.84926 | 22.75191 | 63.62 | −1.00 | 0.3190 |
| Sex[F] | −55.28613 | 22.75191 | 63.62 | −2.43 | 0.0179* |
| Time[Final-Initial] | 70.623055 | 25.3341 | 35.7 | 2.79 | 0.0085* |
| Treatment[L-carnitine] * Sex[F] | 37.643359 | 22.75191 | 63.62 | 1.65 | 0.1029 |
| Treatment[L-carnitine] * Time[Final-Initial] | 6.7621359 | 25.3341 | 35.7 | 0.27 | 0.7911 |
| Sex[F] * Time[Final-Initial] | −6.561601 | 25.3341 | 35.7 | −0.26 | 0.7971 |
| Treatment[L-carnitine] * Sex[F] * Time[Final-Initial] | −17.18957 | 25.3341 | 35.7 | −0.68 | 0.5018 |

| Level | | | Least Sq Mean |
|---|---|---|---|

BMC (g) - Treatment - LSMeans Differences Student's t
α = 0.050

| | | | |
|---|---|---|---|
| Control | A | | 829.87393 |
| L-carnitine | A | | 784.17541 |

BMC (g) - Sex - LSMeans Differences Student's t
α = 0.050

| | | | |
|---|---|---|---|
| M | A | | 862.31080 |
| F | | B | 751.73855 |

TABLE 19-continued

Body mineral content (BMC) of L-carnitine and control dogs using a mixed statistical model.

BMC (g) - Time - LSMeans Differences Student's t
α = 0.050

| | | | |
|---|---|---|---|
| Final | A | | 877.64773 |
| Initial | | B | 807.02467 |

BMC (g) - Treatment * Sex - LSMeans Differences Student's t
α = 0.050

| | | | |
|---|---|---|---|
| Control, M | A | | 922.80341 |
| L-carnitine, M | | B | 801.81818 |
| L-carnitine, F | | B | 766.53265 |
| Control, F | | B | 736.94444 |

BMC (g) - Treatment * Time - LSMeans Differences Student's t
α = 0.050

| | | | |
|---|---|---|---|
| Control, Final | A | | 893.73485 |
| L-carnitine, Final | A | | 861.56061 |
| Control, Initial | A | B | 829.87393 |
| L-carnitine, Initial | | B | 784.17541 |

BMC (g) - Sex * Time - LSMeans Differences Student's t
α = 0.050

| | | | | |
|---|---|---|---|---|
| M, Final | A | | | 939.49545 |
| M, Initial | | B | | 862.31080 |
| F, Final | | B | C | 815.80000 |
| F, Initial | | | C | 751.73855 |

BMC (g) - Treatment * Sex * Time - LSMeans Differences Student's t
α = 0.050

| | | | | |
|---|---|---|---|---|
| Control, M, Final | A | | | 976.03636 |
| Control, M, Initial | A | B | | 922.80341 |
| L-carnitine, M, Final | A | B | | 902.95455 |
| L-carnitine, F, Final | | B | C | 820.16667 |
| Control, F, Final | | B | C | 811.43333 |
| L-carnitine, M, Initial | | | C | 801.81818 |
| L-carnitine, F, Initial | | | C | 766.53265 |
| Control, F, Initial | | | C | 736.94444 |

Levels not connected by same letter are significantly different.

The L-carnitine female dogs contained an average higher numerical (p=0.1029) concentration of BMC for the pre-study scan and the post-run scan compared to female control dogs in the study.

Table 20 compares the statistical difference of the body composition of each treatment and for sex within each treatment for the initial body composition, final body composition, and change of body composition components during the course of the study by an unpaired t-test. Table 20 also compares the change from the beginning until the end for each parameter measured for body composition. The female L-carnitine dogs showed a smaller numerical (p=0.30) increase in fat (5.8% vs 9%) compared to the control female dogs during the course of the 90 day study. The fat mass was also numerically less (8.9 lbs vs 11.1 lbs) at the end of the study for the L-carnitine female dogs compared to the control dogs (p=0.29).

TABLE 20

Body composition change for L-carnitine and control dogs from beginning to completion of study.
Body Composition

| | L-carnitine | Control | P-Value |
|---|---|---|---|
| Fat-Initial (%) | 10.6 ± 1.3 n = 18 | 10.2 ± 1.2 n = 19 | 0.816 |
| ♂ | 9.6 ± 1.6 n = 11 | 10.2 ± 1.4 n = 10 | 0.7918 |
| ♀ | 12.1 ± 2.2 n = 7 | 10.2 ± 2 n = 9 | 0.5239 |
| Fat-Final (%) | 14.3 ± 1.4 n = 20 | 15.7 ± 1.4 n = 20 | 0.504 |
| ♂ | 12.7 ± 1.6 n = 11 | 12.8 ± 1 n = 11 | 0.9505 |
| ♀ | 16.3 ± 2.2 n = 9 | 19.1 ± 2.5 n = 9 | 0.4183 |

TABLE 20-continued

Body composition change for L-carnitine and control dogs from beginning to completion of study.
Body Composition

| | L-carnitine | Control | P-Value |
|---|---|---|---|
| Fat-Change (%) | 4.2 ± 0.8 n = 18 | 5.9 ± 1.4 n = 19 | 0.3017 |
| ♂ | 3.1 ± 1.1 n = 11 | 3.2 ± 1 n = 10 | 0.9812 |
| ♀ | 5.8 ± 1.2 n = 7 | 9 ± 2.4 n = 9 | 0.3086 |
| Fat-Initial (lb) | 6 ± 0.8 n = 18 | 5.7 ± 0.7 n = 19 | 0.7832 |
| ♂ | 5.9 ± 1.1 n = 11 | 6.2 ± 0.9 n = 10 | 0.8332 |
| ♀ | 6.1 ± 1.1 n = 7 | 5.1 ± 1 n = 9 | 0.5275 |
| Fat-Final (lb) | 8.5 ± 0.9 n = 20 | 9.6 ± 0.8 n = 20 | 0.3757 |
| ♂ | 8.2 ± 1.3 n = 11 | 8.4 ± 0.7 n = 11 | 0.904 |
| ♀ | 8.9 ± 1.2 n = 9 | 11.1 ± 1.6 n = 9 | 0.2918 |
| Fat-Change (lb) | 2.8 ± 0.5 n = 18 | 3.7 ± 0.9 n = 18 | 0.3959 |
| ♂ | 2.3 ± 0.7 n = 11 | 2.8 ± 0.7 n = 11 | 0.6044 |
| ♀ | 3.6 ± 0.8 n = 7 | 5 ± 1.9 n = 7 | 0.5059 |
| Lean Mass-Initial (lb) | 50.2 ± 1.5 n = 20 | 51.1 ± 1.6 n = 20 | 0.6707 |
| ♂ | 53.9 ± 1.8 n = 11 | 55.8 ± 1.5 n = 11 | 0.4137 |
| ♀ | 45.7 ± 1.3 n = 9 | 45.4 ± 1.7 n = 9 | 0.9015 |
| Lean Mass-Final (lb) | 50.3 ± 1.5 n = 20 | 51.7 ± 1.8 n = 20 | 0.5518 |
| ♂ | 54 ± 1.7 n = 11 | 56.9 ± 1.5 n = 11 | 0.2325 |
| ♀ | 45.6 ± 1.7 n = 9 | 45.3 ± 2 n = 9 | 0.9016 |
| Lean Mass-Change (lb) | 0.1 ± 0.3 n = 20 | 0.6 ± 0.3 n = 20 | 0.3046 |
| ♂ | 0.1 ± 0.5 n = 11 | 1.1 ± 0.4 n = 11 | 0.1257 |
| ♀ | 0 ± 0.5 n = 9 | −0.1 ± 0.5 n = 9 | 0.9303 |
| Total Mass-Initial (lb) | 55.3 ± 1.7 n = 20 | 56.5 ± 1.6 n = 20 | 0.6209 |
| ♂ | 59.8 ± 2.2 n = 11 | 61.4 ± 1.2 n = 11 | 0.5518 |
| ♀ | 49.8 ± 1.1 n = 9 | 50.5 ± 1.6 n = 9 | 0.723 |
| Total Mass-Final (lb) | 58.8 ± 1.7 n = 20 | 61.3 ± 1.8 n = 20 | 0.3281 |
| ♂ | 62.3 ± 2.6 n = 11 | 65.3 ± 1.6 n = 11 | 0.3304 |
| ♀ | 54.5 ± 1.4 n = 9 | 56.4 ± 2.8 n = 9 | 0.5651 |

TABLE 20-continued

Body composition change for L-carnitine and control dogs from beginning to completion of study.

Body Composition

|  | L-carnitine | Control | P-Value |
|---|---|---|---|
| Total Mass-Change (lb) | 3.4 ± 0.8 n = 20 | 4.8 ± 0.9 n = 20 | 0.2641 |
| ♂ | 2.4 ± 0.6 n = 11 | 3.9 ± 1 n = 11 | 0.2051 |
| ♀ | 4.7 ± 1.5 n = 9 | 5.8 ± 1.7 n = 9 | 0.6033 |
| BMC-Initial (g) | 784 ± 44 n = 20 | 842 ± 29 n = 20 | 0.2778 |
| ♂ | 802 ± 80 n = 11 | 928 ± 25 n = 11 | 0.1458 |
| ♀ | 762 ± 18 n = 9 | 737 ± 33 n = 9 | 0.5021 |
| BMC-Final (g) | 866 ± 26 n = 20 | 902 ± 31 n = 20 | 0.3726 |
| ♂ | 903 ± 42 n = 11 | 976 ± 30 n = 11 | 0.1756 |
| ♀ | 820 ± 19 n = 9 | 811 ± 41 n = 9 | 0.8496 |
| BMC-Change (g) | 82 ± 46 n = 20 | 60 ± 8 n = 20 | 0.6413 |
| ♂ | 101 ± 84 n = 11 | 48 ± 8 n = 11 | 0.5341 |
| ♀ | 58 ± 11 n = 9 | 74 ± 13 n = 9 | 0.3526 |

Unpaired t-test. Data displayed indicates mean ± SEM. Differing letters indicates significant difference (P < 0.05).

The L-carnitine dogs responded quickly to the increased feeding of L-carnitine. The L-carnitine dogs generated more activity units (movements/mile/lb BW) measured by Actical monitors for short runs and long runs within a week of feeding the additional L-carnitine. The L-carnitine dogs (male and female) generated more activity throughout the entire 13 wk study for both short and long runs compared to the control dogs. The L-carnitine dogs (male and female) ran the final 15 mile long run 6.56 minutes faster than the control dogs. The L-carnitine male dogs ran the 15 mile run 8.69 minutes faster than control males and faster than either female treatment showing that the additional lean mass of the male may be an advantage in an intense all out race if both sexes are conditioned for the run.

The female L-carnitine dogs generated the most activity for both sexes and treatments throughout the study and also gained the least amount of % fat for body composition during the 90 day study. The lower amount of fat gain in the body of the L-carnitine female would indicate that these dogs were utilizing more fat as fuel during the study to help support their high intense running for short and long runs. The blood biomarkers also supports the fact that females generate more activity/mile/lb BW than males and as a consequence generate more muscle damage as shown by the increase in myoglobin, CK and TBARS.

The biomarkers indicated muscle damage for both sexes caused by the final run but the female showed the largest increase for myoglobin, TBARS, and CK compared to the male. Female L-carnitine dogs showed less muscle damage based on lower increases in myoglobin and TBARS compared to the control female dogs. CK values were also numerically increased compared to pre-run values for all dogs (male and female) during the final long run however the L-carnitine male dogs showed more protection against muscle damage compared to the control male dogs or female dogs.

There was not an overall significant effect of food consumption for the L-carnitine and control dogs but the data shows that L-carnitine dogs consumed less food especially during the first 4 wks of the study and again during the last 4 wks of the study. The L-carnitine may have provided easier access to body fuels for the intense exercise involved in the short and long run which may have affected their overall need to consume dietary energy. The dogs were fed an adjusting positive plane of energy to provide nutrients to maintain their weight and also to help support the extra activity involved in the short and long runs. The reduction in food intake by both treatments as the study progressed may have been due to dogs becoming more conditioned to the work and because seasonal temperatures were increasing.

EXAMPLE 2

A three part crossover study was conducted to show that L-carnitine can help regulate protein turnover and lean mass during intense exercise in performance mammals, namely dogs.

During this study, the dogs that were fed L-carnitine in Example 1 served as the control dogs; they were fed a low L-carnitine basal diet without L-carnitine. The dogs that served as the control dogs in Example 1 became the L-carnitine dogs in this study. When compared statistically, the L-carnitine treatments in Examples 1 and 2 were not significantly different.

Part One: For part one of the study, fifty-six Labrador Retrievers were divided into two equal groups of 28 (14 males, 14 females) based on gender, BW, genetics, age, excitement level, frame size, and lean body mass. The dogs were out of a minimum of 10 different bitches and at least as many sires. Prior to the start of the study, the dogs were tested for lean mass, muscle damage, and antioxidant status as described in Example 1.

The performance dogs were weighed at the beginning of the study and at one week intervals until the end of part one. Feed consumption and refusals were determined daily by weighing and recording the amount offered or refused. The quantity of food provided to each dog on a daily basis was adjusted based on the goal of maintaining the dog's minimum body weight throughout the study.

The performance dogs were fed a low L-carnitine basal diet for 13 days prior to the start of the study and then for the entire 14 week feeding period of part one of the study. The low L-carnitine basal diet, as shown in Table 1, was provided by Lonza Inc.

In addition to the low carnitine basal diet, twenty-eight of the Labs received 250 mg/day of L-carnitine (batch D23013) and 3.75 g/d of sugar, while twenty-eight of the Labs received 4 g/d of sugar.

Both the L-carnitine and control performance dogs were put through a weekly running program consisting of two evenly distributed endurance runs. Groups ranging between 6 and 10 dogs were run together, including both treatments in each group. The endurance runs increased incrementally by 0.5 miles per week (5 miles/session increasing to 10 miles per session over an 11 week period). The dogs were allowed a 1 day rest between runs and a 3 day rest before a scheduled exercise distance increase. The dogs were put through maintenance runs of 5 miles twice in the 12th week and then 2 miles twice in the 13th week. All dogs had at least 4 days of rest prior to the final 15 miles run in the 14th week.

The first exercise session during the week consisted only of endurance style running, while the second session included short 100 m sprints at each mile interval in order to incorporate measurable anaerobic exercise into the weekly regimen. The endurance runs were slightly slower to enhance fat oxidation and represent an exercise intensity equivalent to 50%-65% $VO_2$ max.

Each performance dog wore the Actical activity monitor and GPS tracking collar during the last 15 mile endurance run. The final run was conducted in a manner analogous to that of Example 1. All activity was accurately and precisely calculated using the GPS tracking monitors. Immediately following the 15 mile endurance run, each dog was placed in a kennel and evaluated for recovery time in body temperature (every 15 minutes for 2 hours) and heart rate (every 2 minutes for up to 20 minutes until basal beats per minute (BPM) was reached). Body temperature and heart rate were measured as described in Example 1.

Twenty-four hours after test dogs ran the last 15 mile endurance run, serum samples were taken to evaluate biomarkers for muscle damage and antioxidant status. Blood samples were taken 1) just prior to the beginning of the study; 2) 1 day prior to running the final 15 mile run on the 14th week; 3) 1 hour immediately following the 15 mile run; and 4) 24 hours following the final 15 mile run. After a blood sample was drawn, it was allowed to clot for 30 minutes at 25° C. before being centrifuged for 15 minutes at 2000 g at 4° C. Serum was aliquoted into 0.65 mL microcentrifuge tubes and stored at −80° C. until being assayed at the end of the study for creatine kinase, canine myoglobin, thiobarbituric acid reactive substances (TBARS), and total antioxidant capacity (TAC) using the commercially available kits described in Example 1.

Each dog was also scanned for body composition as described in Example 1 just prior to the beginning of the study and twenty-four hours following the final endurance run.

As shown in Table 21, the time required for the performance dogs to complete the 15 mile final endurance run was almost significant between treatment groups (74.90 min for L-carnitine dogs vs. 72.23 min for control dogs, p=0.060). In terms of gender, the run times between treatment groups were not significant.

TABLE 21

Final 15 Mile Run Time for Test Dogs Completed at
the End of the 14 Week Study
Final Run Time

|  | L-carnitine |  | Control |  | P-Value |
| --- | --- | --- | --- | --- | --- |
| Final Run Time (min) | 74.9 ± 0.94 | n = 28 | 72.23 ± 1.03 | n = 28 | 0.060 |
| Female | 73.7 ± 0.86 | n = 14 | 72.16 ± 1 | n = 14 | 0.253 |
| Male | 76.11 ± 1.64 | n = 14 | 72.31 ± 1.95 | n = 14 | 0.149 |

Unpaired t-test. Data Displayed indicates mean ± SEM. Differing letters indicates significant difference (P < 0.05).

Overall, the heart rate and body temperature recovery following the final long run were not different between treatment groups (Table 22). Immediately following the long run, the L-carnitine dogs had a numerically higher 184.23 average beats per minute (BPM) in comparison to the 178.93 BPM for the control dogs (p=0.246). At 4 minutes into post final run recovery, the heart rates were almost significantly different between treatment groups, with the L-carnitine dogs at an average of 156.15 BPM and the control dogs at an average of 145.2 BPM (p=0.063). However, at the 4 minute post-run interval, the L-carnitine males did have a significantly higher heart rate (160 BPM) compared to that of the control males (138.18 BPM) (p=0.014). After 6 minutes post-recovery, this difference in heart rate was gone. There was no significant difference in heart rates between the L-carnitine and control females.

Both groups showed a continuing decrease in heart rate during the post-run interval and required up to 20 minutes of recovery. The numerically higher heart rate for the L-carnitine dogs immediately following the final run implies that they worked harder during the 15 mile run.

TABLE 22

Heart Rate Recovery at Timed Intervals for Test Dogs
Following the 15 Mile Run
Heartrate After Run

|  | L-carnitine | n = | Control | n = | P-Value |
| --- | --- | --- | --- | --- | --- |
| Whole Groups |  |  |  |  |  |
| Time - 0 min | 184.23 ± 2.49 | 26 | 178.93 ± 3.69 | 28 | 0.246 |
| Time - 2 min | 168.85 ± 3.48 | 26 | 165 ± 3.93 | 26 | 0.467 |
| Time - 4 min | 156.15 ± 4.15 | 26 | 145.2 ± 3.96 | 25 | 0.063 |
| Time - 6 min | 145.77 ± 4.12 | 26 | 140.74 ± 4.98 | 27 | 0.442 |
| Time - 8 min | 131.92 ± 4.04 | 26 | 135 ± 4.88 | 26 | 0.629 |
| Time - 10 min | 120.79 ± 3.72 | 24 | 121.11 ± 4.87 | 27 | 0.959 |
| Time - 12 min | 110.74 ± 4.46 | 27 | 111.85 ± 4.24 | 27 | 0.857 |
| Time - 14 min | 100.4 ± 4.38 | 25 | 99.26 ± 4.65 | 27 | 0.860 |
| Time - 16 min | 85.36 ± 3.43 | 28 | 91.56 ± 3.82 | 27 | 0.232 |
| Time - 18 min | 83.57 ± 3.1 | 28 | 90.81 ± 3.76 | 27 | 0.141 |
| Time - 20 min | 83.21 ± 3.05 | 28 | 87.77 ± 3.28 | 26 | 0.313 |
| Females |  |  |  |  |  |
| Time - 0 min | 180.83 ± 3.36 | 12 | 175.33 ± 5.76 | 14 | 0.438 |
| Time - 2 min | 165 ± 6.09 | 12 | 162.86 ± 5.88 | 13 | 0.802 |
| Time - 4 min | 152.31 ± 6.71 | 13 | 150.71 ± 4.38 | 13 | 0.844 |
| Time - 6 min | 149.17 ± 6.21 | 12 | 147.86 ± 5.76 | 13 | 0.878 |
| Time - 8 min | 135 ± 6.34 | 12 | 145 ± 4.89 | 13 | 0.220 |
| Time - 10 min | 117.9 ± 7.45 | 10 | 132.14 ± 5.36 | 13 | 0.126 |
| Time - 12 min | 113.08 ± 8.5 | 13 | 118.57 ± 6.36 | 13 | 0.610 |
| Time - 14 min | 107.27 ± 8.95 | 11 | 102.86 ± 7.87 | 13 | 0.714 |
| Time - 16 min | 78.57 ± 5.73 | 14 | 90.14 ± 6.34 | 13 | 0.187 |
| Time - 18 min | 77.86 ± 5.47 | 14 | 90.14 ± 6.34 | 13 | 0.153 |
| Time - 20 min | 77.14 ± 5.29 | 14 | 84 ± 5.1 | 12 | 0.364 |
| Males |  |  |  |  |  |
| Time - 0 min | 187.14 ± 3.54 | 14 | 183.08 ± 4.29 | 14 | 0.472 |
| Time - 2 min | 172.14 ± 3.81 | 14 | 167.5 ± 5.24 | 13 | 0.475 |
| Time - 4 min | 160 ± 4.94 | 13 | 138.18 ± 6.72 | 12 | 0.014 |
| Time - 6 min | 142.86 ± 5.59 | 14 | 133.08 ± 7.96 | 14 | 0.324 |
| Time - 8 min | 129.29 ± 5.29 | 14 | 123.33 ± 7.82 | 13 | 0.529 |
| Time - 10 min | 122.86 ± 3.7 | 14 | 109.23 ± 7.11 | 14 | 0.101 |
| Time - 12 min | 108.57 ± 3.76 | 14 | 104.62 ± 5.01 | 14 | 0.533 |
| Time - 14 min | 95 ± 3.1 | 14 | 95.38 ± 4.75 | 14 | 0.946 |
| Time - 16 min | 92.14 ± 3 | 14 | 93.08 ± 4.29 | 14 | 0.860 |
| Time - 18 min | 89.29 ± 2.21 | 14 | 91.54 ± 4.06 | 14 | 0.630 |
| Time - 20 min | 89.29 ± 2.21 | 14 | 91.54 ± 4.06 | 14 | 0.630 |

Unpaired t-test. Data Displayed indicates mean ± SEM. Differing letters indicates significant difference (P < 0.05).

Figure 4A:
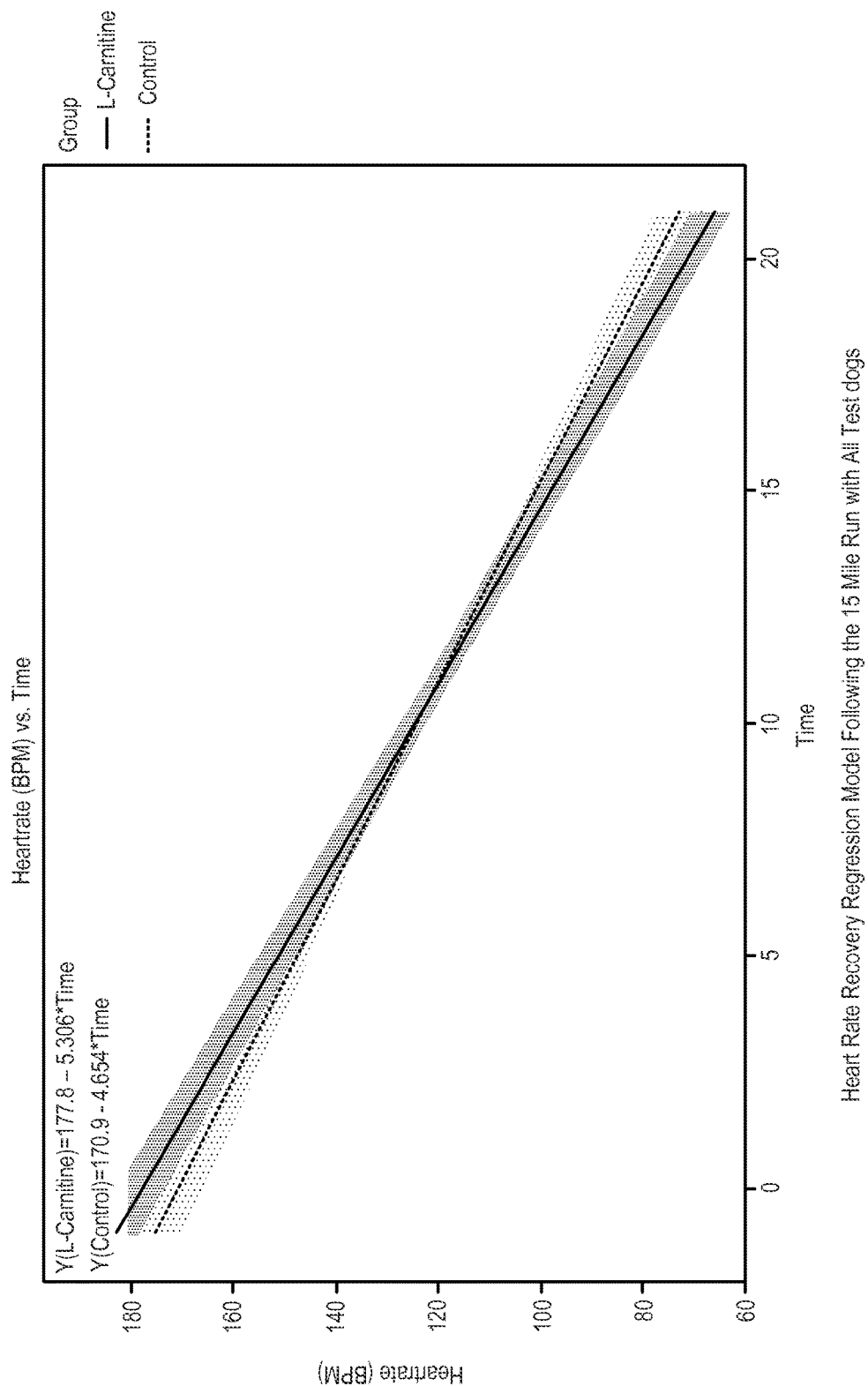
Figure 4B:
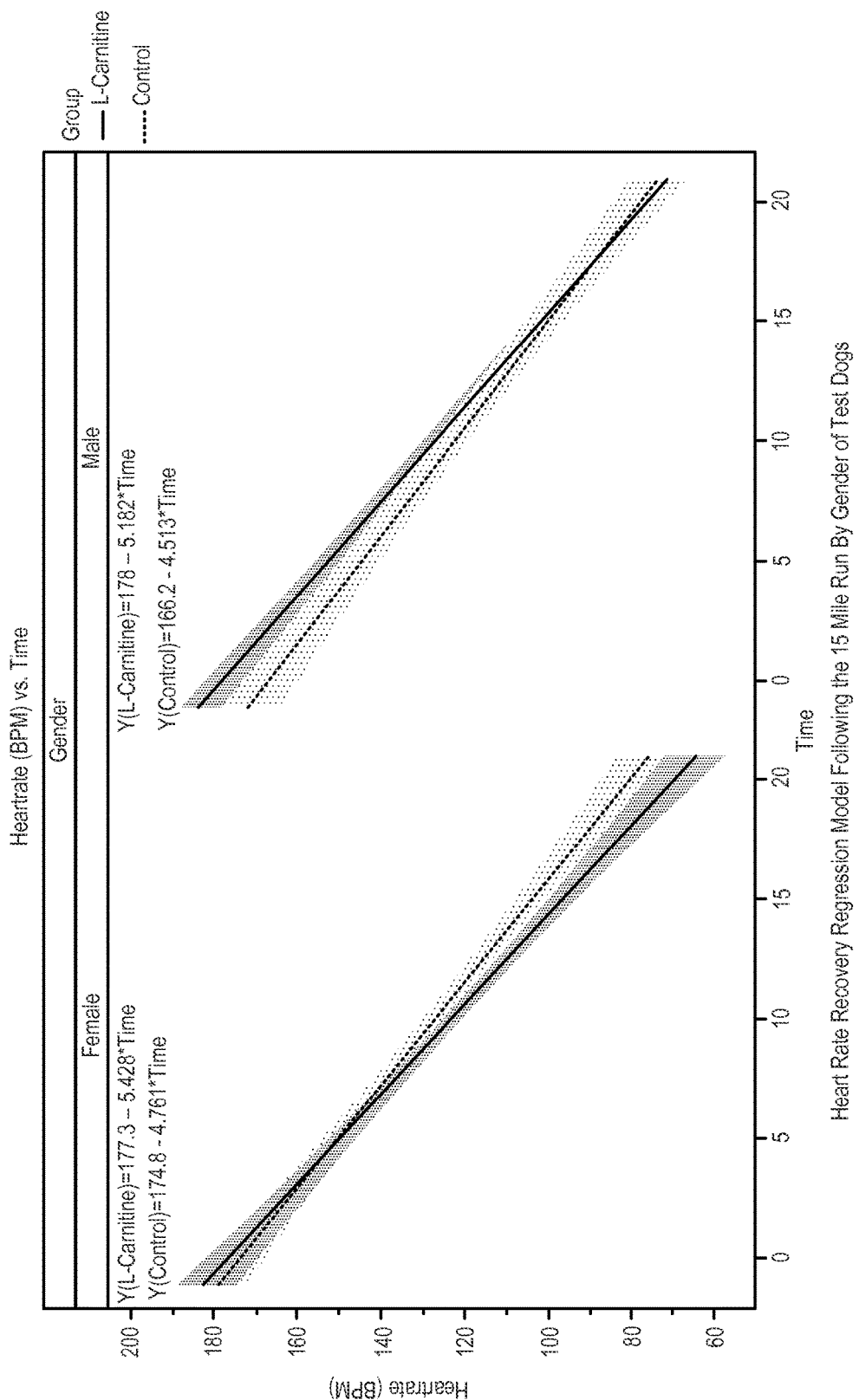

FIGS. 4A and 4B reveal that based on the regression model the overall L-carnitine group and the L-carnitine males and females reached basal heart rate faster than did the control dogs.

There was no significant variance in body temperature by treatment or gender at any time interval following the 15 mile long run (Table 23).

TABLE 23

Body Temperature Recovery for Test Dogs Following the 15 Mile Run
Temperature After Run

|  | L-carnitine | n = | Control | n = | P-Value |
| --- | --- | --- | --- | --- | --- |
| Whole Groups |  |  |  |  |  |
| Temp - 0 min | 105.48 ± 0.25 | 28 | 105.2 ± 0.29 | 28 | 0.482 |
| Temp - 15 min | 102.54 ± 0.23 | 28 | 102.46 ± 0.21 | 28 | 0.793 |
| Temp - 30 min | 101.12 ± 0.15 | 28 | 101.29 ± 0.16 | 28 | 0.456 |
| Temp - 45 min | 101.01 ± 0.14 | 28 | 101.18 ± 0.16 | 28 | 0.442 |
| Temp - 60 min | 101.01 ± 0.14 | 28 | 101.14 ± 0.16 | 28 | 0.543 |
| Females |  |  |  |  |  |
| Temp - 0 min | 105.16 ± 0.35 | 14 | 105.37 ± 0.44 | 14 | 0.712 |
| Temp - 15 min | 102.69 ± 0.24 | 14 | 102.87 ± 0.3 | 14 | 0.639 |
| Temp - 30 min | 101.31 ± 0.2 | 14 | 101.49 ± 0.2 | 14 | 0.517 |
| Temp - 45 min | 101.16 ± 0.2 | 14 | 101.32 ± 0.22 | 14 | 0.594 |
| Temp - 60 min | 101.14 ± 0.2 | 14 | 101.24 ± 0.22 | 14 | 0.749 |

TABLE 23-continued

Body Temperature Recovery for Test Dogs Following the 15 Mile Run
Temperature After Run

| | L-carnitine | n = | Control | n = | P-Value |
|---|---|---|---|---|---|
| Males | | | | | |
| Temp - 0 min | 105.79 ± 0.36 | 14 | 105.02 ± 0.37 | 14 | 0.144 |
| Temp - 15 min | 102.39 ± 0.4 | 14 | 101.98 ± 0.24 | 14 | 0.391 |
| Temp - 30 min | 100.94 ± 0.23 | 14 | 101.05 ± 0.23 | 14 | 0.739 |
| Temp - 45 min | 100.87 ± 0.19 | 14 | 101.02 ± 0.23 | 14 | 0.633 |
| Temp - 60 min | 100.87 ± 0.19 | 14 | 101.02 ± 0.23 | 14 | 0.633 |

Unpaired t-test. Data displayed indicates mean ± SEM. Differing letters indicates significant difference ($P < 0.05$).

Figure 5A:
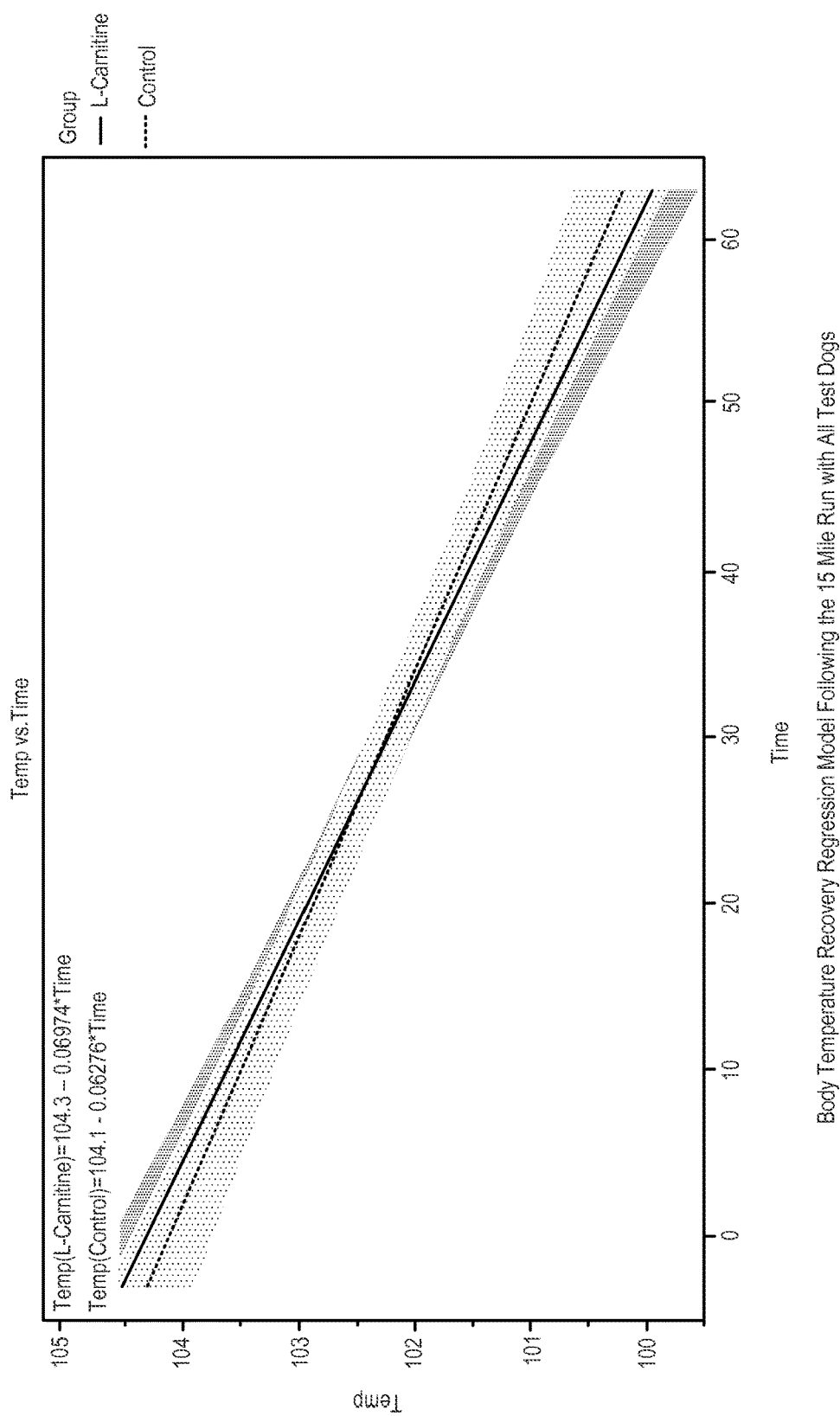
Figure 5B:
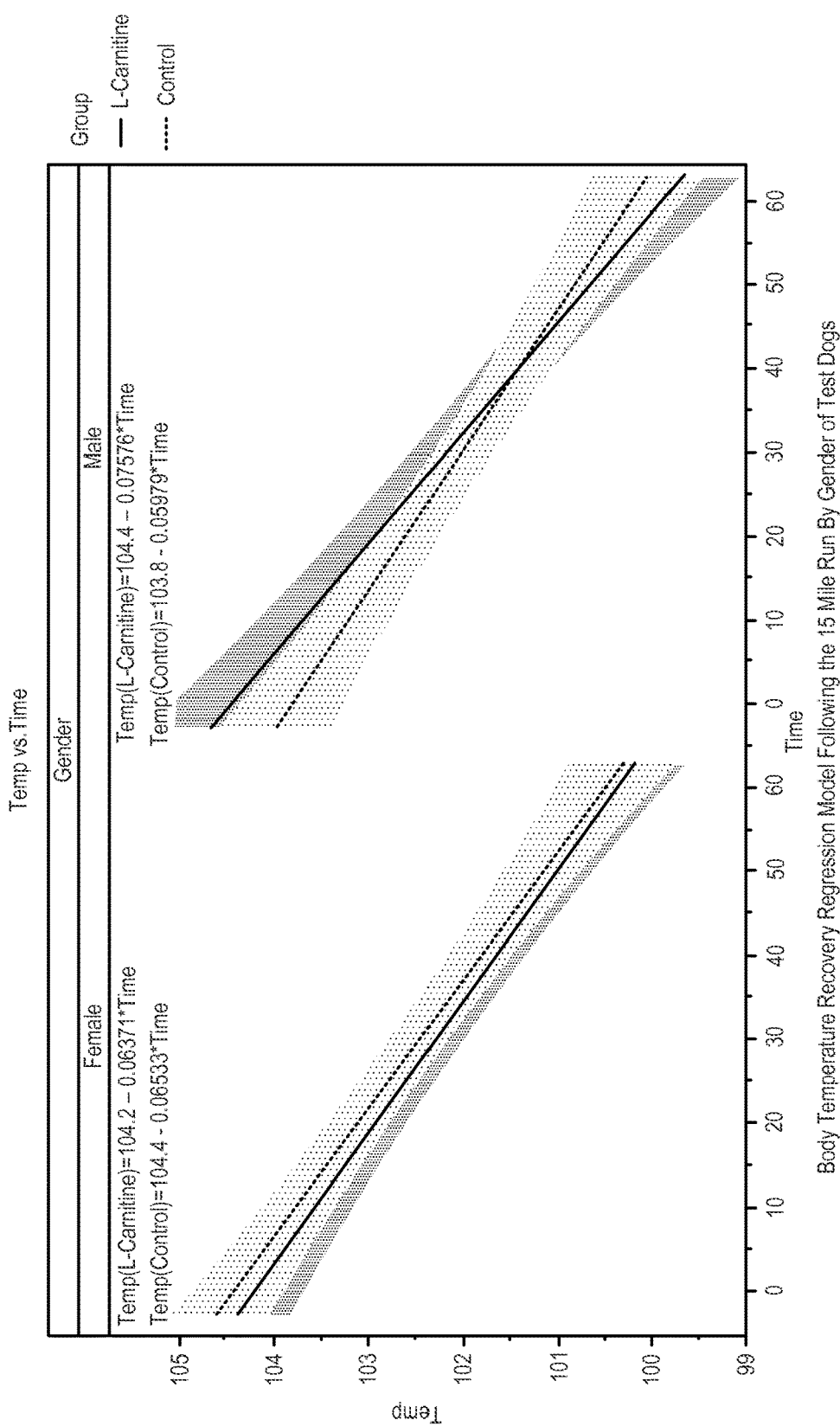

The regression model reveals that the L-carnitine male and female dogs reached basal temperatures faster than the control dogs did (FIGS. 5A and 5B).

Figure 6:
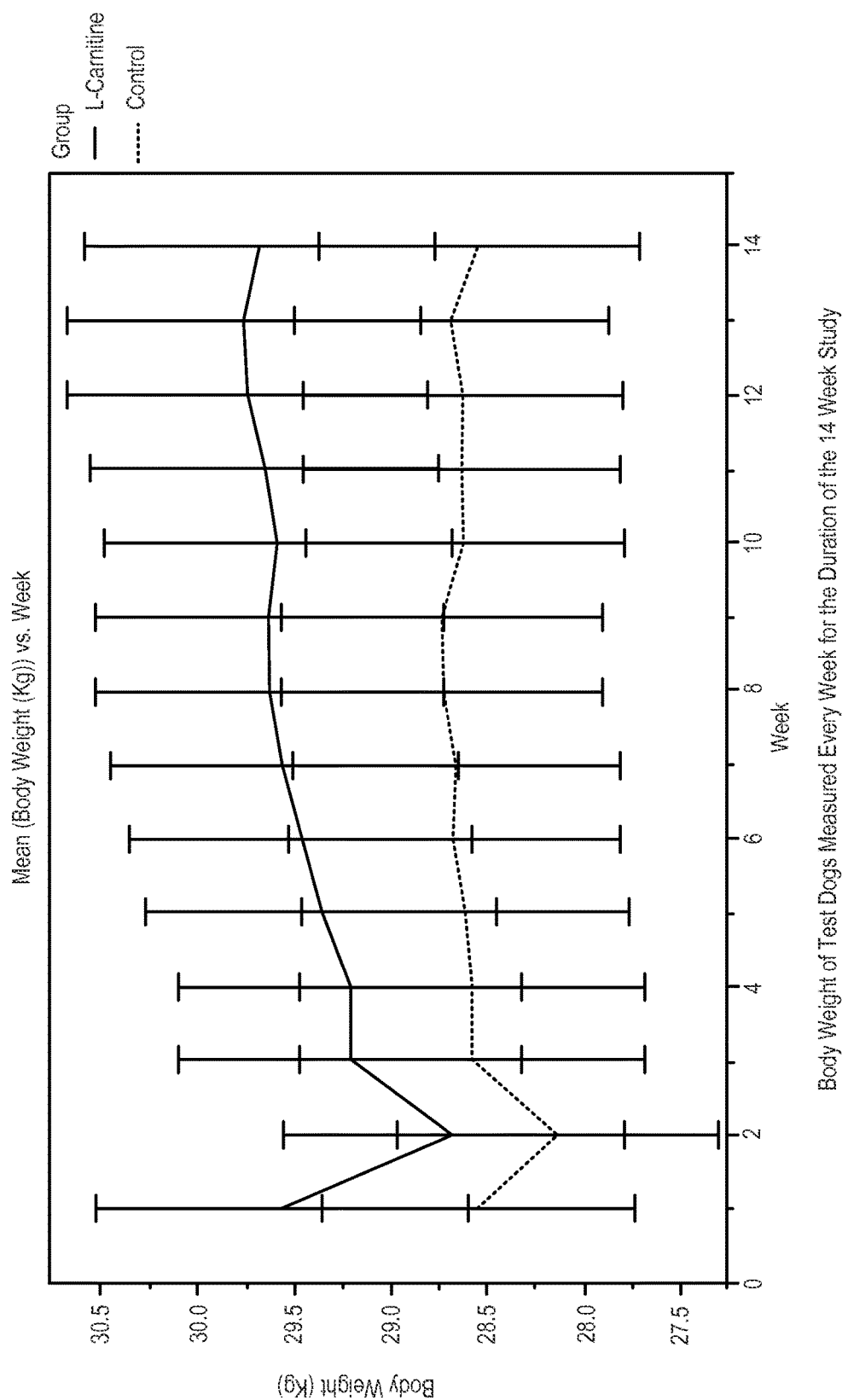

There was also no significant variation in body weight by treatment or gender at any point during the 14 week study (Table 24 and FIG. 6).

TABLE 24

Weekly Body Weight, by Time * Treatment and by Time *
Treatment * Gender (kg) for Test Dogs During the 14 Week Study

| | L-carnitine | n = | Control | n = | P-Value |
|---|---|---|---|---|---|
| Weekly Body Weight (kg) | | | | | |
| Week 1 | 29.57 ± 0.96 | 28 | 28.56 ± 0.81 | 28 | 0.424 |
| Week 2 | 28.68 ± 0.88 | 28 | 28.14 ± 0.84 | 28 | 0.658 |
| Week 3 | 29.21 ± 0.89 | 28 | 28.59 ± 0.89 | 28 | 0.623 |
| Week 4 | 29.21 ± 0.89 | 28 | 28.59 ± 0.89 | 28 | 0.623 |
| Week 5 | 29.36 ± 0.9 | 28 | 28.62 ± 0.85 | 28 | 0.551 |
| Week 6 | 29.47 ± 0.89 | 28 | 28.68 ± 0.86 | 28 | 0.527 |
| Week 7 | 29.57 ± 0.89 | 28 | 28.66 ± 0.85 | 28 | 0.466 |
| Week 8 | 29.63 ± 0.9 | 28 | 28.74 ± 0.84 | 28 | 0.471 |
| Week 9 | 29.63 ± 0.9 | 28 | 28.74 ± 0.84 | 28 | 0.471 |
| Week 10 | 29.59 ± 0.9 | 28 | 28.62 ± 0.82 | 28 | 0.429 |
| Week 11 | 29.65 ± 0.9 | 28 | 28.63 ± 0.82 | 28 | 0.405 |
| Week 12 | 29.74 ± 0.93 | 28 | 28.62 ± 0.83 | 28 | 0.373 |
| Week 13 | 29.76 ± 0.91 | 28 | 28.69 ± 0.82 | 28 | 0.384 |
| Week 14 | 29.68 ± 0.9 | 28 | 28.54 ± 0.83 | 28 | 0.360 |
| Weekly Body Weight (kg) by Gender | | | | | |
| Week 1 Female | 25.72 ± 0.93 | 14 | 25.86 ± 0.62 | 14 | 0.902 |
| Week 1 Male | 33.41 ± 0.82 | 14 | 31.67 ± 1.07 | 14 | 0.207 |
| Week 2 Female | 25.26 ± 0.88 | 14 | 25.27 ± 0.73 | 14 | 0.993 |
| Week 2 Male | 32.11 ± 0.81 | 14 | 31.45 ± 1 | 14 | 0.617 |
| Week 3 Female | 26.04 ± 0.98 | 14 | 25.87 ± 0.82 | 14 | 0.900 |
| Week 3 Male | 32.39 ± 0.9 | 14 | 31.72 ± 1.19 | 14 | 0.657 |
| Week 4 Female | 26.04 ± 0.98 | 14 | 25.87 ± 0.82 | 14 | 0.900 |
| Week 4 Male | 32.39 ± 0.9 | 14 | 31.72 ± 1.19 | 14 | 0.657 |
| Week 5 Female | 26.03 ± 0.98 | 14 | 25.92 ± 0.76 | 14 | 0.931 |
| Week 5 Male | 32.69 ± 0.86 | 14 | 31.73 ± 1.09 | 14 | 0.493 |
| Week 6 Female | 26.25 ± 1 | 14 | 25.99 ± 0.81 | 14 | 0.844 |
| Week 6 Male | 32.69 ± 0.84 | 14 | 31.78 ± 1.1 | 14 | 0.517 |
| Week 7 Female | 26.27 ± 0.94 | 14 | 25.99 ± 0.78 | 14 | 0.821 |
| Week 7 Male | 32.86 ± 0.87 | 14 | 31.75 ± 1.08 | 14 | 0.428 |
| Week 8 Female | 26.37 ± 1.01 | 14 | 26.12 ± 0.78 | 14 | 0.846 |
| Week 8 Male | 32.89 ± 0.86 | 14 | 31.75 ± 1.09 | 14 | 0.418 |
| Week 9 Female | 26.37 ± 1.01 | 14 | 26.12 ± 0.78 | 14 | 0.846 |
| Week 9 Male | 32.89 ± 0.86 | 14 | 31.75 ± 1.09 | 14 | 0.418 |
| Week 10 Female | 26.28 ± 0.99 | 14 | 26.11 ± 0.78 | 14 | 0.897 |
| Week 10 Male | 32.9 ± 0.83 | 14 | 31.51 ± 1.08 | 14 | 0.316 |
| Week 11 Female | 26.32 ± 0.98 | 14 | 26.11 ± 0.78 | 14 | 0.869 |
| Week 11 Male | 32.99 ± 0.84 | 14 | 31.53 ± 1.07 | 14 | 0.296 |
| Week 12 Female | 26.26 ± 1.02 | 14 | 26.09 ± 0.77 | 14 | 0.895 |
| Week 12 Male | 33.22 ± 0.81 | 14 | 31.55 ± 1.09 | 14 | 0.228 |
| Week 13 Female | 26.31 ± 0.99 | 14 | 26.11 ± 0.76 | 14 | 0.878 |
| Week 13 Male | 33.21 ± 0.8 | 14 | 31.65 ± 1.04 | 14 | 0.244 |
| Week 14 Female | 26.23 ± 0.95 | 14 | 25.91 ± 0.75 | 14 | 0.797 |
| Week 14 Male | 33.13 ± 0.81 | 14 | 31.58 ± 1.09 | 14 | 0.264 |

Unpaired t-test. Data displayed indicates mean ± SEM. Differing letters indicates significant difference ($P < 0.05$).

Table 25 demonstrates that the food offered daily (g/d) numerically decreased for both treatment groups during the course of the study. FIG. 7 shows that the overall mean amount of food offered per day for the L-carnitine group (677 g/d) and the control group (683 g/d) was not considered to be significantly different.

Figure 8:
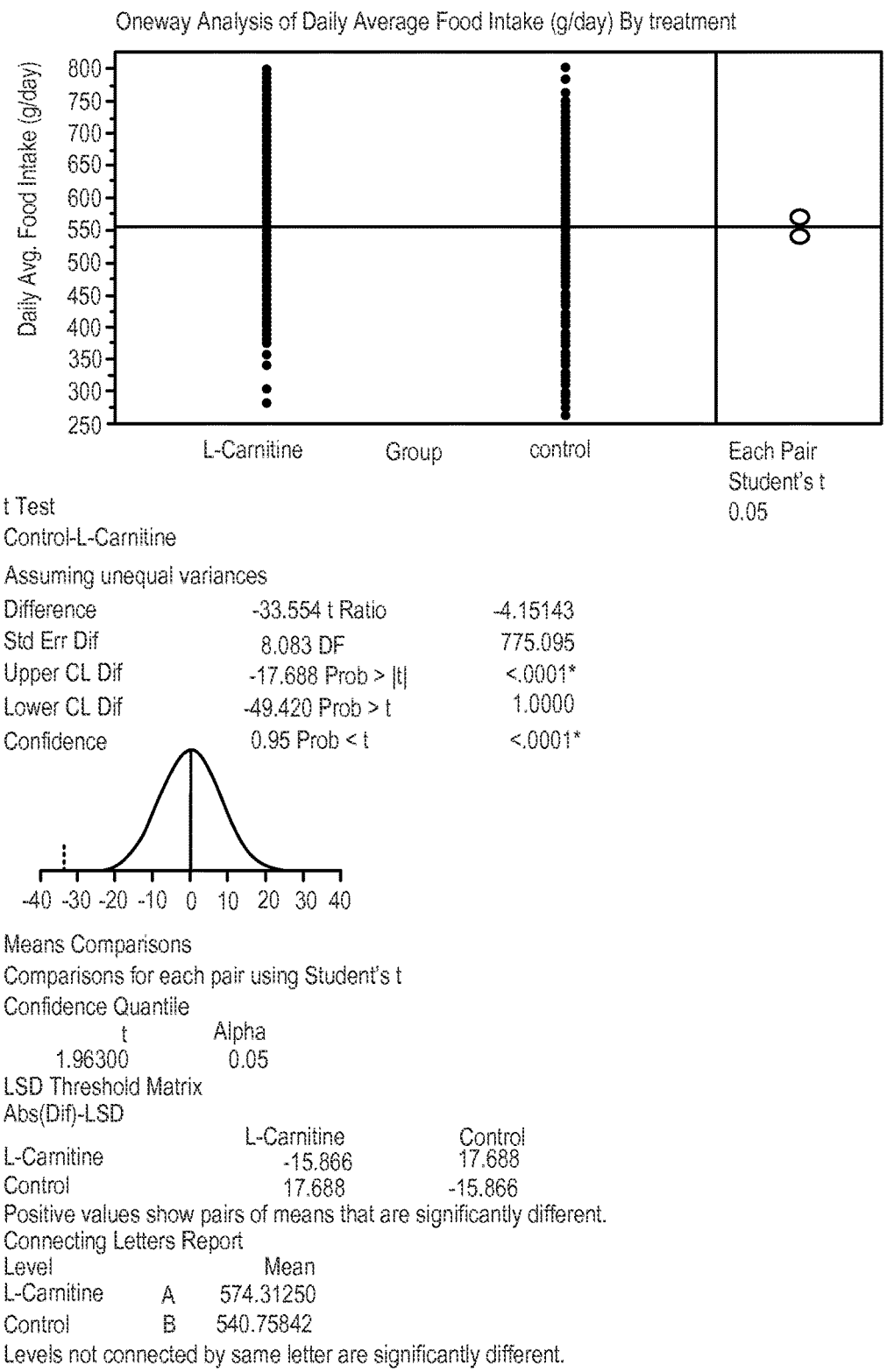

The amount of food consumed was significantly different between treatment groups only in week 1 (L-carnitine 618.25 g/d vs. control 554.32 g/d; p=0.051) and week 4 (L-carnitine 629.43 g/d vs. control 572.93 g/d; p=0.045). During those two weeks, the L-carnitine group's daily food intake was significantly greater than that of the control group (Table 25). Overall, as seen in FIG. 8, the L-carnitine group demonstrated a significantly higher overall mean food intake per day (574 g/d) than did the control dogs (540 g/d) (p<0.0001).

Figure 9:
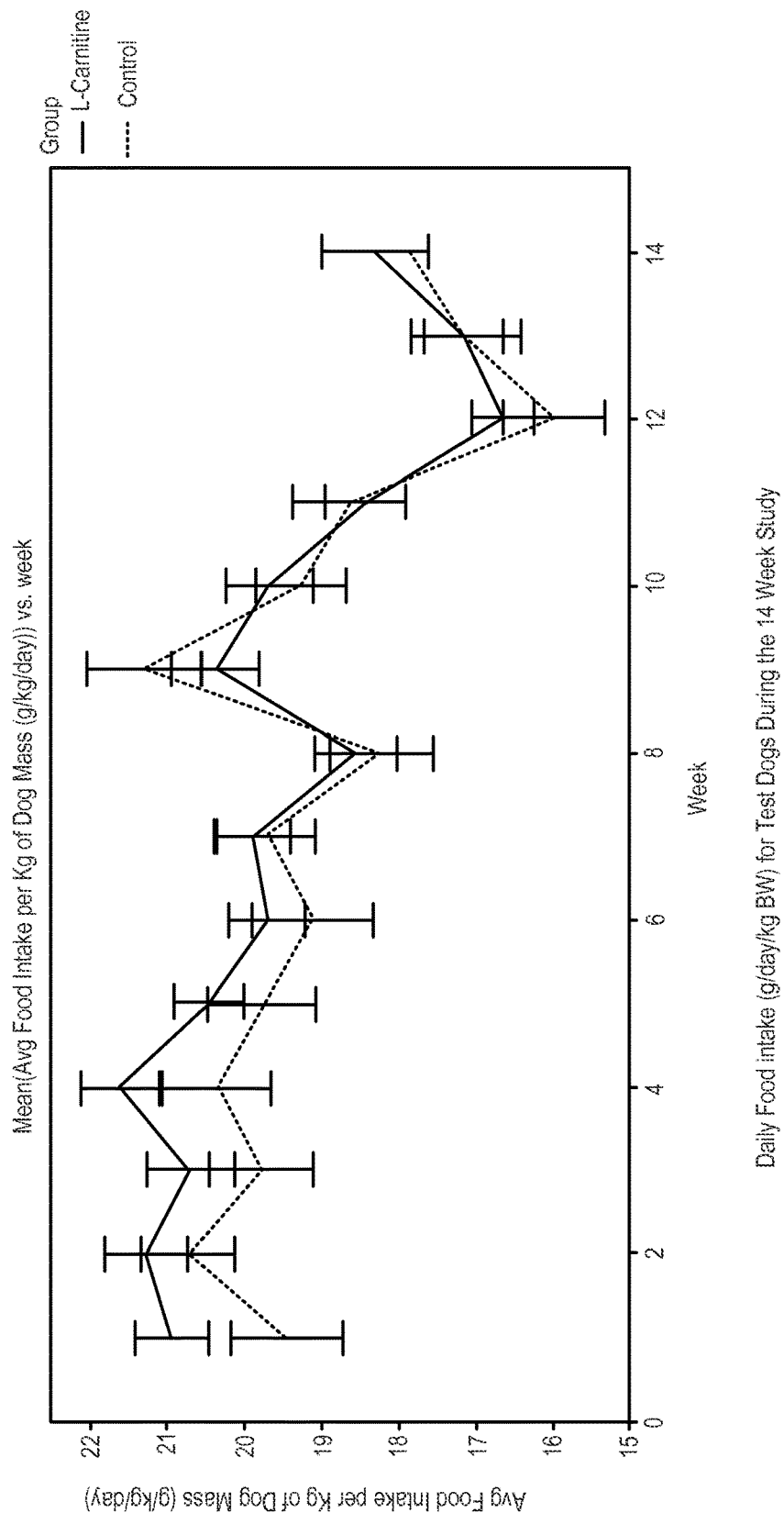

As seen in Table 25 and FIG. 9, the difference in g/d/kg body weight (BW) was close to significance only in week 1 (L-carnitine 20.96 vs. control 19.49 g/d/kg BW; p=0.093). The food consumption numerically decreased per kg BW for both groups as the mileage increased primarily because of improved fitness of dogs and increasing environmental temperatures. The difference between treatment groups in intake of kcals of ME was also close to significance only in week 1 (L-carnitine 83.83 vs. control 77.94 kcal/d/kg BW; p=0.093).

TABLE 25

Food Offered Daily (g/d) & Daily Food Consumption (g/d; g/d/kg
BW; kcal ME/d/kg BW) of All Test Dogs

| | L-carnitine | n = | Control | n = | P-Value |
|---|---|---|---|---|---|
| Average Daily Food Offered (g) | | | | | |
| Week 1 | 700 ± 19.25 | 28 | 692.86 ± 19.2 | 28 | 0.794 |
| Week 2 | 700 ± 19.25 | 28 | 692.86 ± 19.2 | 28 | 0.794 |
| Week 3 | 700 ± 19.25 | 28 | 692.86 ± 19.2 | 28 | 0.794 |
| Week 4 | 700 ± 19.25 | 28 | 692.86 ± 19.2 | 28 | 0.794 |
| Week 5 | 700 ± 19.25 | 28 | 693.89 ± 19.04 | 28 | 0.822 |
| Week 6 | 701.04 ± 19.07 | 28 | 698.96 ± 18.57 | 28 | 0.938 |
| Week 7 | 699.43 ± 19.86 | 28 | 696.89 ± 19.23 | 28 | 0.927 |
| Week 8 | 689.29 ± 23.2 | 28 | 689.29 ± 21.42 | 28 | 1.000 |
| Week 9 | 687.79 ± 23.11 | 28 | 689.29 ± 21.42 | 28 | 0.962 |
| Week 10 | 674.07 ± 23.56 | 28 | 686.79 ± 21.91 | 28 | 0.694 |
| Week 11 | 635.25 ± 26.06 | 28 | 665.79 ± 26.68 | 28 | 0.417 |
| Week 12 | 628.57 ± 25.64 | 28 | 657.14 ± 28.83 | 28 | 0.462 |
| Week 13 | 628.57 ± 25.64 | 28 | 657.14 ± 28.83 | 28 | 0.462 |
| Week 14 | 628.57 ± 25.64 | 28 | 657.14 ± 28.83 | 28 | 0.462 |
| Daily Food Intake (g) | | | | | |
| Week 1 | 618.25 ± 22.33 | 28 | 554.32 ± 22.88 | 28 | 0.051 |
| Week 2 | 608.79 ± 22.8 | 28 | 580 ± 20.08 | 28 | 0.348 |
| Week 3 | 600.54 ± 19.89 | 28 | 557.43 ± 16.75 | 28 | 0.103 |
| Week 4 | 629.43 ± 21.4 | 28 | 572.93 ± 17.25 | 28 | 0.045 |
| Week 5 | 597.07 ± 18.65 | 28 | 558 ± 16.99 | 28 | 0.127 |
| Week 6 | 579.11 ± 21.17 | 28 | 540.14 ± 17.62 | 28 | 0.163 |
| Week 7 | 584.5 ± 18.91 | 28 | 560.14 ± 18.38 | 28 | 0.360 |
| Week 8 | 547.14 ± 20.91 | 28 | 517.46 ± 17.54 | 28 | 0.282 |
| Week 9 | 602.79 ± 23.4 | 28 | 605.25 ± 19.79 | 28 | 0.936 |
| Week 10 | 580.04 ± 21.88 | 28 | 546.93 ± 16.43 | 28 | 0.232 |
| Week 11 | 543.89 ± 19.79 | 28 | 528.25 ± 20.46 | 28 | 0.585 |
| Week 12 | 493.68 ± 19.06 | 28 | 452.07 ± 18.74 | 28 | 0.125 |
| Week 13 | 511.82 ± 22.64 | 28 | 488.11 ± 20.45 | 28 | 0.440 |
| Week 14 | 543.5 ± 26.43 | 28 | 509.82 ± 25.5 | 28 | 0.363 |
| Daily Food Intake (g/d/kg BW) | | | | | |
| Week 1 | 20.96 ± 0.46 | 28 | 19.49 ± 0.73 | 28 | 0.093 |
| Week 2 | 21.3 ± 0.55 | 28 | 20.76 ± 0.61 | 28 | 0.512 |
| Week 3 | 20.72 ± 0.58 | 28 | 19.8 ± 0.68 | 28 | 0.312 |
| Week 4 | 21.64 ± 0.52 | 28 | 20.37 ± 0.72 | 28 | 0.158 |
| Week 5 | 20.47 ± 0.45 | 28 | 19.78 ± 0.69 | 28 | 0.415 |
| Week 6 | 19.72 ± 0.51 | 28 | 19.14 ± 0.73 | 28 | 0.517 |
| Week 7 | 19.91 ± 0.49 | 28 | 19.73 ± 0.62 | 28 | 0.824 |

TABLE 25-continued

Food Offered Daily (g/d) & Daily Food Consumption (g/d; g/d/kg BW; kcal ME/d/kg BW) of All Test Dogs

|  | L-carnitine | n = | Control | n = | P-Value |
|---|---|---|---|---|---|
| Week 8 | 18.55 ± 0.54 | 28 | 18.25 ± 0.67 | 28 | 0.724 |
| Week 9 | 20.39 ± 0.55 | 28 | 21.31 ± 0.73 | 28 | 0.317 |
| Week 10 | 19.69 ± 0.56 | 28 | 19.29 ± 0.58 | 28 | 0.621 |
| Week 11 | 18.45 ± 0.52 | 28 | 18.64 ± 0.74 | 28 | 0.834 |
| Week 12 | 16.66 ± 0.43 | 28 | 15.98 ± 0.67 | 28 | 0.397 |
| Week 13 | 17.18 ± 0.51 | 28 | 17.16 ± 0.7 | 28 | 0.986 |
| Week 14 | 18.3 ± 0.69 | 28 | 17.85 ± 0.74 | 28 | 0.655 |
| Daily Food Intake (kcal ME/d/kg BW) | | | | | |
| Week 1 | 83.83 ± 1.85 | 28 | 77.94 ± 2.9 | 28 | 0.093 |
| Week 2 | 85.21 ± 2.22 | 28 | 83.03 ± 2.44 | 28 | 0.512 |
| Week 3 | 82.87 ± 2.34 | 28 | 79.21 ± 2.71 | 28 | 0.312 |
| Week 4 | 86.54 ± 2.08 | 28 | 81.49 ± 2.87 | 28 | 0.160 |
| Week 5 | 81.86 ± 1.82 | 28 | 79.13 ± 2.77 | 28 | 0.413 |
| Week 6 | 78.87 ± 2.06 | 28 | 76.54 ± 2.93 | 28 | 0.519 |
| Week 7 | 79.61 ± 1.97 | 28 | 78.9 ± 2.49 | 28 | 0.824 |
| Week 8 | 74.21 ± 2.16 | 28 | 72.99 ± 2.67 | 28 | 0.723 |
| Week 9 | 81.55 ± 2.2 | 28 | 85.24 ± 2.92 | 28 | 0.317 |
| Week 10 | 78.76 ± 2.25 | 28 | 77.16 ± 2.32 | 28 | 0.623 |
| Week 11 | 73.79 ± 2.09 | 28 | 74.55 ± 2.96 | 28 | 0.836 |
| Week 12 | 66.64 ± 1.71 | 28 | 63.91 ± 2.69 | 28 | 0.396 |
| Week 13 | 68.71 ± 2.06 | 28 | 68.65 ± 2.79 | 28 | 0.986 |
| Week 14 | 73.21 ± 2.75 | 28 | 71.4 ± 2.95 | 28 | 0.655 |

Unpaired t-test. Data displayed indicates mean ± SEM. Differing letters indicates significant difference (P < 0.05).

The consumption per kg of lean mass was determined by dividing the mean lean mass of each group into its mean daily food consumption value at the initial and then the final body scans. FIGS. 10A, B, and C show that the overall change in consumption per kg of lean mass (LM) between treatment group and gender was significantly different.

Figure 11A:
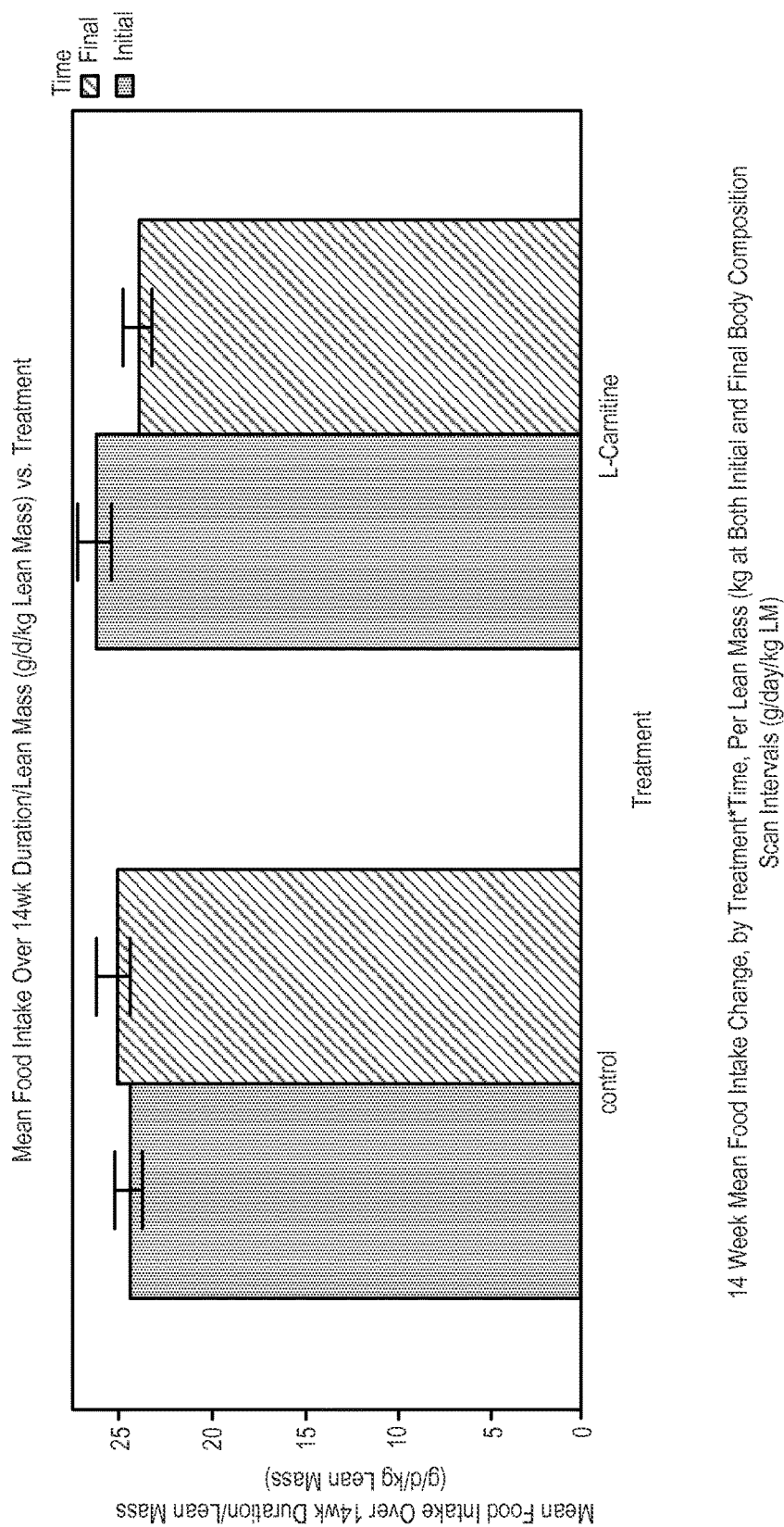

The change in the L-carnitine dogs consumption per kg of LM from the beginning to the end of part one showed a decrease, indicating a reduced need for food per kg of LM as the study progressed; the initial consumption was 26.24 g/d/kg LM, while the final consumption was 24.02 g/d/kg LM (p=0.0734). The control group showed no significant change other than a numerical increase in consumption (25.00 g/d/kg LM to 25.53 g/d/kg LM) (p=0.06569) (Table 26A and FIG. 11A)

TABLE 26A

14 Week Mean Food Intake and Change Within Each Treatment at Both Body Composition Scan Intervals (g/d/kg LM).
14 Week Food Intake Mean g/kg LM - Change Within Treatment Group

| | Initial | | | Final | | | |
|---|---|---|---|---|---|---|---|
| Treatment | Mean | SEM | n = | Mean | SEM | n = | P-Value |
| L-carnitine | 26.24 | 0.896 | 28 | 24.02 | 0.822 | 28 | 0.0734 |
| Control | 25 | 0.824 | 28 | 25.53 | 0.854 | 28 | 0.6569 |

Figure 11B:
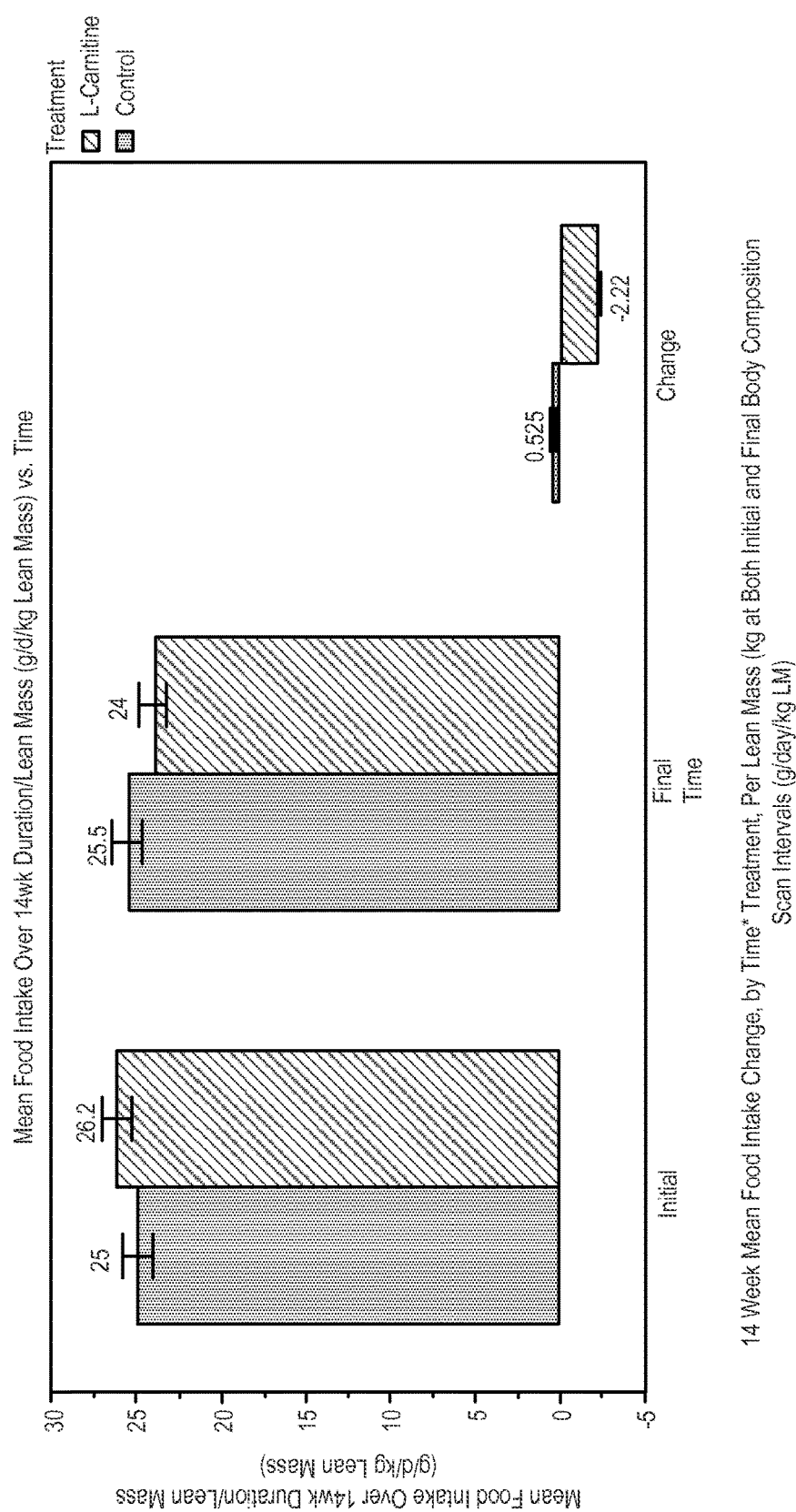

By the end of the 14 week study, the L-carnitine dogs had significantly decreased their food intake per kg LM (−2.22 g/d/kg LM) in comparison to the control dogs (0.53 g/d/kg LM) (p<0.001) (Table 26B and FIG. 11B). Thus, for the L-carnitine dogs, the supplementation of L-carnitine may have provided easier access to body fuels for the intense exercise involved in part one of the study, which could have led to a decrease in their overall need to consume dietary energy.

TABLE 26B

14 Week Mean Food Intake and Change, by Time * Treatment, at Both Body Composition Scan Intervals (g/d/kg LM)

Mean Food Intake Over 14 wks/Lean Mass (g/d/kg LM)

| | L-carnitine | | | Control | | | |
|---|---|---|---|---|---|---|---|
| Time | Mean | SEM | n = | Mean | SEM | n = | P-Value |
| Change | −2.22 | 0.189 | 28 | 0.525 | 0.211 | 28 | <0.0001 |
| Final | 24.02 | 0.822 | 28 | 25.53 | 0.854 | 28 | 0.2077 |
| Initial | 26.24 | 0.896 | 28 | 25.00 | 0.824 | 28 | 0.3146 |

Figure 11C:
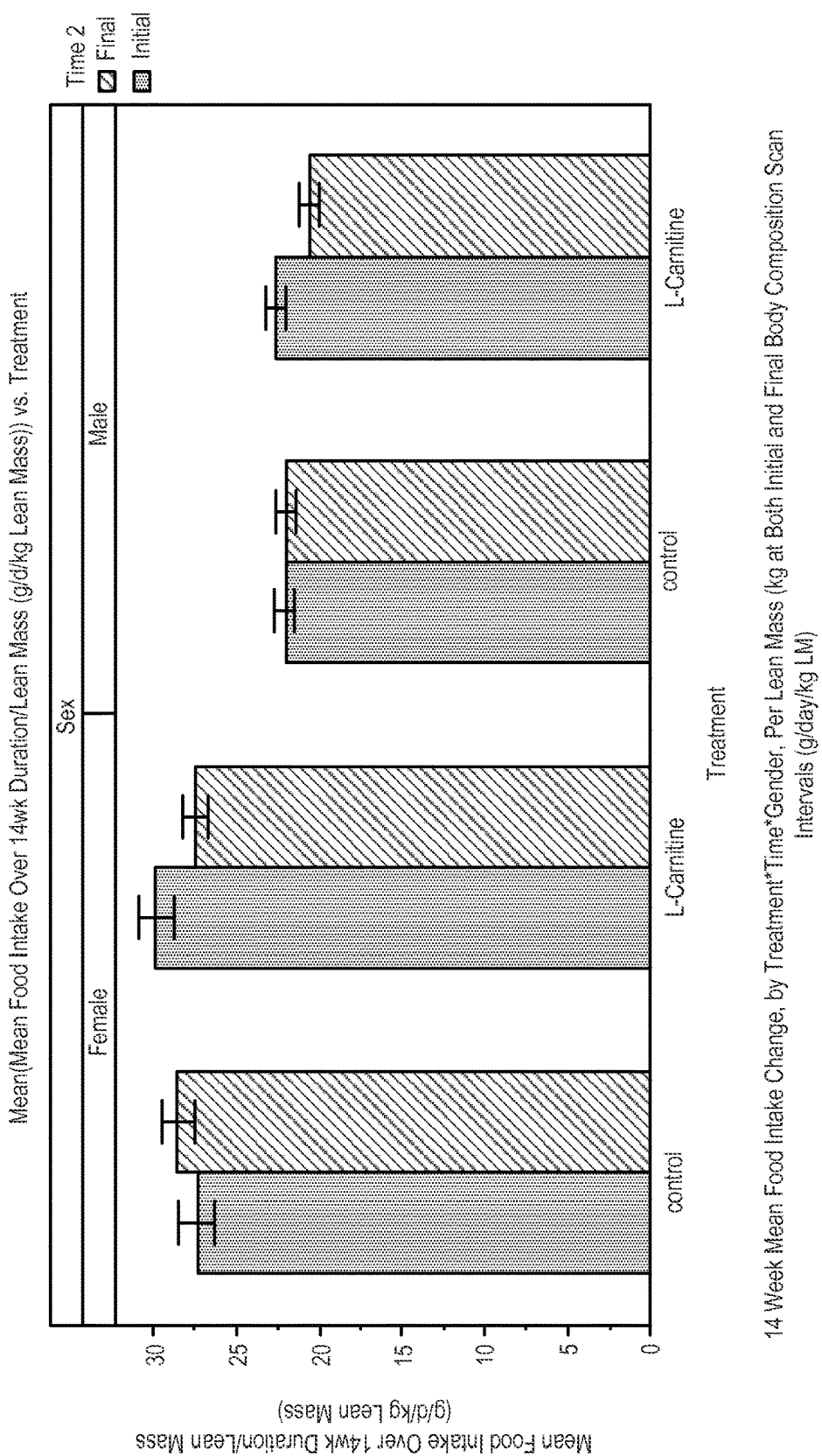
Figure 11D:
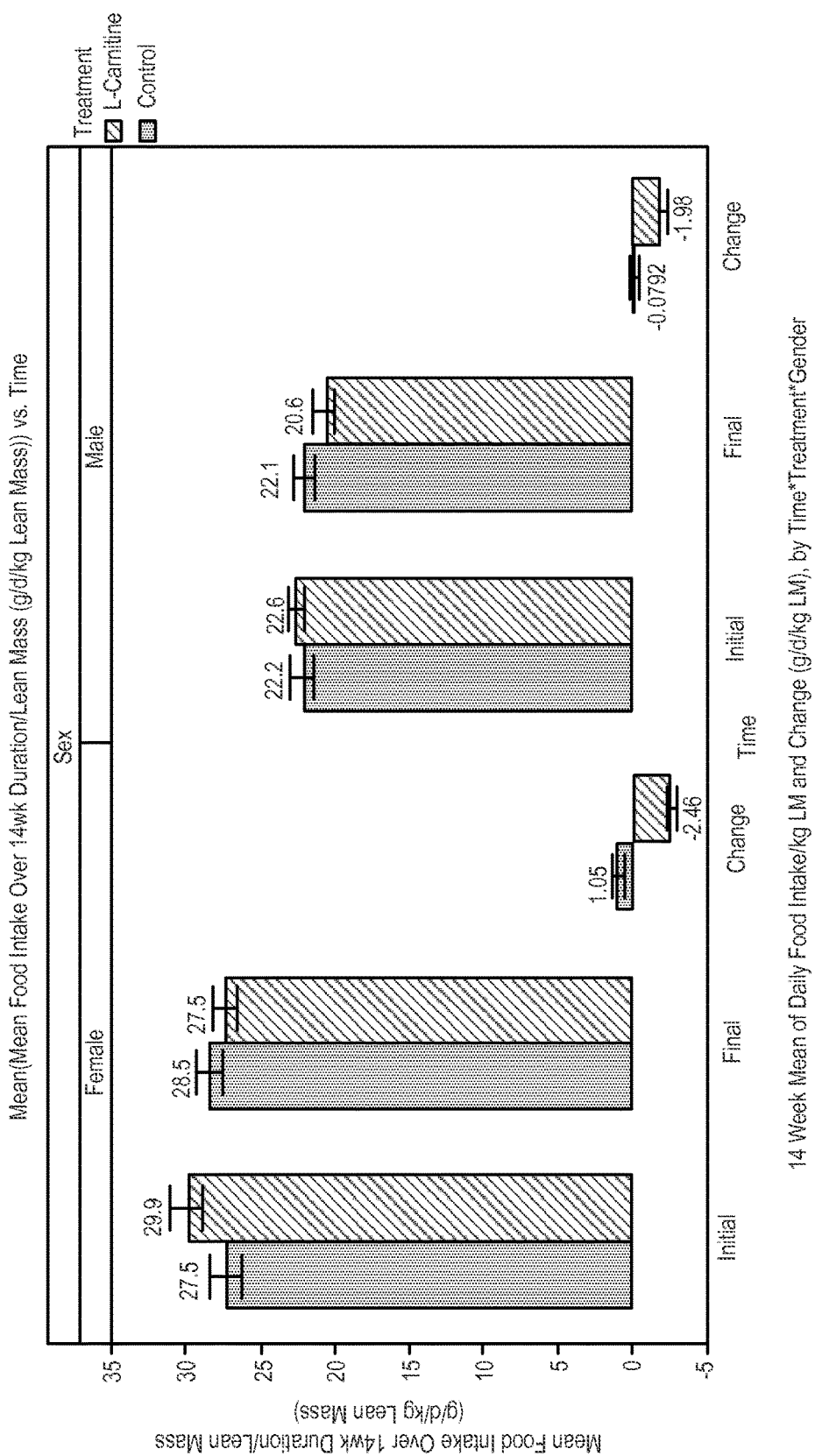

Both females and males in the L-carnitine group showed a significant decrease in food intake per kg LM; in comparison, the control males exhibited a very small numerical decrease while the control females consumed numerically more food per kg of lean mass (Table 26C and FIGS. 11C and D). The female control dogs' increase in food consumption may be due to efforts to replenish their bodies to aid in repair of the cellular injury and protein degradation they were incurring during the intense exercise regimen.

TABLE 26C

14 Week Mean Food Intake/kg LM and Change, by Time * Treatment * Gender, at Both Body Composition Scan Intervals (g/d/kg LM)
Mean Food Intake Over 14 wk Duration/Lean Mass (g/d/kg Lean Mass)

| | L-carnitine | | | Control | | | |
|---|---|---|---|---|---|---|---|
| Time | Mean | SEM | n = | Mean | SEM | n = | P-Value |
| Change, F | −2.46 | 0.339 | 14 | 1.05 | 0.322 | 14 | <0.0001 |
| Change, M | −1.98 | 0.158 | 14 | −0.08 | 0.137 | 14 | <0.0001 |
| Initial, F | 29.92 | 0.991 | 14 | 27.47 | 1.074 | 14 | 0.1057 |
| Initial, M | 22.56 | 0.524 | 14 | 22.16 | 0.696 | 14 | 0.6488 |
| Final, F | 27.46 | 0.812 | 14 | 28.51 | 0.944 | 14 | 0.4028 |
| Final, M | 20.58 | 0.576 | 14 | 22.08 | 0.700 | 14 | 0.1086 |

Figure 14A:
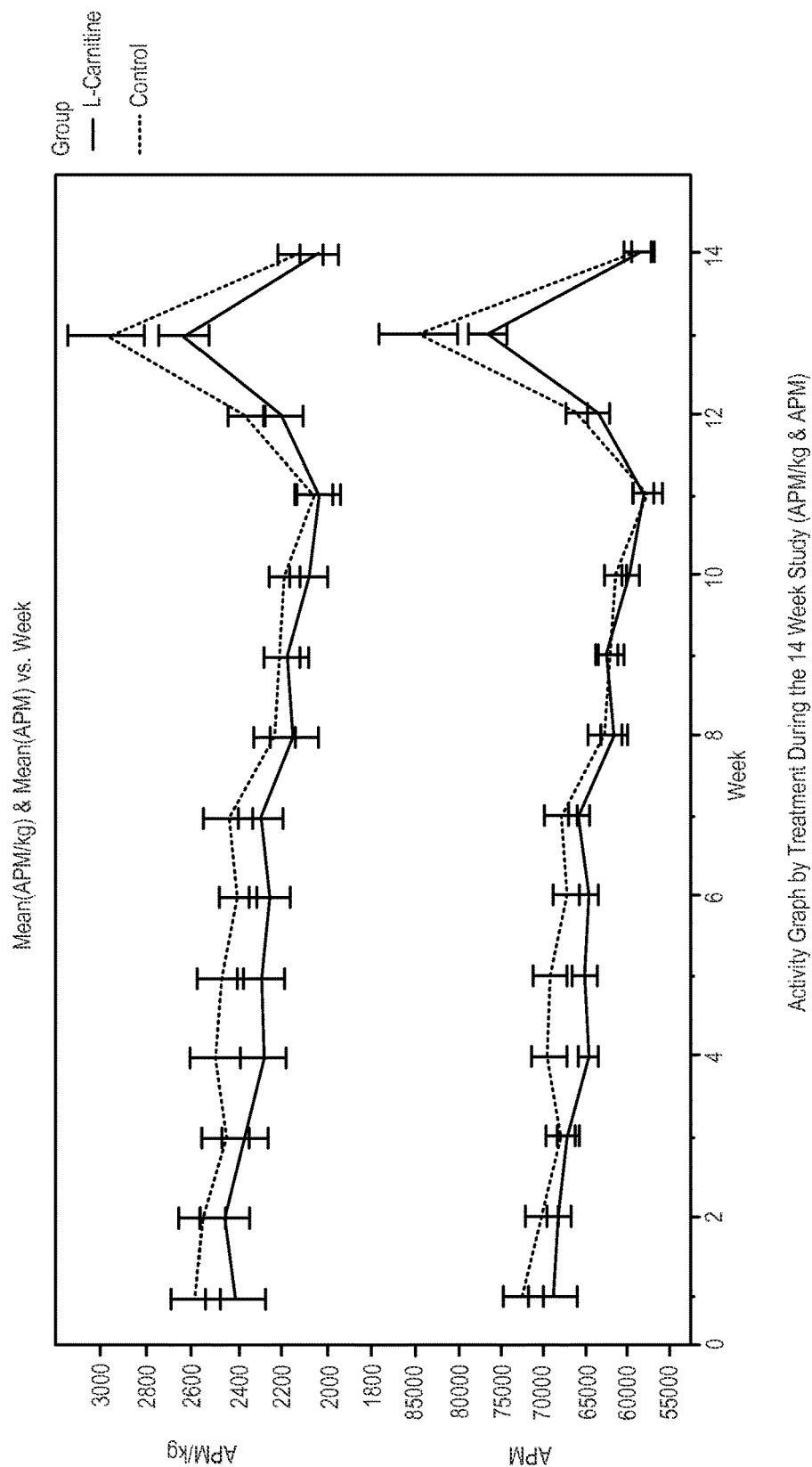
Figure 14B:
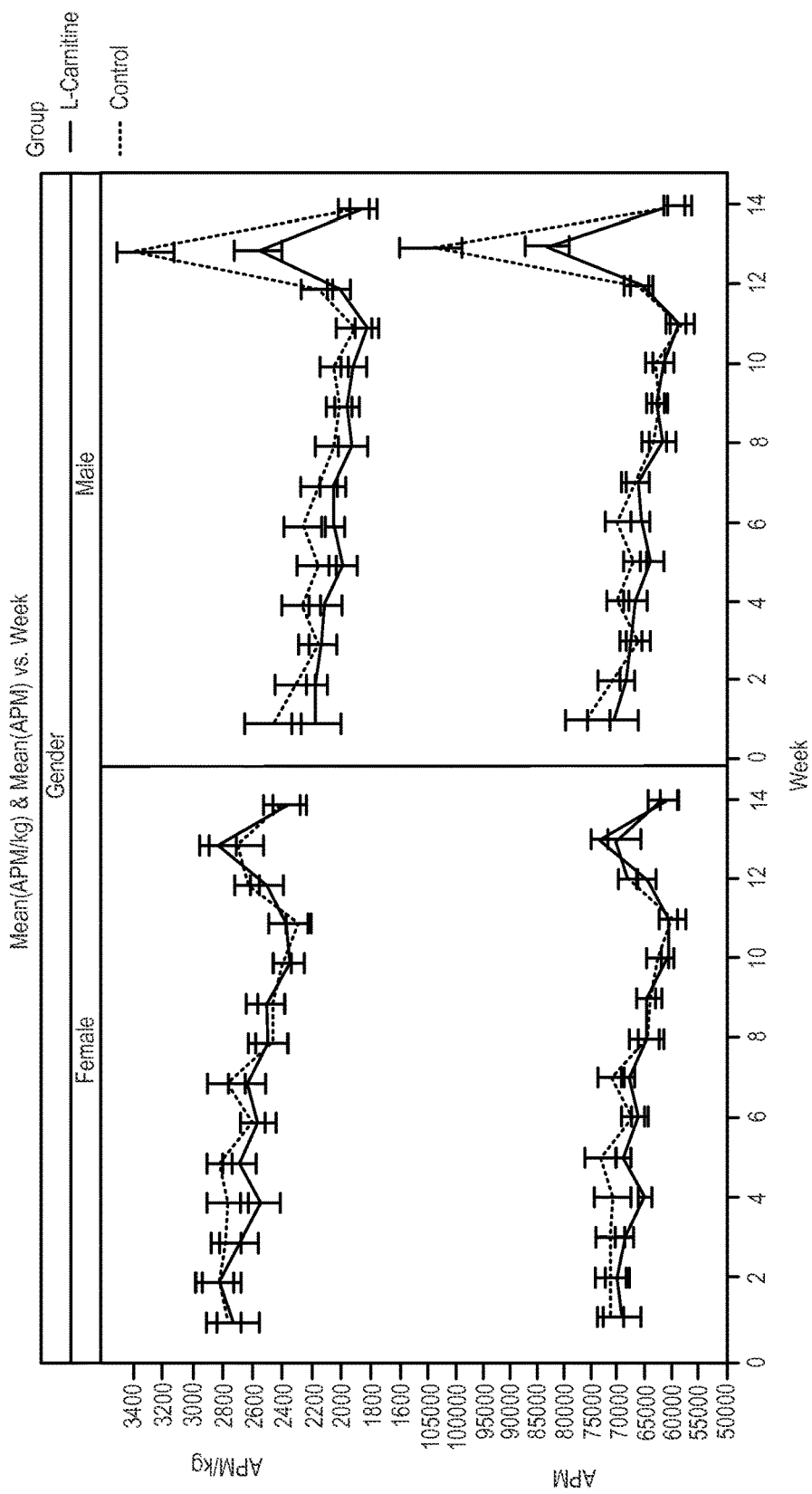
Figure 14C:
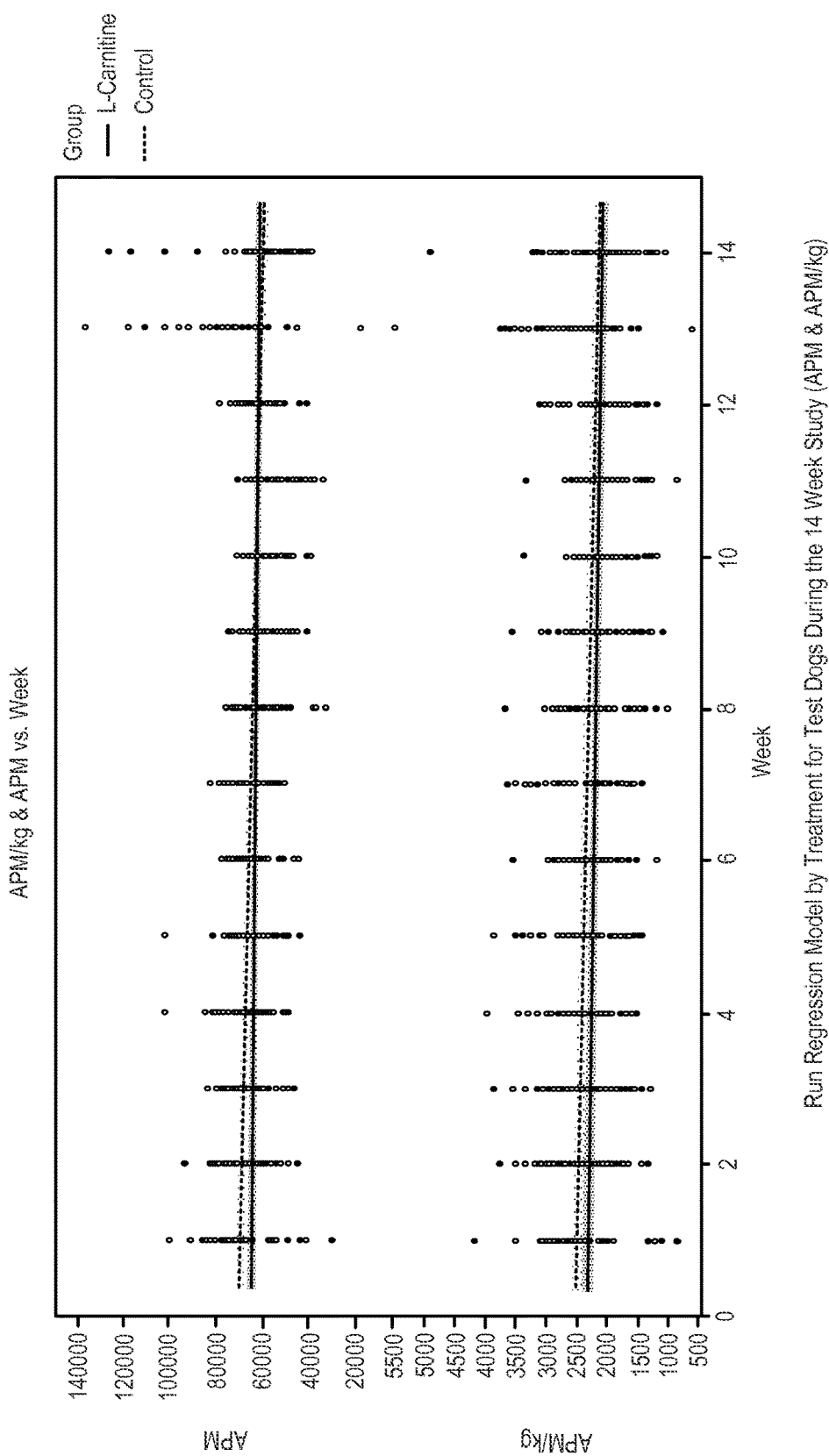
Figure 14D:
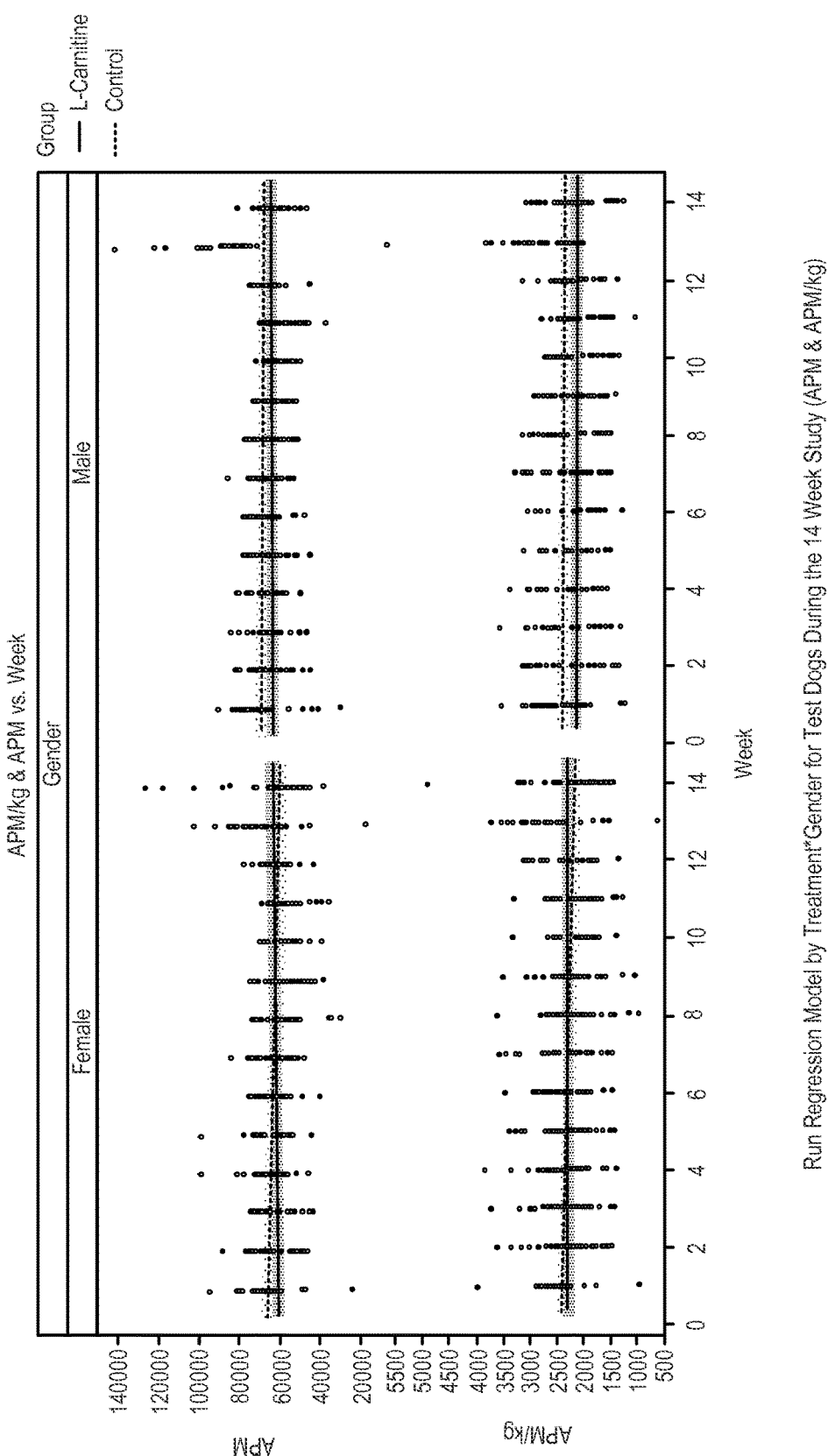

Overall, the control group had higher activity values throughout the course of the 14 week study. As FIGS. 12A and 13A illustrate, the control group had significantly higher values for activity/mile/kg BW (APM/kg) and activity/mile (APM) than did the L-carnitine group. Though there was no significant differences between the APM/kg or APM of the female control or L-carnitine dogs, the male control dogs demonstrated significantly higher APM/kg and APM than did the L-carnitine male dogs (FIGS. 12B and C and 13B and C). These results are reflected in the activity graphs and run regression models of FIGS. 14A, B, C, and D.

When looking at the crossover activity differences, however, the 19 L-carnitine dogs that were control dogs in Example 1 had significantly higher activity gains in both APM/kg and APM when compared to the 17 control dogs that were L-carnitine dogs in Example 1 (FIGS. 15A and B). The L-carnitine dogs (control dogs of Example 1) had an APM of 27,697 and a APM/kg of 975. In comparison, the control dogs (L-carnitine dogs of Example 1) had an APM of 18,867 and a APM/kg of 689 (p=0.04888 and p=0.0228, respectively).

Figure 16A:
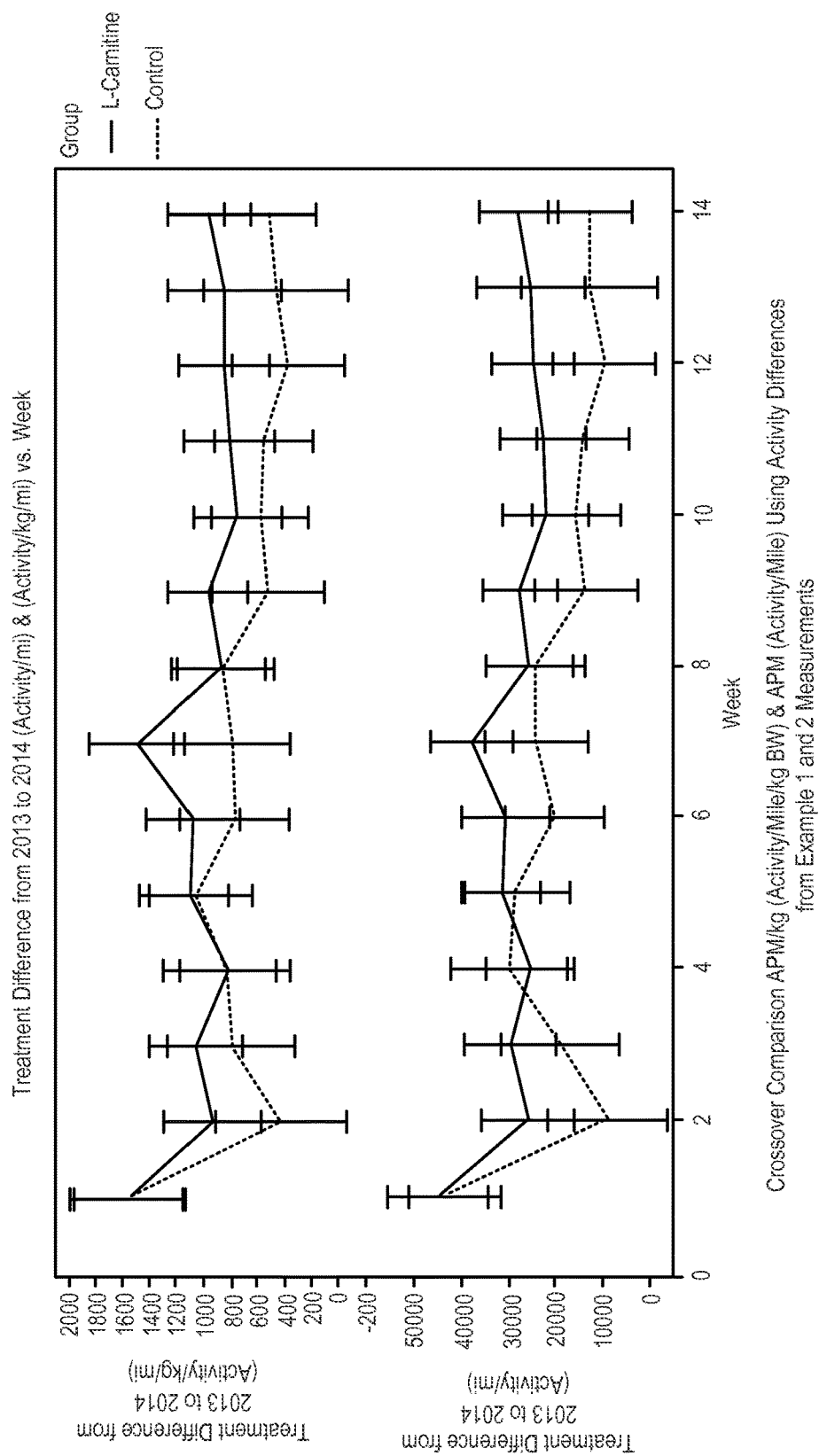
Figure 16B:
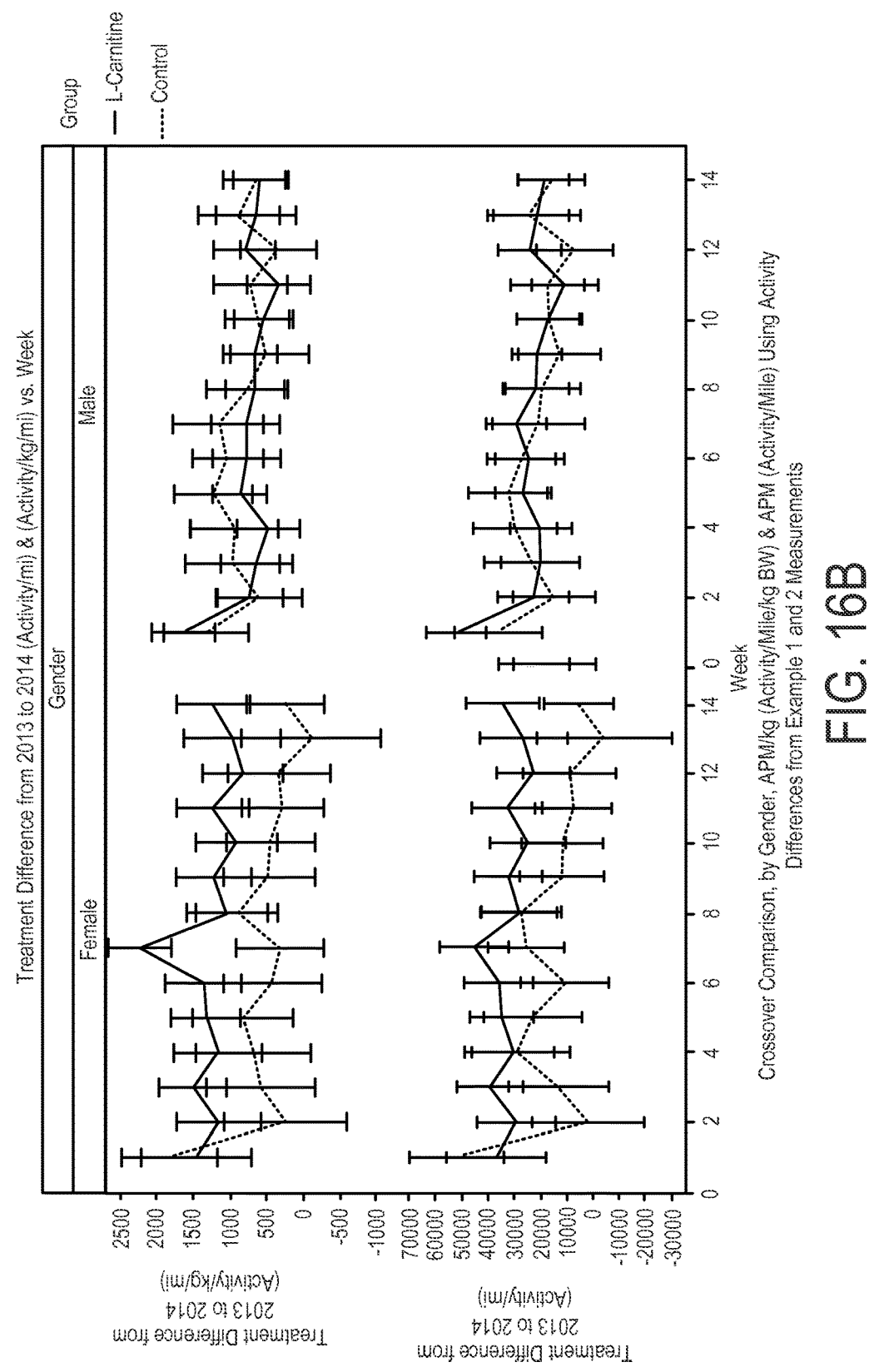
Figure 17A:
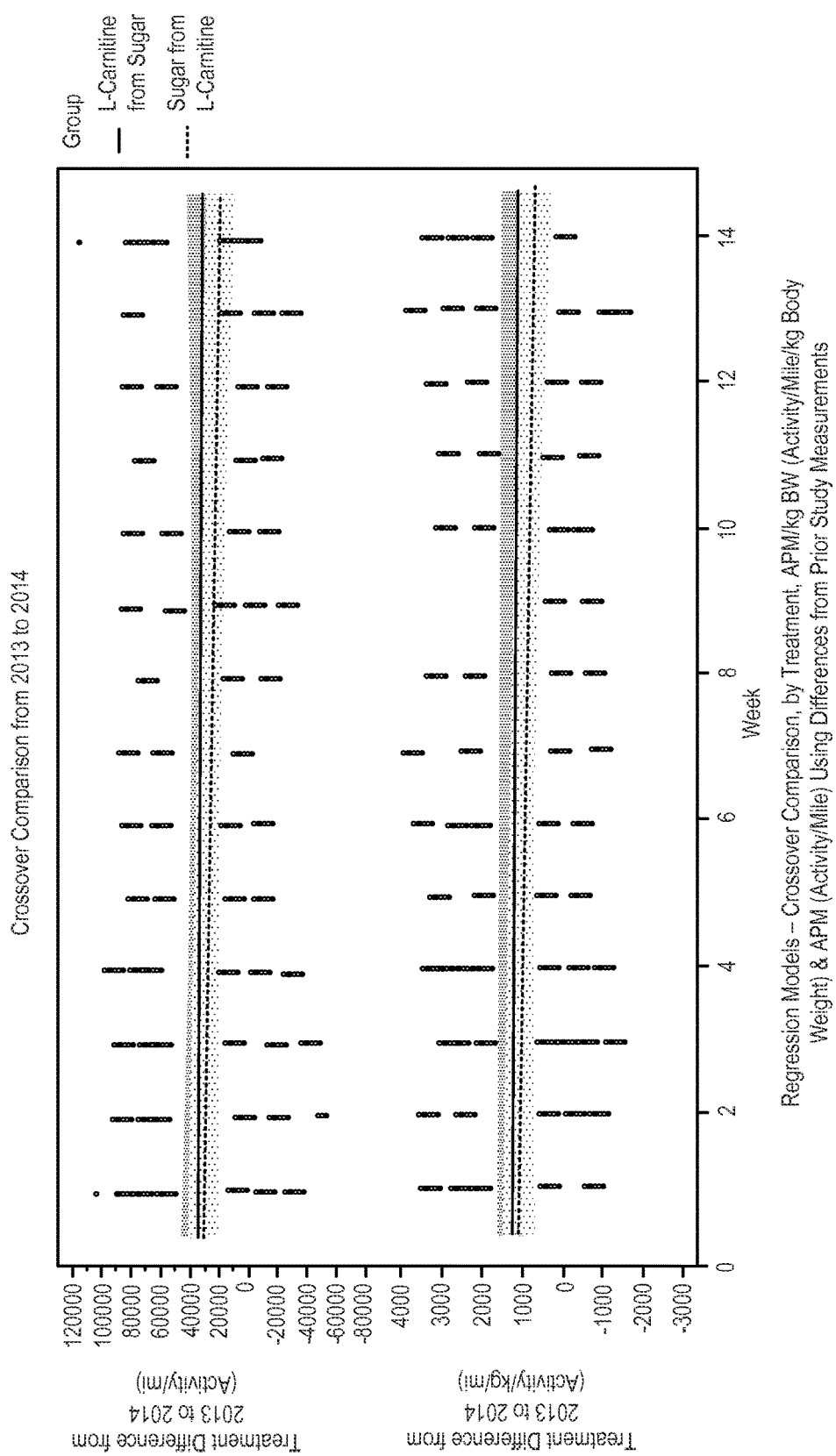
Figure 17B:
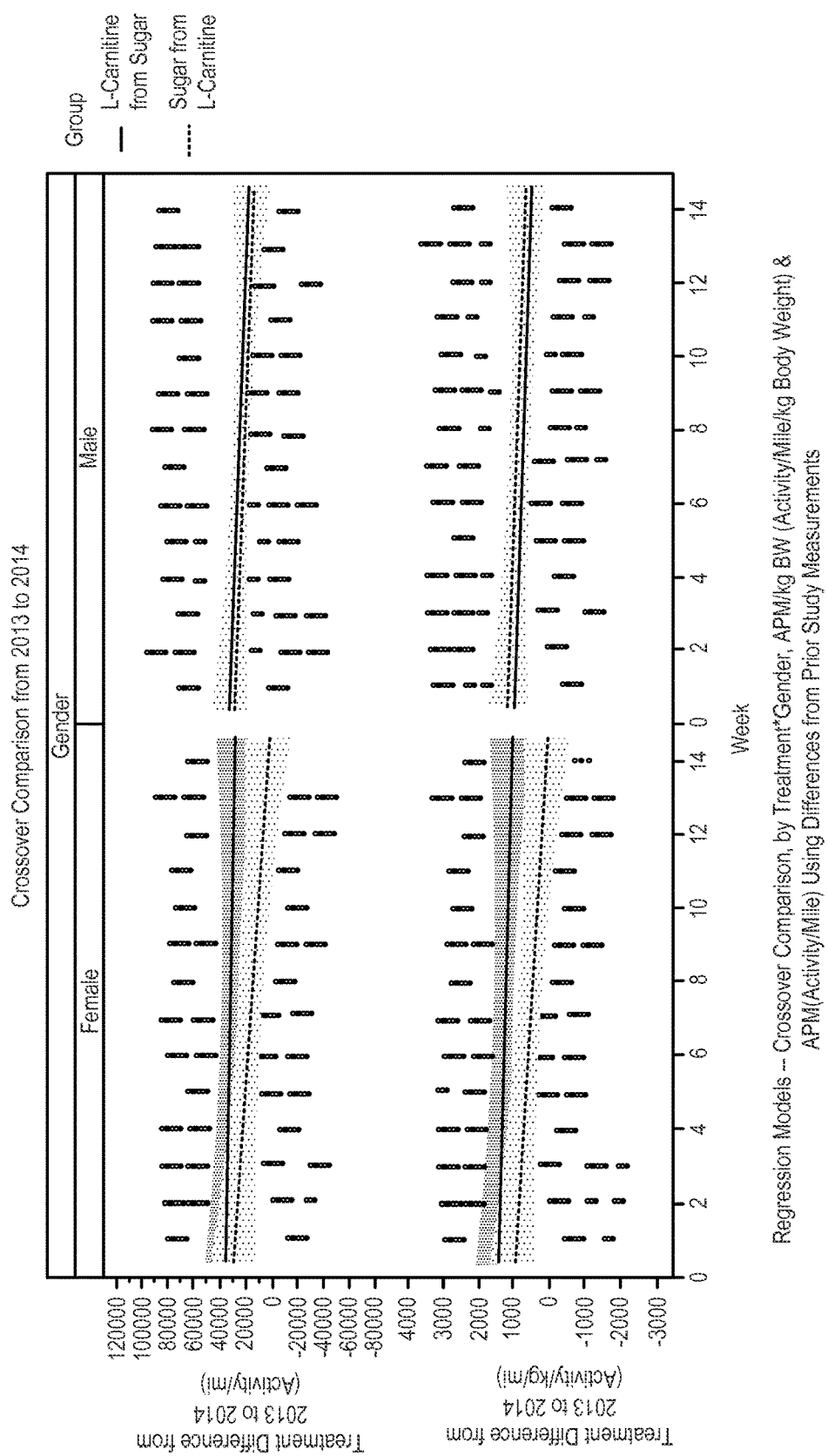

Both groups' activity numbers showed significant increases from the data collected in Example 1. The L-carnitine dogs demonstrated an increase in APM/kg from 1363 to 2274 (p<0.0001), while the control dogs had an increase from 1800 to 2400 (p<0.0001). The L-carnitine dogs also demonstrated an increase in APM from 37,621 to 63,272 (p<0.0001), while the control dogs had an increase from 51,861 to 67,456 (p<0.001). These results are reflected in the activity graphs and run regression models of FIGS. 16A and B and 17A and B.

The increased APM and APM/kg for the crossover L-carnitine dogs demonstrates that L-carnitine is playing a significant part in the crossover gains the carnitine dogs experience in comparison to the control dogs. In additional, part of the activity increase within each treatment may be attributed to the utilization of GPS tracking collars in this study, post-run 1 hour, and post-run 24 hour). The changes in blood biomarkers allow the individual dogs to be taken into account and provide additional support that L-carnitine is not only helping minimize muscle damage during the run but is also lowering peroxidation of membranes from stress involved with the final run. Overall, the biomarkers reveal that both male and female L-carnitine dogs had less muscle damage during the final long run.

TABLE 27

Levels of BloodbBiomarkers for Baseline, Pre-Run, and Post-Run Time Periods for Test Dogs Using a Mixed Statistical Model.

| | | L-carnitine | n = | Control | n = | P-Value |
|---|---|---|---|---|---|---|
| Whole Groups | | | | | | |
| Creatine Kinase (mU/mL) | Baseline | 23.63 ± 2.17 | 28 | 20.9 ± 1.77 | 28 | 0.3356 |
| | Pre-Run | 15.58 ± 1.4 | 28 | 16.28 ± 1.28 | 28 | 0.7136 |
| | Post-Run 1 Hr | 26.39 ± 0.96 | 28 | 26.63 ± 0.88 | 28 | 0.8523 |
| | Post-Run 24 Hr | 23.06 ± 0.88 | 28 | 28.37 ± 1.45 | 28 | 0.0028 |
| Myoglobin (ng/mL) | Baseline | 19.78 ± 4.13 | 28 | 19.92 ± 4.7 | 28 | 0.9819 |
| | Pre-Run | 6.78 ± 1.74 | 28 | 5.13 ± 0.73 | 28 | 0.3867 |
| | Post-Run 1 Hr | 23.83 ± 3.02 | 28 | 37.91 ± 4.77 | 28 | 0.0157 |
| | Post-Run 24 Hr | 6.25 ± 1.47 | 28 | 13.5 ± 2.61 | 28 | 0.0189 |
| TBARS (µM MDA) | Baseline | 13.77 ± 0.94 | 28 | 13.81 ± 0.87 | 28 | 0.9736 |
| | Pre-Run | 15.36 ± 1.55 | 28 | 23.42 ± 1.8 | 28 | 0.0013 |
| | Post-Run 1 Hr | 16.45 ± 1.43 | 28 | 20.65 ± 1.61 | 28 | 0.0561 |
| | Post-Run 24 Hr | 22.81 ± 2.01 | 28 | 28.64 ± 3.53 | 28 | 0.1568 |
| TAC (mM Trolox Equiv) | Baseline | 0.17 ± 0.01 | 28 | 0.16 ± 0.01 | 28 | 0.6992 |
| | Pre-Run | 0.14 ± 0.01 | 28 | 0.15 ± 0.01 | 28 | 0.7755 |
| | Post-Run 1 Hr | 0.15 ± 0.01 | 28 | 0.16 ± 0.01 | 28 | 0.7495 |
| | Post-Run 24 Hr | 0.16 ± 0.01 | 28 | 0.13 ± 0.01 | 28 | 0.0496 |
| FEMALES | | | | | | |
| Creatine Kinase (mU · mL) | Baseline | 26.44 ± 3.08 | 14 | 21.51 ± 2.89 | 14 | 0.2535 |
| | Pre-Run | 17.14 ± 1.96 | 14 | 15.79 ± 2.14 | 14 | 0.6475 |
| | Post-Run 1 Hr | 26.8 ± 1.36 | 14 | 26.79 ± 1.23 | 14 | 0.9971 |
| | Post-Run 24 Hr | 21.71 ± 0.79 | 14 | 27.21 ± 2.37 | 14 | 0.0369 |
| Myoglobin (ng/mL) | Baseline | 17.33 ± 4.7 | 14 | 27.22 ± 8.23 | 14 | 0.3061 |
| | Pre-Run | 4.88 ± 1.24 | 14 | 3.96 ± 0.8 | 14 | 0.5401 |
| | Post-Run 1 Hr | 25.19 ± 4.25 | 14 | 43.94 ± 8.03 | 14 | 0.0491 |
| | Post-Run 24 Hr | 8.08 ± 2.83 | 14 | 13.7 ± 3.71 | 14 | 0.2390 |
| TBARS (µM MDA) | Baseline | 13.03 ± 1.29 | 14 | 13.28 ± 1.32 | 14 | 0.8929 |
| | Pre-Run | 16.68 ± 2.16 | 14 | 23.23 ± 2.53 | 14 | 0.0596 |
| | Post-Run 1 Hr | 17.44 ± 2.26 | 14 | 20.46 ± 2.35 | 14 | 0.3627 |
| | Post-Run 24 Hr | 26.01 ± 3.09 | 14 | 33.12 ± 5.51 | 14 | 0.2710 |
| TAC (mM Trolox Equiv) | Baseline | 0.15 ± 0.01 | 14 | 0.13 ± 0.01 | 14 | 0.3602 |
| | Pre-Run | 0.13 ± 0.01 | 14 | 0.13 ± 0.01 | 14 | 0.7501 |
| | Post-Run 1 Hr | 0.15 ± 0.01 | 14 | 0.12 ± 0.01 | 14 | 0.1556 |
| | Post-Run 24 Hr | 0.16 ± 0.01 | 14 | 0.1 ± 0.01 | 14 | 0.0016 |
| MALES | | | | | | |
| Creatine Kinase (mU/mL) | Baseline | 20.81 ± 2.98 | 14 | 20.2 ± 1.98 | 14 | 0.8666 |
| | Pre-Run | 14.02 ± 1.98 | 14 | 16.84 ± 1.33 | 14 | 0.2471 |
| | Post-Run 1 Hr | 25.98 ± 1.39 | 14 | 26.45 ± 1.29 | 14 | 0.8075 |
| | Post-Run 24 Hr | 24.4 ± 1.53 | 14 | 29.7 ± 1.53 | 14 | 0.0214 |
| Myoglobin (ng/mL) | Baseline | 22.22 ± 6.92 | 14 | 11.49 ± 2.25 | 14 | 0.1525 |
| | Pre-Run | 8.69 ± 3.25 | 14 | 6.48 ± 1.2 | 14 | 0.5302 |
| | Post-Run 1 Hr | 22.46 ± 4.41 | 14 | 30.95 ± 3.99 | 14 | 0.1658 |
| | Post-Run 24 Hr | 4.41 ± 0.64 | 14 | 13.28 ± 3.82 | 14 | 0.0306 |
| TBARS (µM MDA) | Baseline | 14.51 ± 1.38 | 14 | 14.42 ± 1.13 | 14 | 0.9626 |
| | Pre-Run | 14.03 ± 2.24 | 14 | 23.64 ± 2.66 | 14 | 0.0104 |
| | Post-Run 1 Hr | 15.46 ± 1.79 | 14 | 20.87 ± 2.27 | 14 | 0.0723 |
| | Post-Run 24 Hr | 19.62 ± 2.38 | 14 | 23.48 ± 3.91 | 14 | 0.4059 |
| TAC (mM Trolox Equiv) | Baseline | 0.18 ± 0.01 | 14 | 0.19 ± 0.02 | 14 | 0.6774 |
| | Pre-Run | 0.15 ± 0.01 | 14 | 0.17 ± 0.03 | 14 | 0.5871 |
| | Post-Run 1 Hr | 0.16 ± 0.01 | 14 | 0.2 ± 0.02 | 14 | 0.0483 |
| | Post-Run 24 Hr | 0.16 ± 0.01 | 14 | 0.16 ± 0.02 | 14 | 0.8875 | which allowed for more accurate calculation of the actual miles each dog ran in determining its activity per mile.

Figure 18:
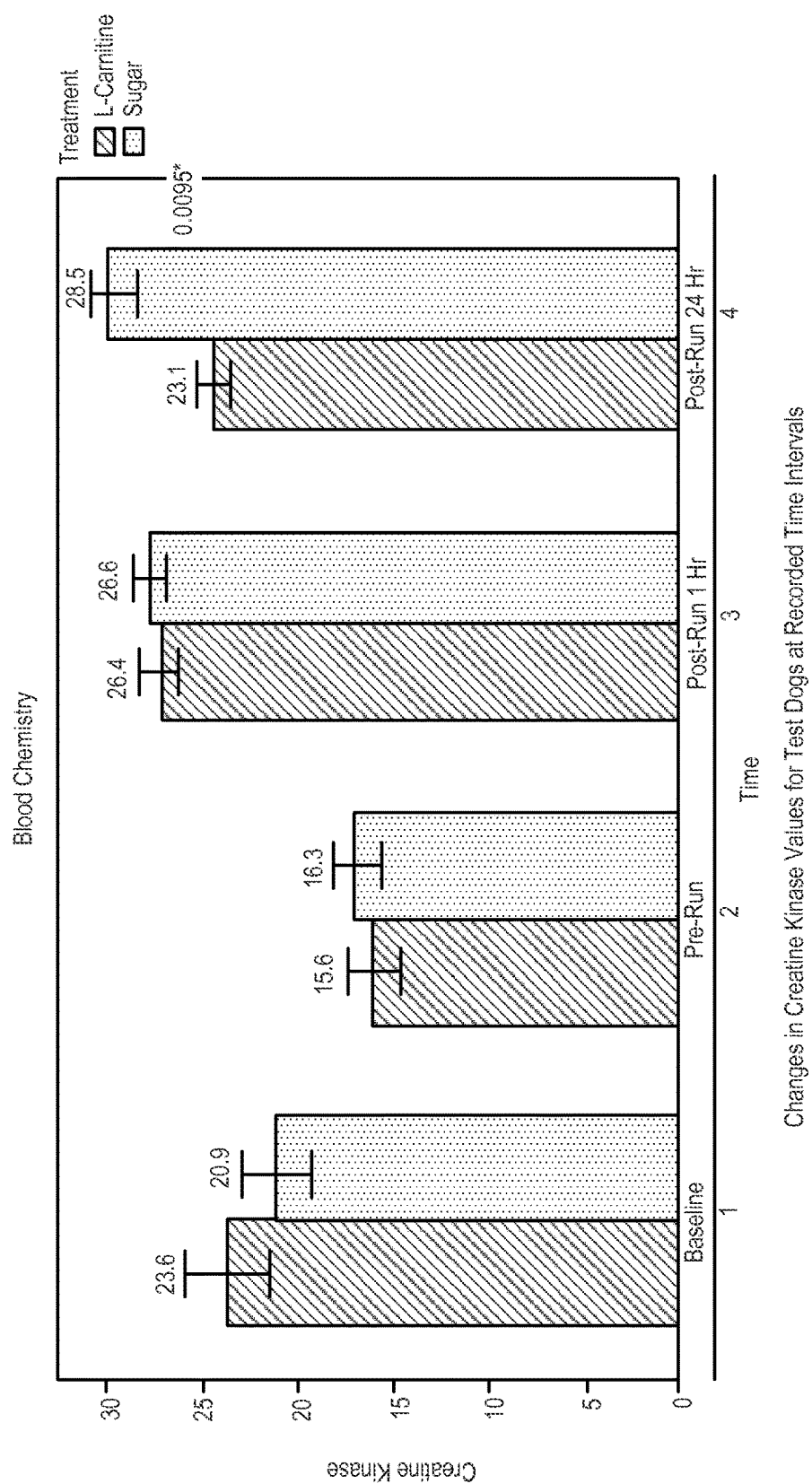

Table 27 contains the mean values by treatment and treatment by gender for each of the serum biomarkers (Creatine Kinase, myoglobin, TBARS, and TAC) at the different stages of training and exercise (baseline, pre-run, Creatine kinase (CK) values were compared for treatment differences at each time interval, as shown in FIG. 18. At the 1 hour post-endurance run interval, CK values had increased 10.81 units and 10.35 units from pre-run values for the L-carnitine and control groups, respectively. However, at the 24 hour post-run interval, CK values for the L-carnitine group had significantly decreased (from 26.39 to 23.06 mU/mL), while the levels for the control group had continued to increase (from 26.63 to 28.37 mU/mL) (p=0.0028). The control groups' increasing CK values indicate continued protein leakage due to muscle damage in the 24 hour period following the final endurance run (Table 27).

Figure 19:
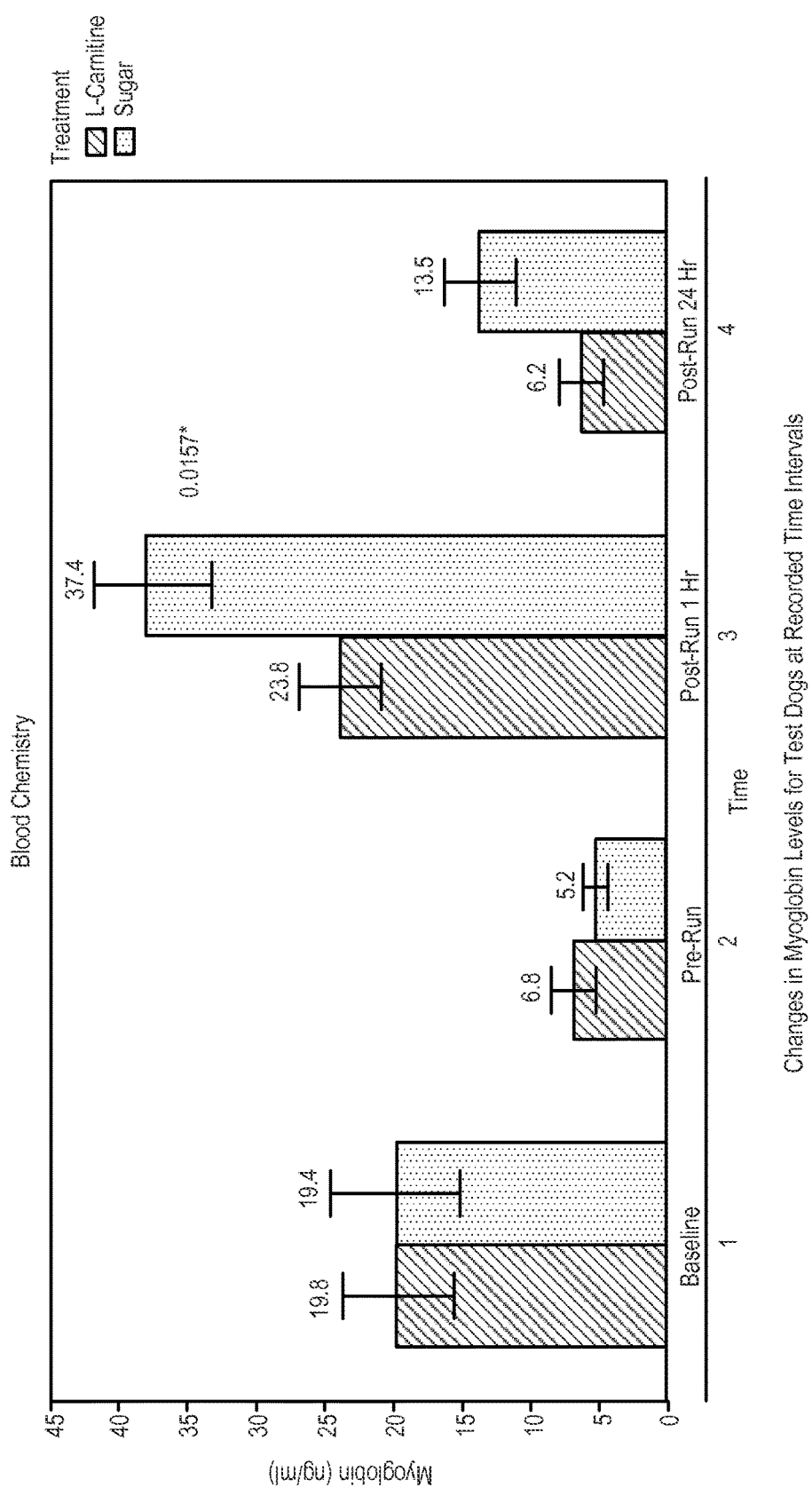

Myoglobin values were also compared for treatment differences, as shown in FIG. 19. The increase in myoglobin values after exercise at both post-run time intervals were considered significant (post-run 1 hr: P<0.001 & post-run 24 hr: P=0.0004). The control group had significantly elevated serum myoglobin values of 37.91 ng/mL compared to 23.83 ng/mL for the L-carnitine dogs (p=0.0157) at the post-run 1 hour time interval. At the post-run 24 hour time interval, the control group still maintained significantly higher myoglobin levels (13.5 ng/mL) than did the L-carnitine group (9.25 ng/mL), whose myoglobin levels had fallen back to pre-run levels. Thus, while both groups experienced increased myoglobin levels, indicating that they both incurred muscle injury, the significant decrease in the L-carnitine group's myoglobin levels at 24 hours post-run indicated that they accrued less damage and recovered more quickly than did the control dogs (Table 27). In particular, the control females had the largest increases in myoglobin, which indicates a direct response to skeletal muscle breakdown and protein degradation.

Figure 20:
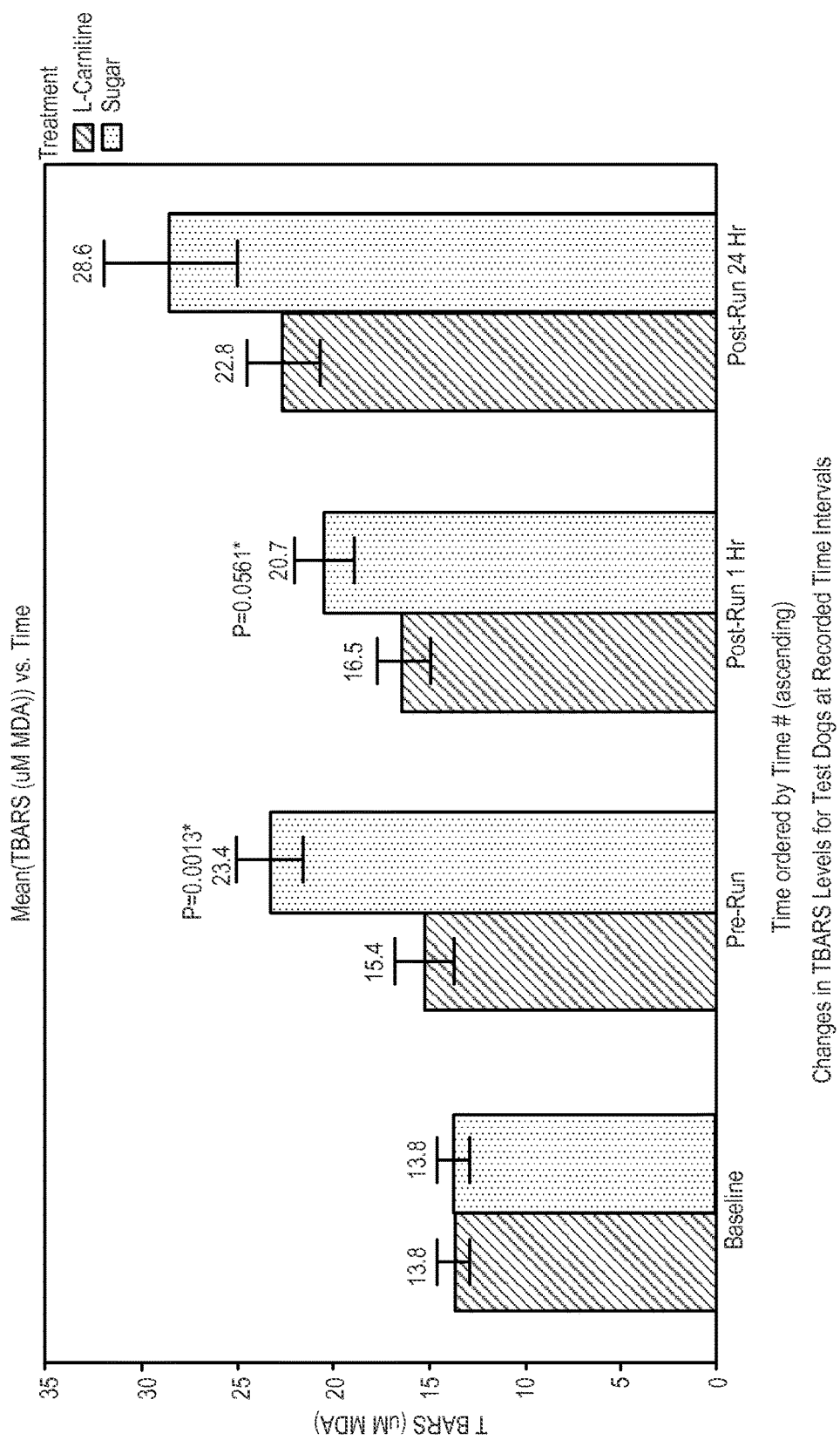

As the study progressed, thiobarbituric acid reactive substances (TBARS) levels in serum increased for both groups due to the damage that muscles incur naturally with exercise (FIG. 20). Prior to the 15 mile endurance run, the L-carnitine group had an average TBARS level of 15.36 µM malondialdehyde (MDA), which was significantly lower than the control group's 23.42 µM MDA (p=0.0013). Following the endurance run, significantly lower levels of MDA were found in the L-carnitine group than the control group (16.45 µM vs. 20.65 µM MDA; p=0.0561) at the post-run 1 hr interval (Table 27). The lower levels of MDA in the L-carnitine group indicates that a much lower rate of lipid peroxidation is taking place in the L-carnitine dogs during the oxidative stress of the final long run. In comparison, the increased levels of MDA in the control group indicate that lipid products are being degraded at a much higher rate in the control dogs. The higher levels of TBARS in the female dogs indicate more lipid degradation of membranes, which fits the significant increase in myoglobin among females following the final run.

Figure 21:
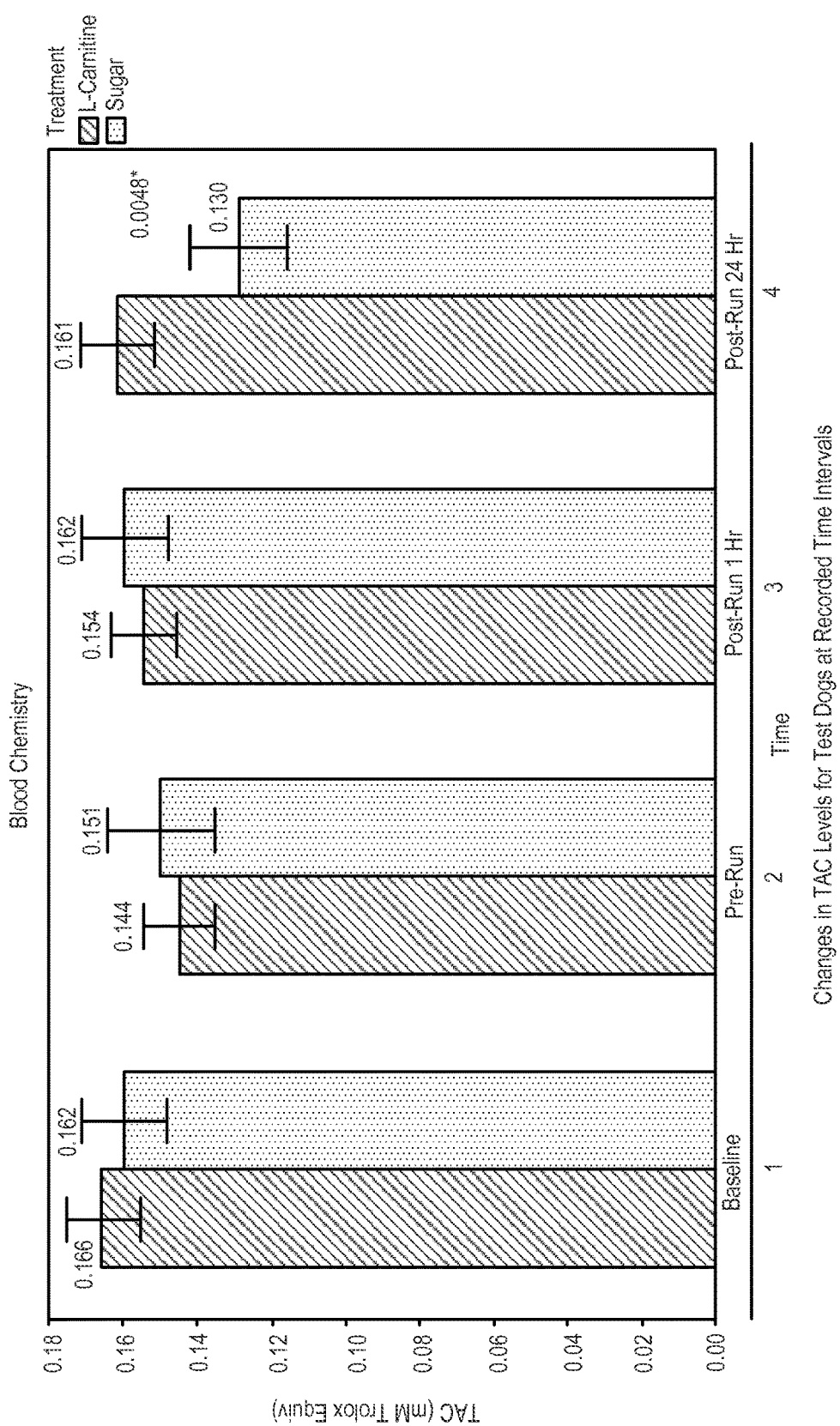

In comparison to basal levels, total antioxidant capacity (TAC) for both groups decreased over the 14 week increasing training regiment, but antioxidant capacity values were significantly increased at the post-run 24-hr interval (FIG. 21). At the post-run 24-hr interval, the L-carnitine group's TAC levels reached 0.16 (mM Trolox equiv) while the control group's TAC levels fell to 0.13 (mM Trolox equiv) (p=0.0496). The lower TAC levels in the control group indicate that the control dogs had to use the antioxidant capacity to neutralize free radicals in order to deal with the oxidative stress that is involved in running the 15 mile final endurance run (Table 27).

Figure 22A:
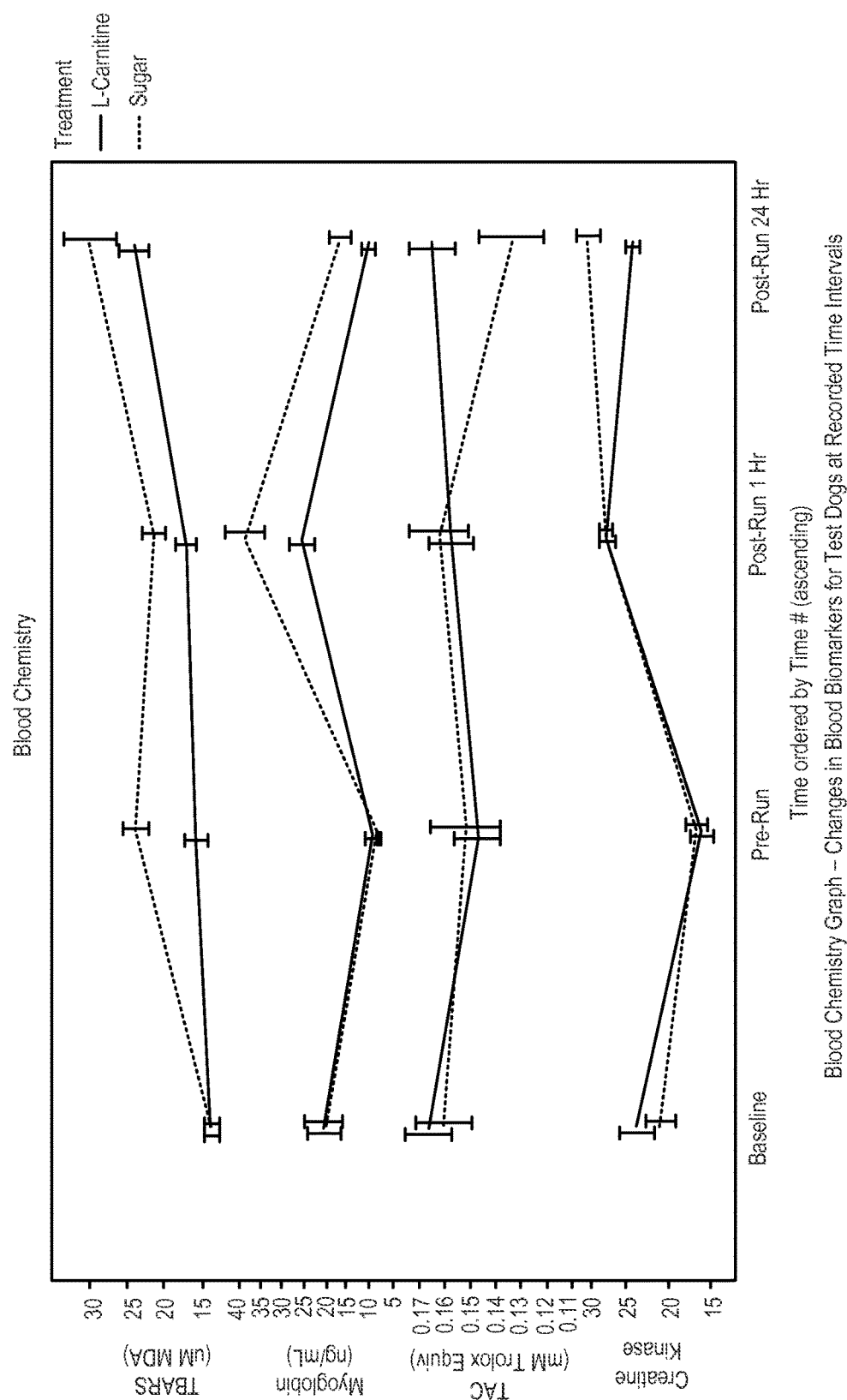
Figure 22B:
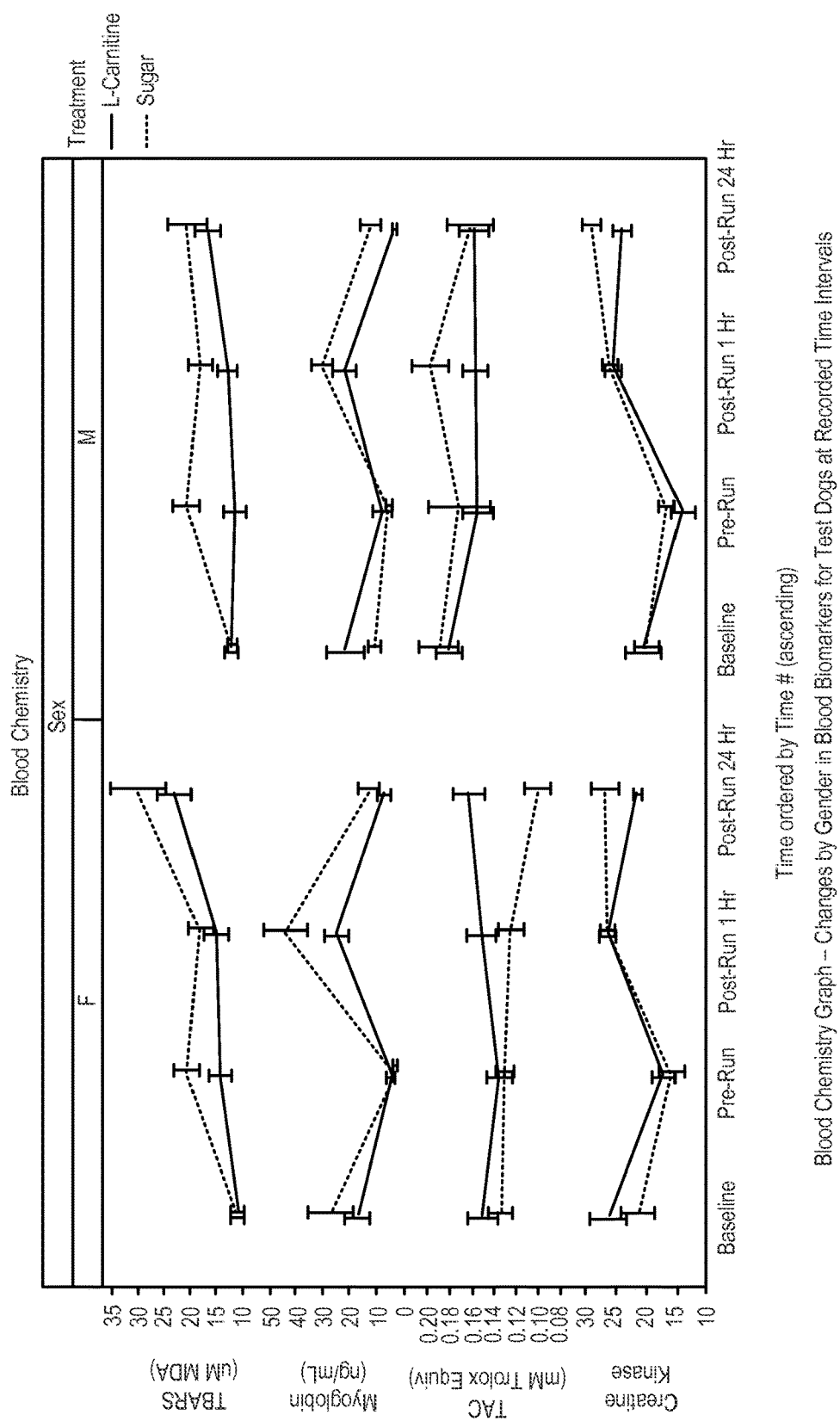

The CK, myoglobin, TBARS, and TAC values by treatment group and gender are summarized in FIGS. 22A and B.

Table 28 demonstrates the body composition for the performance dogs. The percent fat, total tissue mass (kg), lean mass (LM) (kg), grams of bone mineral content (BMC), fat (kg), and g/cm² were reported by sex, treatment, and time.

TABLE 28

Body composition Values for Test Dogs by Time * Treatment and Time * Treatment * Gender.

| | Body Composition Stats | L-carnitine | | Control | | P-Value |
|---|---|---|---|---|---|---|
| By Treatment & Time | (% Fat, Change) | 1.04 ± 0.71 | n = 28 | 1.48 ± 0.73 | n = 28 | 0.6636 |
| | (% Fat, Final) | 16.62 ± 1.06 | n = 28 | 17.5 ± 1.23 | n = 28 | 0.5885 |
| | (% Fat, Initial) | 15.58 ± 1.2 | n = 28 | 16.02 ± 1.35 | n = 28 | 0.8089 |
| | (Total Tissue (kg), Change) | 0.74 ± 0.16 | n = 28 | −0.12 ± 0.17 | n = 28 | 0.0006 |
| | (Total Tissue (kg), Final) | 27.5 ± 0.84 | n = 28 | 26.41 ± 0.79 | n = 28 | 0.3479 |
| | (Total Tissue (kg), Initial) | 26.76 ± 0.83 | n = 28 | 26.53 ± 0.78 | n = 28 | 0.8382 |
| | (Lean Mass (kg), Change) | 0.68 ± 0.16 | n = 28 | −0.41 ± 0.17 | n = 28 | <.0001 |
| | (Lean Mass (kg), Final) | 23.24 ± 0.79 | n = 28 | 21.82 ± 0.71 | n = 28 | 0.1879 |
| | (Lean Mass (kg), Initial) | 22.56 ± 0.74 | n = 28 | 22.23 ± 0.69 | n = 28 | 0.7434 |
| | (BMC (g), Change) | 8.04 ± 4.62 | n = 28 | 9.03 ± 5.07 | n = 28 | 0.8859 |
| | (BMC (g), Final) | 821.95 ± 28.14 | n = 28 | 791.82 ± 27.28 | n = 28 | 0.4455 |
| | (BMC (g), Initial) | 813.91 ± 28.38 | n = 28 | 782.8 ± 26.6 | n = 28 | 0.4273 |
| | (Fat (kg), Change) | 0.39 ± 0.2 | n = 28 | 0.32 ± 0.21 | n = 28 | 0.8207 |
| | (Fat (kg), Final) | 4.59 ± 0.33 | n = 28 | 4.62 ± 0.35 | n = 28 | 0.9483 |
| | (Fat (kg), Initial) | 4.2 ± 0.35 | n = 28 | 4.3 ± 0.38 | n = 28 | 0.8533 |
| | (BMD (g/cm2), Change) | 0.007 ± 0.003 | n = 28 | 0.001 ± 0.005 | n = 28 | 0.3054 |
| | (BMD (g/cm2), Final) | 0.61 ± 0.01 | n = 28 | 0.61 ± 0.01 | n = 28 | 0.6086 |
| | (BMD (g/cm2), Initial) | 0.608 ± 0.01 | n = 28 | 0.605 ± 0.011 | n = 28 | 0.8252 |
| By Treatment, Time & Gender | (% Fat, Female, Change) | 1.58 ± 1.29 | n = 14 | 3.01 ± 1.01 | n = 14 | 0.3893 |
| | (% Fat, Female, Final) | 18.43 ± 1.75 | n = 14 | 19.75 ± 1.54 | n = 14 | 0.5742 |
| | (% Fat, Female, Initial) | 16.85 ± 2.1 | n = 14 | 16.74 ± 2.17 | n = 14 | 0.9712 |
| | (% Fat, Male, Change) | 0.49 ± 0.61 | n = 14 | −0.29 ± 0.82 | n = 14 | 0.4500 |
| | (% Fat, Male, Final) | 14.81 ± 1.05 | n = 14 | 14.9 ± 1.75 | n = 14 | 0.9640 |
| | (% Fat, Male, Initial) | 14.31 ± 1.16 | n = 14 | 15.19 ± 1.53 | n = 14 | 0.6520 |
| | (Total Tissue (kg), Female, Change) | 0.78 ± 0.27 | n = 14 | −0.22 ± 0.25 | n = 14 | 0.0117 |
| | (Total Tissue (kg), Female, Final) | 24.34 ± 0.94 | n = 14 | 23.95 ± 0.7 | n = 14 | 0.7400 |
| | (Total Tissue (kg), Female, Initial) | 23.56 ± 0.86 | n = 14 | 24.17 ± 0.71 | n = 14 | 0.5886 |
| | (Total Tissue (kg), Male, Change) | 0.7 ± 0.19 | n = 14 | 0.01 ± 0.22 | n = 14 | 0.0268 |
| | (Total Tissue (kg), Male, Final) | 30.67 ± 0.72 | n = 14 | 29.25 ± 1.05 | n = 14 | 0.2780 |
| | (Total Tissue (kg), Male, Initial) | 29.97 ± 0.75 | n = 14 | 29.25 ± 1.07 | n = 14 | 0.5870 |
| | (Lean Mass (kg), Female, Change) | 0.45 ± 0.21 | n = 14 | −0.84 ± 0.26 | n = 14 | 0.0006 |
| | (Lean Mass (kg), Female, Final) | 19.95 ± 0.65 | n = 14 | 19.26 ± 0.65 | n = 14 | 0.4648 |
| | (Lean Mass (kg), Female, Initial) | 19.49 ± 0.69 | n = 14 | 20.1 ± 0.76 | n = 14 | 0.5570 |

TABLE 28-continued

Body composition Values for Test Dogs by Time * Treatment and Time * Treatment * Gender.

| Body Composition Stats | L-carnitine | | Control | | P-Value |
|---|---|---|---|---|---|
| (Lean Mass (kg), Male, Change) | 0.91 ± 0.22 | n = 14 | 0.09 ± 0.15 | n = 14 | 0.0050 |
| (Lean Mass (kg), Male, Final) | 26.54 ± 0.71 | n = 14 | 24.77 ± 0.74 | n = 14 | 0.0973 |
| (Lean Mass (kg), Male, Initial) | 25.63 ± 0.58 | n = 14 | 24.68 ± 0.75 | n = 14 | 0.3265 |
| (BMC (g), Female, Change) | 9.54 ± 6.72 | n = 14 | 8.95 ± 7.15 | n = 14 | 0.9531 |
| (BMC (g), Female, Final) | 716.5 ± 30.63 | n = 14 | 712.18 ± 25.49 | n = 14 | 0.9145 |
| (BMC (g), Female, Initial) | 706.96 ± 30.19 | n = 14 | 703.23 ± 27.49 | n = 14 | 0.9278 |
| (BMC (g), Male, Change) | 6.54 ± 6.57 | n = 14 | 9.11 ± 7.48 | n = 14 | 0.7981 |
| (BMC (g), Male, Final) | 927.39 ± 25.32 | n = 14 | 883.72 ± 37.66 | n = 14 | 0.3447 |
| (BMC (g), Male, Initial) | 920.86 ± 25.96 | n = 14 | 874.61 ± 33.19 | n = 14 | 0.2824 |
| (Fat (kg), Female, Change) | 0.56 ± 0.35 | n = 14 | 0.67 ± 0.27 | n = 14 | 0.7981 |
| (Fat (kg), Female, Final) | 4.62 ± 0.57 | n = 14 | 4.74 ± 0.39 | n = 14 | 0.8658 |
| (Fat (kg), Female, Initial) | 4.07 ± 0.59 | n = 14 | 4.07 ± 0.54 | n = 14 | 0.9997 |
| (Fat (kg), Male, Change) | 0.22 ± 0.2 | n = 14 | −0.08 ± 0.28 | n = 14 | 0.3944 |
| (Fat (kg), Male, Final) | 4.56 ± 0.36 | n = 14 | 4.49 ± 0.62 | n = 14 | 0.9200 |
| (Fat (kg), Male, Initial) | 4.34 ± 0.42 | n = 14 | 4.57 ± 0.55 | n = 14 | 0.7416 |
| (BMD (g/cm2), Female, Change) | 0.0029 ± 0.005 | n = 14 | 0 ± 0.01 | n = 14 | 0.9820 |
| (BMD (g/cm2), Female, Final) | 0.58 ± 0.01 | n = 14 | 0.58 ± 0.01 | n = 14 | 0.9102 |
| (BMD (g/cm2), Female, Initial) | 0.58 ± 0.01 | n = 14 | 0.58 ± 0.01 | n = 14 | 0.9541 |
| (BMD (g/cm2), Male, Change) | 0.011 ± 0.005 | n = 14 | 0 ± 0.01 | n = 14 | 0.1564 |
| (BMD (g/cm2), Male, Final) | 0.65 ± 0.01 | n = 14 | 0.64 ± 0.01 | n = 14 | 0.4941 |
| (BMD (g/cm2), Male, Initial) | 0.64 ± 0.01 | n = 14 | 0.64 ± 0.01 | n = 14 | 0.9420 |

Unpaired t-test.
Data displayed indicates mean ± SEM.
Differing letters indicates significant difference (P < 0.05).

Figure 23A:
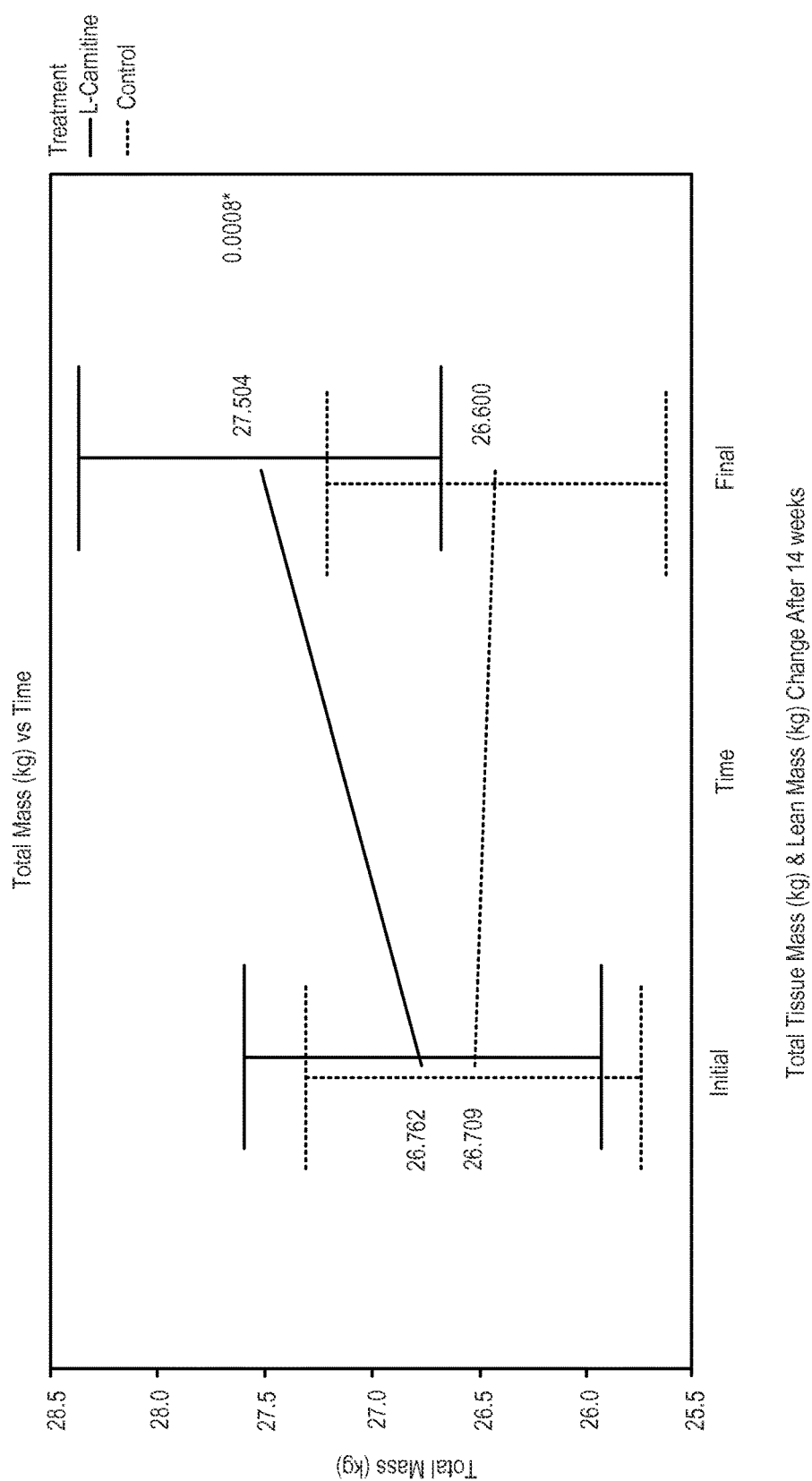
Figure 23B:
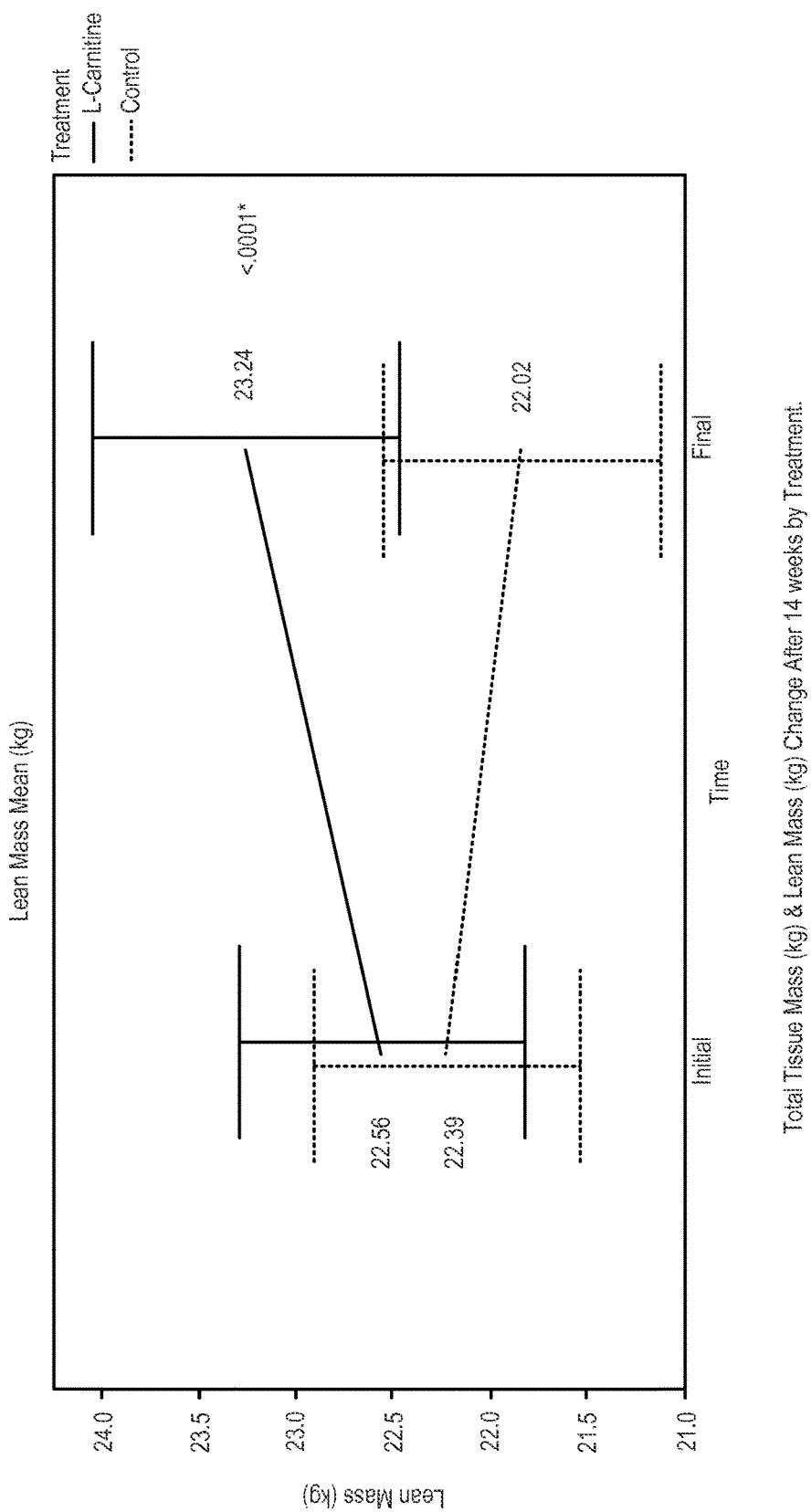

Due to their ability to maintain and increase lean mass, the L-carnitine group saw a significant total tissue mass increase (0.74 kg) in comparison to the control group's loss of total tissue mass (−0.12 kg) (p=0.0006) (FIGS. 23A and B; FIG. 24A). Both the male and female L-carnitine groups experienced a statistically significant total tissue mass increase (0.70 kg; p=0.0268 and 0.78 kg; p=0.0117, respectively). The female control group experienced a loss in total tissue mass of 0.22 kg, while the control male yielded essentially no change (0.01 kg) in total tissue mass by the end of the part one (FIGS. 24B and C). Both genders and treatment groups experienced small numerical increases in fat mass (kg) and % fat. The female L-carnitine dogs showed a numerically lower increase in % fat mass (1.58% vs 3.01%) (p=0.3893) compared to the control females, indicating that the L-carnitine females were able to utilize fat as fuel while the control females experienced increased lipid peroxidation and protein degradation (Table 28). Overall, gains in total mass, percentage fat, bone mineral content, and bone mineral density were not considered statistically significant between groups.

Dogs within both treatment groups and both genders incurred total tissue mass changes that were concomitant with lean mass changes, within their specific treatment groups, over the duration of the study (FIGS. 23A and B). As shown in FIG. 25A, the L-carnitine dogs had an average increase of 0.68 kg in LM, while the control dogs had a 0.41 kg decrease (p<0.0001). The female L-carnitine dogs gained 0.45 kg LM, while the female control dogs had a 0.84 kg LM decreased (p=0.0006) (FIG. 25B). As FIG. 25C illustrates, the male L-carnitine dogs gained 0.91 kg LM during the course of the study, while the male control dogs only gained 0.09 kg LM (p=0.0050). These results reveal that L-carnitine can not only lead to increased lean muscle mass but can also efficiently preserve and prevent muscle damage in working Labrador Retrievers.

Part Two: In part two of the study, L-carnitine was shown to decrease the rate of skeletal muscle breakdown. Twenty-six Labrador Retrievers ranging in age from 1.5 to 4.5 years were chosen from part one of the study and were fed for an additional 60 days following the termination of part one of the study. Test dogs remained in their previous treatment groups. Measurements on Actical movements/kg BW/mile endurance runs obtained during part one of the study were utilized to ensure that both the control and the L-carnitine groups were equal for performance potential. The lean body mass of the test dogs was determined by scanning with the DEXA as an additional measure for ensuring equal groups. Twelve dogs (6 males and 6 females) were assigned to each treatment group. Two additional dogs (1 male and 1 female) were fed the low carnitine basal diet of the control group and were used as controls that were not enriched with isotopes during the study; these two control dogs were used to measure the natural amount of 15N Phe in the sample.

During the 60 day trial, the test dogs were fed low-carnitine basal diets with or without L-carnitine supplementation in a manner analogous to that of part one of the study. For three days prior to the final muscle biopsy and blood collection, all test dogs were feed an "all vegetarian plus egg" diet from Purina LabDiet that had nutrient specifications that were equivalent to that of the low carnitine basal diet. GC-MS analysis revealed that the "all vegetarian plus egg" diet had no 3-methylhistidine.

The body composition of each dog was measured, once on the first day of part one of the study and again after the completion of part two, as described in Example 1. The test dogs were also weighed as in part one.

Each group of dogs was put through two different types of exercise programs on a weekly basis representing both sprint and endurance type work outs. The two weekly endurance runs began at 5 miles per run and increased 1 mile per week to a distance of 10 miles per run on the $6^{th}$ week. During the $7^{th}$ week, the first endurance run was 5 miles while the second was a 2 mile taper run. Every week during the 60 period, one endurance run was a steady state run to increase aerobic capacity while the second endurance run was a steady state run interspersed with Fartlek, or speed play, running. The weekly Fartlek running represented 20% of the total distance for one of the weekly endurance runs, and the total distance of the sprint type Fartlek running increased as the distance of each endurance run increased each week. Like in part one, the weekly steady state endurance type run was at a pace equivalent to 50%-65% VO2 max.

Each dog wore an Actical monitor and a Garmin Astro DC50 connected to a Astro 320 receiver for movement evaluation and tracking throughout each run. The data from each device was downloaded onto the computer to compute the actual Actical activity/kg BW/mile for each dog.

Twelve dogs (3 male and 3 female control dogs and 3 male and 3 female L-carnitine dogs) participated in the final 15 mile timed endurance run. Following the 15 mile run, the dogs' heart rate and body temperature were determined as in Example 1.

Eight (4 male and 4 female) of the control dogs and 6 (3 male and 3 female) of the L-carnitine dogs did not participate in the final 15 mile endurance run. These dogs represented the trained and rested physiological state for the study.

At the end of the 60 day training program, 24 of the dogs (12 resting and 12 running) were infused with a bolus dose of 15N Phe. First, the twelve rested test dogs were infused with a 2% 15N Phe (105 mL/dog) solution (40 APE) over a 10 min time period at a rate of 70 mg/kg BW (40 MPE). Forty-five minutes after infusion, a 5 mm Bergstrom muscle biopsy needle was used to take a biopsy of the biceps femoris muscle. The muscle samples were quickly frozen in liquid nitrogen and placed in a −80° C. freezer for later analysis].

Twenty-four hours after the resting dogs were infused with 15N Phe, the remaining 12 dogs (6 non-carnitine; 3 male and 3 female and 6 L-carnitine; 3 male and 3 female) were run for a 15 mile endurance run. Following a 30 minute period of measured physiological recovery (heart rate and body temperature), test dogs that completed the 15 mile run were infused with a 2% 15N Phe solution as described above; muscle biopsies were taken 45 minutes after infusion.

Two of the control dogs who were fed the low Carnitine basal diet were biopsied in the same manner as the other test dogs but were not infused with 15N Phe prior to the biopsy. These dogs represented the control that was trained but not infused with stable isotopes in the study.

Blood samples were taken from the carotid artery for each test dog and analyzed for 3 MH. Three days prior to taking the blood samples, the dogs were fed the "all vegetable plus egg" non-meat diet from Purina LabDiet to ensure that the 3 MH found in the blood represented the skeletal muscle protein breakdown.

To process the samples, the acid-soluble fraction containing free amino acids was removed by addition of 2% (w/v) perchloric acid. After homogenization, samples were centrifuged at 3,000×g, and the supernatant, containing free amino acids, was removed. The protein precipitate was washed three times with 2% perchloric acid before being hydrolyzed in 6N HCL. The supernatant and precipitate, respectively, were then run through an ion-exchange column packed with Dowex 50WX8-200. Phenylalanine and 3-methylhistidine (3-MH) were eluted with 2 mL of 4N NH4OH and 1 mL of nanopure $H_2O$ into a new vial and then dried under vacuum. The tert-butyldimethylsilyl (tBDMS) derivative was formed by adding 800 µL of C2CH3CN-MTBSTFA (1:1) and incubating at 110° C. for 60 minutes.

Analysis of the protein precipitate of muscle samples and free amino acids were carried out on an Agilent 7890A GC system attached to an Agilent 6975C mass spectrometer. Helium was used as the carrier gas at 1 mL/min. A 1 µL volume was injected into the GC/MS in splitless mode. Oven temperature began at 150° C. and increased by 50° C./min until reaching 200° C., after which the temperature was increased by 20° C./min until reaching 270° C. The temperature was held at 270° C. for 5.5 minutes. The mass spectrometer was operated under EI and SIM modes. The 394 and 395 m/z fragments, which represented the M and M+1 fragments of phenylalanine, were monitored.

The same mass spectrometer was used to determine 3-MH. Helium was used as the carrier gas at 1 mL/min, and 1 µL volume was injected into the GC/MS in splitless mode. Oven temperature was held at 110° C. for 0.65 minutes and then increased by 30° C./min until reaching 250° C. The temperature was held at 250° C. for 10 minutes. The 238 m/z fragment of 3-MH was monitored.

The muscle samples were analyzed for the fractional breakdown rate (FBR). FBR was calculated as kd=3-MH daily excretion/3-MH muscle pool×100. Table 29 shows that, when adjusted for gender and exercise state, feeding the dogs L-carnitine decreased the FBR from 3.70% to 1.92% (p=0.042). The lower FBR in the L-carnitine test dogs demonstrates a decrease in protein degradation, indicating that the presence of L-carnitine prevents muscle breakdown. Thus, the L-carnitine test dogs had increased lean mass during part one of the study because they are degrading less muscle mass during the runs.

TABLE 29

Fractional Breakdown Rate (FBR) of Muscle Samples by Treatment

| Treatment | FBR |
| --- | --- |
| Control | 3.70 |
| L-carnitine | 1.92 |
| P value | 0.042 |
| SEM | 0.56 |

Overall, females had a significantly higher FBR than males (F 3.70 vs M 1.93; p=0.044) (Table 30).

TABLE 30

Fractional Breakdown Rate (FBR) of Muscle Samples by Gender

| Gender | FBR |
| --- | --- |
| Female | 3.70 |
| Male | 1.93 |
| P value | 0.044 |
| SEM | 0.56 |

In Table 31, exercised female dogs had a significantly higher FBR than female dogs who were not exercised or male dogs whether exercised or not (p=0.038).

TABLE 31

Fractional Breakdown Rate (FBR) of Muscle Samples by Gender and Exercise

| Gender | FBR |
| --- | --- |
| Female, no run | 2.25[b] |
| Female, run | 5.14[a] |
| Male, no run | 2.31[b] |

TABLE 31-continued

Fractional Breakdown Rate (FBR) of Muscle Samples by Gender and Exercise

| Gender | FBR |
| --- | --- |
| Male, run | 1.54[b] |
| P value | 0.038 |
| SEM | 0.79 |

Levels not connected by the same letter are significantly different

Table 32 shows that exercised L-carnitine females had a significantly lower FBR than did the exercised control dogs; the female control dogs that ran the endurance run had a 7% FBR (% protein breakdown rate/day) of skeletal muscle compared to 3.26% FBR for the L-carnitine females (p=0.046).

TABLE 32

Effect of L-carnitine and Exercise on FBR of Muscle Samples in Female Test Dogs

| | FBR |
| --- | --- |
| Female, L-carnitine, run | 3.26[a] |
| Female, control, run | 7.01[b] |
| P value | 0.046 |
| SEM | 1.11 |

Levels not connected by the same letter are significantly different

Running male dogs on the low L-carnitine diet had a 5.04% FBR of skeletal proteins compared to 1.26% FBR for running L-carnitine-fed males, indicating that the FBR in exercised control dogs was almost significantly higher than in exercised L-carnitine males (Table 33).

TABLE 33

Effect of L-carnitine and Exercise on FBR of Muscle Samples in Male Test Dogs

| | FBR |
| --- | --- |
| Male, L-carnitine, run | 1.26[a] |
| Male, control, run | 5.04[b] |
| P value | 0.08 |
| SEM | 1.36 |

Levels not connected by the same letter are significantly different

The muscle samples were also analyzed for fractional synthesis rate (FSR). FSR was calculated as: ks=APEb/APEf×1/t×100, where APEb=15N atom percent excess (relative to natural abundance) of phenylalanine in protein; APEf=15N atom percent excess of free phenylalanine in tissues, assumed as the precursor pool; and t=time [d]. The % FSR of skeletal protein did not increase in male or female L-carnitine dogs in comparison to the control dogs. The resting dogs from both treatment groups, CARNITINE and control, showed a numerical increase in % FSR of skeletal protein compared to the dogs evaluated immediately after the 15 mile run (Table 6). The lack of significant difference in the % FSR between either treatment groups demonstrates that L-carnitine does not lead to protein synthesis and therefore does not play a significant role in building lean muscle mass.

TABLE 34

Fractional Synthesis Rate (FSR) by Gender, Exercise, and Treatment

| | FSR |
| --- | --- |
| Female, L-carnitine, no run | 5.04 |
| Female, L-carnitine, run | 2.54 |
| Female, control, no run | 6.99 |
| Female, control, run | 4.95 |
| Male, L-carnitine, no run | 3.61 |
| Male, L-carnitine, run | 4.63 |
| Male, control, no run | 3.33 |
| Male, control, run | 2.51 |
| P value | 0.86 |
| SEM | 4.07 |

Part Three: In part three of the study, L-carnitine was shown to increase oxygen consumption and energy expenditure in female test dogs. Sixteen Labrador Retrievers ranging in age from 1.5 to 3 years were fed low carnitine basal diets with and without added L-carnitine for a 37 week period that included part one and two of the study. Eight (4 male and 4 female) of the test L-carnitine dogs were each fed 3.75 g sugar and 250 mg of L-carnitine, while the other eight dogs (4 male and 4 female) were fed only 4 g of sugar each day for the experimental period. The sixteen test dogs were fed the same diet for parts one, two, and three of the study.

The test dogs were chosen during part two of the study based on their body weight, running ability, genetics, and body composition. Equal numbers of male and female dogs were selected for each group. The test dogs were also chosen for the initial ability for running on a human (21"×50") treadmill.

During parts one and two of the study, the sixteen test dogs ran outside from 5 to 15 miles twice a week with the other dogs in each of the respective groups.

During part two of the study, the sixteen test dogs were introduced to the treadmill and a simulated mask comprising a plastic cone with a strap in order to prepare the dogs to tolerate an oxygen/carbon dioxide mask connected to the Oxymax calorimetric system. The dogs were also trained to run on a custom made Nexfit canine treadmill (36"×9 ft). Though the dogs required different amounts of time to grow comfortable with running on the treadmill with the Oxymax max, all of the test dogs had acclimated to both the mask and treadmill when data collection began.

During part three of the study, the 16 test dogs were exclusively exercised on the industry sized canine treadmill. Initial Oxymax data was developed for each of the test dogs at various times and speeds in order to determine appropriate speeds on the treadmill required to achieve maximum $VO_2$ concentration. The dogs were run for 15 minutes at 6.5 mph to determine $VO_2$ max. The 16 test dogs were then ran at 50% $VO_2$ max (equivalent to 4 mph) on the treadmill for 30 minutes to determine total energy expenditure (heat production).

The system used to acquire information on volume of oxygen consumption and energy expenditure was an Open-Circuit calorimeter, which employed air from the surrounding environment. A mask specially designed for dogs was used to recover the gas sample and ventilate the dog. A small sample was drawn for gas analysis and dried to assure that the readings were made in a sample that was not under the influence of water vapor air exiting the chamber. The $O_2$ and $CO_2$ sensors were connected to software, and instant values of $O_2$ and $CO_2$ were measured.

The 16 test dogs (8 L-carnitine dogs, 4 male and 4 female, and 8 control dogs, 4 male and 4 female) were exercised at a warm up speed of 2 mph for 5 minutes prior to running at $VO_2$ max for 15 minutes at 6.5 mph. The next week, the test dogs ran again at a warm up speed of 2 mph for 5 minutes and then at 50% $VO_2$ max for 30 minutes at 4 mph.

The statistical analysis for gas exchange was analyzed by a factorial design 2×2 (2 genders and 2 diet treatments) and 2×2×2 (2 genders, 2 diets, 2 speeds) at p-value<0.05. The variable maximum oxygen consumption (Max $VO_2$) was the highest amount of oxygen consumption during the exercise time. The mean oxygen consumption (Mean $VO_2$) was the average amount of oxygen consumption during the exercise time. Oxygen consumption was reported on a per L/kg BW/h basis.

Energy expenditure was calculated using the formula for dogs (EE (kcal/d)=3.94 $VO_2$+1.11 V $CO_2$) (Weir, 1990). The maximum and mean energy expenditure was also calculated. Energy expenditure was reported at Kcal/metabolic body weight ($Kg^{0.75}$)/d as normally expressed in the literature for dogs.

Table 35 shows that the female L-carnitine dogs had higher oxygen consumption and energy expenditure at $VO_2$ Max than did the low L-carnitine female dogs. The female L-carnitine dogs had the highest Max $VO_2$ consumption at 6.5 mph (3.65 L/Kg/h); they also had a Mean $VO_2$ at 6.5 mph of 3.11 L/kg/hr (p=0.06). The female low-carnitine dogs had the lowest Max $VO_2$ consumption at 6.5 mph (2.61 L/Kg/h) (p=0.116) and the lowest Mean $VO_2$ consumption (2.46 L/kg/h) (p=0.06).

TABLE 35

Oxygen and Energy Expenditure in Dogs Exercised at Speed 6.5 for 15 Min (Considered $VO_2$ Max)

| Diet | Gender | Max $VO_2$ L/Kg/h | Mean $VO_2$ L/Kg/h | Max EE Kcal/$Kg^{0.75}$/d | Mean EE Kcal/ $Kg^{0.75}$/d |
|---|---|---|---|---|---|
| Sugar | | 2.87 | 2.70 | 799 | 746 |
| Carnitine | | 3.27 | 2.89 | 909 | 801 |
| | Male | 3.01 | 2.80 | 882 | 815 |
| | Female | 3.13 | 2.79 | 827 | 733 |
| Sugar | Male | 3.13 | 2.93 | 905 | 842 |
| Carnitine | Male | 2.89 | 2.66 | 858 | 788 |
| Sugar | Female | 2.61 | 2.46 | 693 | 651 |
| Carnitine | Female | 3.65 | 3.11 | 961 | 815 |
| | SEM | 0.370 | 0.225 | 115 | 66 |
| Source of variation | | | | | |
| Diet | | 0.3137 | 0.4159 | 0.3571 | 0.421 |
| Gender | | 0.7547 | 0.974 | 0.6432 | 0.2406 |
| Diet × Gender | | 0.1166 | 0.064 | 0.197 | 0.1264 |

EE: Energy expenditure
Levels not connected by the same letter are significantly different The maximum and mean values for energy expenditure of the female test dogs were not significant (p=0.197 and 0.127, respectively). The female L-carnitine and low carnitine dogs produced a max energy expenditure of 961 and 693 and a mean energy expenditure of 815 and 651 kcal/kg$BW^{0.75}$/d, respectively (Table 35). This lack of a significant difference in energy expenditure at 6.5 mph may be due to the occurrence of anaerobic respiration instead of aerobic respiration.

Table 36 shows that the female L-carnitine dogs also had higher oxygen consumption and energy expenditure at 50% $VO_2$ Max than did the low L-carnitine female dogs. The female L-carnitine dogs had the max $VO_2$ consumption at 50% $VO_2$ max (2.52 L/Kg/h). The female L-carnitine dogs had a mean $VO_2$ at 50% $VO_2$ max of 1.99 L/Kg/h (p=0.105). In comparison, the female low-carnitine dogs had the lowest max $VO_2$ consumption at 50% $VO_2$ max (2.08 L/Kg/h) and the lowest mean $VO_2$ consumption at 50% $VO_2$ max (1.75 L/Kg/h).

TABLE 36

Oxygen and Energy Expenditure in Test Dogs Exercised at Speed 4 for 30 Min (Considered 50% $VO_2$ Max)

| Diet | Gender | Max VO2 L/Kg/h | Mean VO2 L/Kg/h | Max EE Kcal/$Kg^{0.75}$/d | Mean EE Kcal/ $Kg^{0.75}$/d |
|---|---|---|---|---|---|
| Sugar | | 2.28 | 1.96 | 596 | 532 |
| Carnitine | | 2.39 | 1.98 | 716 | 576 |
| | Male | 2.36 | 2.07 | 653 | 571 |
| | Female | 2.30 | 1.87 | 659 | 534 |
| Sugar | Male | 2.47 | 2.18 | 669 ab | 588 a |
| Carnitine | Male | 2.26 | 1.97 | 637 ab | 554 ab |
| Sugar | Female | 2.08 | 1.75 | 523 b | 476 b |
| Carnitine | Female | 2.52 | 1.99 | 794 a | 598 a |
| | SEM | 0.170 | 0.128 | 58.2 | 29.1 |
| Source of variation | | | | | |
| Diet | | 0.5392 | 0.9118 | 0.0679 | 0.1686 |
| Gender | | 0.7234 | 0.1344 | 0.9278 | 0.2721 |
| Diet × Gender | | 0.0879 | 0.1053 | 0.0265* | 0.0247* |

EE: Energy expenditure
Levels not connected by the same letter are significantly different The female L-carnitine dogs produced the highest max and mean energy expenditure (794 and 598 kcal/Kg/h, respectively), while the female low carnitine dogs produced the lowest max and mean energy expenditure (523 and 476 kcal/Kg/h). This significant increase in energy expenditure for the L-carnitine females compared to the low carnitine females demonstrates that the L-carnitine provided fatty acids for fuel for the female test dog during the extended exercise period (Table 36). Possibly because of the extensive training that occurred over an extended period of time during parts one and two of the study, the female test dogs metabolically sensed the shortage in fuel in muscle and initiated fat mobilization early in the exercise.

The average female dog in part two of the study weighed 27.32 kg. A female Labrador Retriever that consumed 250 mg L-carnitine per day and ran at 50% of $VO_2$ Max generated 122 kcal/kg $BW^{0.75}$/d additional heat expenditure compared to a female Labrador Retriever that consumed a non-L-carnitine diet. In the present study, the extra energy value of L-carnitine for the average female lab was equivalent to 1458 kcal/d or 60.745 kcal/hr. The average kcal ME/g of the low Carnitine basal diet is 4 kcal. The quantity of low Carnitine basal food that is saved for a working female running at 50% $VO_2$ Max (4 mph) for one hour is 15.18 g.

This Oxymax data supports the protein turnover studies in part two that show females fed low carnitine diets increase (2×) the fractional breakdown rate of their skeletal muscle to continue running. The female fed L-carnitine did not need to breakdown muscle protein because the L-carnitine fed female was obtaining her fuel as mobilized fatty acids in the form of L-carnitine.

The p-value for diet×gender for 50% $VO_2$ Max was 0.088. At 50% $VO_2$ Max, the values for energy expenditure were very significant (p=0.026 and 0.025) for the diet×gender interaction. The diet effect for max energy expenditure at 50% $VO_2$ Max for both genders was almost significant (p=0.068) (Table 36).

As shown in Table 35 and 36, the male L-carnitine and low carnitine dogs were not significantly different for max and mean energy expenditure. During the short 30 minute study, the male test dogs may not be limited in fuel (glycogen) and therefore do not need additional fatty acids to be mobilized. In addition, in comparison to the female lab, the male lab may not be as efficient at partitioning fuel utilization during work. If the additional fat is not mobilized and utilized for fuel, there is less oxygen consumption and heat expenditure. Thus, additional running time at 50% $VO_2$ max may be required for male dogs to produce additional heat expenditure with L-carnitine.

The combined mean data for max oxygen consumption, mean oxygen consumption, max heat expenditure, and mean heat expenditure for treatment dogs running both speeds (4 mph for 50% $VO_2$ Max and 6.5 mph for $VO_2$ max) showed that the speed produced a significant difference for each variable (Table 37). The max oxygen consumption (p=0.04) and mean oxygen consumption (p=0.02) were both significant for the combined speeds for the diet and gender interaction. For the average of the combined speeds (4 mph for 50% $VO_2$ Max and 6.5 mph for $VO_2$ max), female L-carnitine dogs had a maximum $VO_2$ consumption of 3.02 L/Kg/h and a mean $VO_2$ consumption of 2.50 L/kg/h. For the female low carnitine dogs, the maximum and mean $VO_2$ consumption at the combined speeds were 2.34 and 2.10 L/kg/h, respectively. The maximum and mean energy expenditure for the combined work of 50% $VO_2$ Max and $VO_2$ max were close to being significant (p=0.107 and 0.058, respectively) for the diet×gender interaction.

TABLE 37

Oxygen and Energy expenditure in dogs exercised at speed 4.0 vs. 6.5 (Considered 50% $VO_2$ Max and $VO_2$ Max)

| Diet | Gender | Speed | Max VO2 L/Kg/h | Mean VO2 L/Kg/h | Max EE Kcal/Kg$^{0.75}$/d | Mean EE Kcal/Kg$^{0.75}$/d |
|---|---|---|---|---|---|---|
| Sugar | | | 2.57 | 2.33 | 718 | 643 |
| Carnitine | | | 2.80 | 2.40 | 793 | 675 |
| | Male | | 2.69 | 2.43 | 767 | 693 |
| | Female | | 2.68 | 2.30 | 743 | 625 |
| | | Speed 4 | 2.29 b | 1.94 b | 656 b | 544 b |
| | | Speed 6.5 | 3.07 a | 2.79 a | 854 a | 774 a |
| Sugar | Male | | 2.80 ab | 2.55 a | 787 | 715 |
| Carnitine | Male | | 2.57 ab | 2.31 ab | 748 | 671 |
| Sugar | Female | | 2.34 b | 2.10 b | 648 | 571 |
| Carnitine | Female | | 3.02 a | 2.50 a | 838 | 679 |
| | | SEM | 0.210 | 0.129 | 69 | 38 |
| Source of variation | | | | | | |
| Diet | | | 0.3015 | 0.5629 | 0.2839 | 0.4088 |
| Gender | | | 0.9787 | 0.3137 | 0.722 | 0.0885 |
| speed | | | 0.0011 | <.0001 | 0.0082 | <.0001 |
| Diet * Gender | | | 0.0412 | 0.0223 | 0.1072 | 0.0578 |
| Diet * speed | | | 0.4023 | 0.3901 | 0.6131 | 0.5492 |
| Gender * speed | | | 0.5494 | 0.341 | 0.6652 | 0.7142 |
| Diet * Gender * speed | | | 0.3706 | 0.2838 | 0.541 | 0.3972 |

EE: Energy expenditure
Levels not connected by the same letter are significantly different These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method for decreasing skeletal muscle damage and/or oxidative stress during and after intense physical activity of an active canine, the method comprising administering to the active canine that is and/or has undergone physical activity that lasts $_{at\ least}$ 20 minutes and increases a heart rate from about 5% to about 150% or more of a resting heart rate and results in an intensity equivalent to at least 50% of the active canine's $VO_2$ max, an effective amount of an L-carnitine supplement, and wherein the L-carnitine is administered to the active canine in an amount from about 50 to about 250 mg per day.

2. A method as defined in claim 1, wherein the L-carnitine supplement is administered without administering an amino acid supplement.

3. A method as defined in claim 1, wherein the L-carnitine supplement is administered at least every one to three days.

4. A method as defined in claim 1, wherein the L-carnitine supplement is administered daily.

5. A method as defined in claim 1, wherein L-carnitine is administered to the active canine in an amount from 30 milligrams to 250 milligrams per dose.

6. A method as defined in claim 1, wherein the L-carnitine supplement is administered orally.

7. A method as defined in claim 1, wherein the L-carnitine supplement is combined with a food composition and administered to the active canine.

8. A method as defined in claim 1, wherein the L-carnitine supplement comprises a solid.

9. A method as defined in claim 1, wherein the L-carnitine supplement is administered to the active canine in an amount sufficient to inhibit increases in myoglobin amounts in blood after activity.

10. A method as defined in claim 1, wherein the L-carnitine supplement is administered to the active canine in an amount sufficient to lower a fractional breakdown rate (FBR) in muscle samples and in an amount sufficient to increase lean mass.

11. A method as defined in claim 1, wherein myoglobin amounts in blood are reduced by greater than 50% after activity in comparison to an active canine that is and/or has undergone the same physical activity that has not received the L-carnitine supplement.

12. A method as defined in claim 1, wherein the L-carnitine supplement is administered in an amount sufficient reduce thiobarbituric acid reactive substances amounts in blood by greater than 50% after activity in comparison to an active canine that is and/or has undergone the same physical activity that has not received the L-carnitine supplement.

13. A method as defined in claim 1, wherein thiobarbituric acid reactive substances amounts in blood are reduced by greater than 75% after activity in comparison to an active canine that is and/or has undergone the same physical activity that has not received the L-carnitine supplement.

14. A method as defined in claim 1, wherein the L-carnitine supplement is administered in an amount sufficient to reduce peroxidation of membranes due to physical stress.

15. A method as defined in claim 1, wherein the L-carnitine supplement is administered in an amount sufficient to decrease skeletal muscle damage and to decrease oxidative stress during and after physical activity.

16. A method as defined in claim 1, wherein the L-carnitine supplement comprises a liquid.

17. A method as defined in claim 1, wherein L-carnitine is administered to the active canine in an amount greater than about 2.0 mg/kg body weight per day to about 9.0 mg/kg body weight per day.

* * * * *